(12) United States Patent
Saxinger

(10) Patent No.: US 6,664,374 B1
(45) Date of Patent: Dec. 16, 2003

(54) POLYPEPTIDES COMPRISING IL-6 LIGAND-BINDING RECEPTOR DOMAINS

(75) Inventor: Carl Saxinger, Bethesda, MD (US)

(73) Assignee: The United States of America as represented by the Department of Health & Human Services, Washington, DC (US)

( * ) Notice: Subject to any disclaimer, the term of this patent is extended or adjusted under 35 U.S.C. 154(b) by 0 days.

(21) Appl. No.: 09/721,108

(22) Filed: Nov. 22, 2000

Related U.S. Application Data

(63) Continuation of application No. PCT/US00/23490, filed on Aug. 25, 2000.
(60) Provisional application No. 60/151,277, filed on Aug. 27, 1999.

(51) Int. Cl.[7] ............................................. C07K 14/715
(52) U.S. Cl. ..................... 530/350; 530/327; 530/328
(58) Field of Search ................................. 530/328, 350, 530/327

(56) References Cited

U.S. PATENT DOCUMENTS

| | | | |
|---|---|---|---|
| 5,132,403 A | | 7/1992 | Kishimoto |
| 5,171,837 A | | 12/1992 | Tanihara et al. |
| 5,171,840 A | * | 12/1992 | Kishimoto .................. 530/350 |
| 5,210,075 A | | 5/1993 | Scholz et al. |
| 5,216,128 A | | 6/1993 | Novick et al. |
| 5,324,483 A | | 6/1994 | Cody et al. |
| 5,470,952 A | | 11/1995 | Stahl et al. |
| 5,585,275 A | | 12/1996 | Hudson et al. |
| 5,591,646 A | | 1/1997 | Hudson et al. |
| 5,591,827 A | | 1/1997 | Brakenhoff et al. |
| 5,639,455 A | | 6/1997 | Shimamura et al. |
| 5,670,373 A | | 9/1997 | Kishimoto |
| 5,681,723 A | | 10/1997 | Ciliberto et al. |
| 5,702,672 A | | 12/1997 | DeWitt et al. |
| 5,712,383 A | | 1/1998 | Sheridan et al. |
| 5,723,120 A | | 3/1998 | Brakenhoff et al. |
| 5,789,552 A | | 8/1998 | Savino et al. |
| 5,792,850 A | | 8/1998 | Baumgartner et al. |
| 5,814,700 A | | 9/1998 | Brennan |
| 5,817,790 A | | 10/1998 | Tsuchiya et al. |
| 5,837,858 A | | 11/1998 | Brennan |
| 5,847,105 A | | 12/1998 | Baldeschwieler et al. |
| 5,849,283 A | | 12/1998 | Ciliberto et al. |
| 5,869,644 A | | 2/1999 | Shortle et al. |
| 5,869,696 A | | 2/1999 | Reddy et al. |
| 5,874,165 A | | 2/1999 | Drumheller |
| 5,886,104 A | | 3/1999 | Pedersen et al. |
| 6,031,074 A | | 2/2000 | Saxinger |

FOREIGN PATENT DOCUMENTS

| | | |
|---|---|---|
| WO | WO 91/02714 | 3/1991 |
| WO | WO 96/17869 | 6/1996 |
| WO | WO 96/18648 | 6/1996 |
| WO | WO 96/35782 | 11/1996 |
| WO | WO 97/13781 | 4/1997 |
| WO | WO 97/48728 | 12/1997 |
| WO | WO 98/03657 | 1/1998 |
| WO | WO 98/15283 | 4/1998 |

OTHER PUBLICATIONS

Brakenhoff et al., "Development of Human IL–6 Receptor Antagonists," *Annals New York Academy of Science*, 762, 129–135 (Jul. 1995).

Falus, "Cytokine Receptor Architecture, Structure and Genetic Assembly," *Immunology Letters*, 44 (2–3), 221–223 (Jan. 1995).

Grube et al., "Identification of a Regulatory Domain of the Interleukin–6 Receptor," *Journal of Biological Chemistry*, 26 (32), 20791–20797 (Aug. 1994).

Halimi et al., "Epitope Peptides From Interleukin–6 Receptor which Inhibit the Growth of Human Myeloma Cells," *Eur. Cytokine Netw.*, 6 (3), 135–143 (May–Jun. 1995).

Kalai et al., "Analysis of the Human Interleukin–6/Human Interleukin–6 Receptor Binding Interface at the Amino Acid Level: Proposed Mechanism of Interaction," *Blood*, 89 (4), 1319–1333 (Feb. 1997).

Kalai et al., "Participation of Two Ser–Ser–Phe–Tyr Repeats in Interleukin–6 (IL–6)–Binding Sites of the Human IL–6 Receptor," *Eur. J. Biochem*, 238 (3), 714–723 (Jun. 1996).

Paonessa et al., "Two Distinct and Independent Sites on IL–6 Trigger GP130 Dimer Formation and Signalling," *EMBO Journal*, 14 (9), 1942–1951 (May 1995).

Weiergraber et al., "Use of Immobilized Synthetic Peptides for the Identification of Contact Sites Between Human Interleukin–6 and its Receptor," *FEBS Letters*, 379 (2), 122–126 (Jan. 1996).

Yamasaki et al., "Cloning and Expression of the Human Interleukin–6 (BSF–2/IFNBeta 2) Receptor," *Science*, 241 (4867), 825–828 (Aug. 1988).

Yawata et al., "Structure–Function Analysis of Human IL–6 Receptor: Dissociation of Amino Acid Residues Required for IL–6 Binding and for IL–6 Signal Transduction Through GP130," *EMBO Journal*, 12 (4), 1705–1712 (Apr. 1993).

Tanner et al., "The Conserved Box 1 Motif of Cytokine Receptors Is Required for Association with JAK Kinases," *The Journal of Biological Chemistry*, 270 (12), 6523–6530 (Mar. 1995).

* cited by examiner

Primary Examiner—Prema Mertz
(74) *Attorney, Agent, or Firm*—Leydig, Voit & Mayer, Ltd.

(57) ABSTRACT

The present invention provides, among other things, a polypeptide, and a pharmaceutically acceptable salt. thereof, that inhibits the binding of IL-6 ligand with IL-6 receptor under physiological conditions, a nucleic acid that encodes such a polypeptide and can be expressed in a cell, a nucleic acid that comprises or encodes an antisense nucleic acid molecule or a ribozyme that is specific for such a polypeptide, an antibody that is specific to such a polypeptide, an anti-antibody thereto, a composition comprising such a polypeptide, nucleic acid, antibody or an anti-body and a carrier therefor, a composition comprising a solid support matrix to which is attached an above-described polypeptide or an anti-antibody to a specified polypeptide sequence, a method of prophylactically or therapeutically inhibiting IL-6 signaling in a mammal in need thereof, a mammal in need thereof, and a method of removing IL-6 ligand from a bodily fluid of an animal.

1 Claim, 24 Drawing Sheets

|  |  | Formula | MW |
|---|---|---|---|
| E-2560 | H-Val-OH | $C_5H_{11}NO_2$ | 117.15 |
| E-3250 | H-[$^{15}$N]Val-OH | $C_5H_{11}^{15}NO_2$ | 118.15 |
| F-2180 | H-D-Val-OH | $C_5H_{11}NO_2$ | 117.15 |
| F-3025 | H-DL-Val-OH | $C_5H_{11}NO_2$ | 117.15 |
| E-3S10 | H-Val-ally ester p-tosylate | $C_8H_{16}NO_2 \cdot C_7H_8O_3S$ | 330.43 |
| E-2565 | H-Val-NH$_2$ · HBr | $C_5H_{12}N_7O \cdot HBr$ | 197.08 |
| E-2570 | H-Val-NH$_2$ · HCl | $C_5H_{12}N_2O \cdot HCl$ | 152.63 |
| E-2585 | H-Val-NHtBu | $C_9H_{20}N_2O$ | 172.27 |
| E-2600 | H-Val-p-nitrobenzyl ester · HBr | $C_{12}H_{16}N_2O_4 \cdot HBr$ | 333.19 |
| E-2590 | H-Val-OtBu · HCl | $C_9H_{19}NO_2 \cdot HCl$ | 209.72 |
| F-3170 | H-D-Val-OtBu · HCl | $C_9H_{19}NO_2 \cdot HCl$ | 209.72 |
| E-2575 | H-Val-OBzL · HCl | $C_{12}H_{12}NO_2 \cdot HCl$ | 243.74 |
| E-2580 | H-Val-OBzL · p-tosylate | $C_{12}H_{17}NO_2 \cdot C_7H_8O_3S$ | 379.48 |
| F-3500 | H-D-Val-OBzL · p-tosylate | $C_{12}H_{17}NO_2 \cdot C_7H_8O_3S$ | 379.48 |
| E-1825 | H-Val-OEt · HCl | $C_7H_{15}NO_2 \cdot HCl$ | 181.65 |
| E-2595 | H-Val-OMe · HCl | $C_6H_{13}NO_2 \cdot HCl$ | 167.64 |
| F-3160 | H-D-Val-OMe · HCl | $C_6H_{13}NO_2 \cdot HCl$ | 167.64 |
| C-3700 | Z-N-Me-Val-OH | $C_{14}H_{19}NO_4$ | 265.31 |
| C-2805 | Z-Val-OH | $C_{13}H_{17}NO_4$ | 251.28 |
| C-2810 | Z-D-Val-OH | $C_{13}H_{17}NO_4$ | 251.28 |
| C-2815 | Z-Val-NHtBu | $C_{12}H_{26}N_2O_3$ | 306.41 |
| C-2830 | Z-Val-ONp | $C_{19}H_{20}N_2O_4$ | 372.38 |
| C-2820 | Z-Val-OSu | $C_{17}H_{20}N_2O_4$ | 348.36 |
| C-2825 | Z-D-Val-OSu | $C_{17}H_{20}N_2O_4$ | 348.36 |

FIG. 1A

Special Amino Acids and Amino Acid Derivatives

| | |
|---|---|
| F-1190 | H-Abu-OH |
| F-2440 | H-Abu-NH$_2$ · HCl |
| F-3035 | H-Abu-OtBu · HCl |
| F-3755 | H-γ-Abu-OtBu · HCl |
| E-2660 | Ac-p-aminohippuric acid |
| F-1015 | Ac-p-amino-Phe-OMe |
| F-2275 | Ac-p-bromo-DL-Phe-OH |
| F-3265 | Ac-p-Bz-D-Phe-OH<br>[Ac-D-Bpa-OH] |
| M-1935 | Ac-Cys(farnesyl)-OH |
| F-2930 | Ac-Cys(farnesyl)-OMe |
| F-1020 | Ac-Dob(Boc)-OH |
| F-3175 | Ac-4,5 dehydro-Leu-OH |
| F-1030 | Ac-3,5-dinitro-Tyr-OEt |
| F-1010 | DL-2-Acetylamino-6-N-Boc-amino-4-hexynoic acid · DCHA |
| F-2295 | Ac-p-fluoro-DL-Phe-OH |
| F-3015 | Ac-p-iodo-D-Phe-OH |
| F-2940 | Ac-Met(O)-OH |
| F-2305 | Ac-5-Me-DL-Trp-OH |
| F-2420 | Ac-D-2-Nal-OH |
| F-1080 | Ac-DL-propargyl-Gly-OEt |
| E-3060 | H-Aib-OtBu |
| F-1160 | H-allo-Ile-OH |
| F-1165 | H-D-allo-Ile-OH |
| F-1170 | H-DL-allo-Ile-OH |

FIG. 1B

| | |
|---|---|
| F-1175 | H-allo-Thr-OH |
| F-1180 | H-D-allo-Thr-OH |
| F-2635 | H-DL-allo-Thr-OH |
| F-2545 | H-allo-Thr-OMe · HCl |
| F-2540 | H-allo-Thr(tBu)-OH |
| F-2560 | L-α-Aminoadipic acid [L-2-Aminohexanedioic acid] |
| F-2575 | D-α-Aminoadipic acid [D-2-Aminohexanedioic acid] |
| F-1185 | DL-α-Aminoadipic acid [DL-2-Aminohexanedioic acid] |
| F-3150 | L-2-Aminoadipic acid-δ-2-butyl ester [L-2-Aminohexanedioic acid-δ-2-butyl ester |
| F-3130 | L-α-Aminoadipic acid-δ-methyl ester · HCl [L-2-Aminohexanedioic acid-δ-methyl ester · HCl |
| F-3800 | 1-Aminocyclopropane-1-carbohydroxamic acid · HCl |
| F-3805 | 1-Aminocyclopropane-1-carboxylic acid |
| F-1200 | H-4-Amino-3,5-diodo-Phe-OH |
| F-1205 | 7-Aminoheptanoic acid |
| F-3480 | 4-Amino-1-methylimidazole-2-carboxylic acid-ethyl ester · HCl |
| F-3485 | 4-Amino-1-methylpyrrole-2-carboxylic acid methyl ester · HCl |
| F-1225 | H-p-Amino-Phe-OH · HCl |
| F-2855 | H-p-Amino-D-Phe-OH · HCl |
| F-1230 | H-p-Amino-DL-Phe-OH |
| F-1235 | DL-α-Aminopimelic acid [DL-2-Aminoheptanedioic acid] |
| H-3605 | 4-Aminopiperidine-4-carboxylic acid [H-Pip-OH] |
| F-2740 | L-2-Aminosuberic acid [L-2-Aminooctanedioic acid/H-Asu-OH] |

FIG. 1C

| | |
|---|---|
| F-3315 | D-a-Aminosuberic acid<br>[D-2-Aminooctanedioic acid/H-D-Asu-OH] |
| F-3305 | DL-α-Aminosuberic acid<br>[DL-2-Aminooctanedioic acid/H-DL-Asu-OH] |
| F3675 | H-3-Amino-Tyr-OH • 2 HCl<br>[5-Aminopentanoic acid-benzyl ester • p-tosylate] |
| E-1700 | n-Aminovaleric acid-benzyl ester • p-tosylate<br>[5-Aminopentanoic acid-benzyl ester • p-tosylate] |
| F-1281 | L-Azetidine –2-carboxylic acid |
| F-2285 | Azetidine-3-carboxylic acid |
| F3075 | H-p-Azido-Phe-OH |
| F-2490 | H-ß-(3-Benzothienyl)-Ala-OH |
| F-2485 | H-ß-(3-Benzathienyl)-D-Ala-OH |
| F-1215 | Bestatin<br>[(2S,3R)-3Amino-2-hydroxy-4-phenylbutanoyl-L-leucine] |
| F-2630 | S-[2,3-Bis(palmitoyloxy)-(2RS)-propyl]-N-palmitoyl-(R)-Cys-OH |
| A-1135 | Boc-Abu-OH |
| A-1175 | Boc-D-Abu-OH |
| A-1140 | Boc-γ-Abu-OH |
| A-1145 | Boc-Abu-ONp |
| A-3240 | Boc-Abz-OH |
| A-2800 | Boc-4-Abz-OH |
| A-4300 | Boc-4-Abz-Osu |
| A2015 | Boc-Aib-OH |
| A3825 | Boc-Aib-Osu |
| A-3345 | Boc-allo-Ile-OH |
| A-3735 | Boc-D-allo-Ile-OH |
| A-1150 | Boc-ε-aminocaproic acid |
| A-1155 | Boc-ε-aminocaproic acid-Osu |

FIG. 1D

| | |
|---|---|
| A-1160 | Boc-4-amino-3,5-diiodo-Phe-OH |
| A-1175 | Boc-7-aminoheptanoic acid |
| A-1185 | Boc-p-amino-Phe-OH |
| A-2980 | Boc-p-amino-D-Phe-OH |
| A-3975 | Boc-p-amino-Phe(Fmoc)-OH |
| A-4065 | Boc-p-amino-D-Phe(Fmoc)-OH |
| A-1455 | Boc-p-amino-Phe(Z)-OH |
| A-4370 | 1-Boc-4-aminopiperidine-4-carboxylic acid [H-Pip(Boc)-OH] |
| A-3310 | Boc-11-aminoundecanoic acid |
| A-3405 | Boc-δ-aminovaleric acid [Boc-5-aminopentanoic acid] |
| A-3S70 | Boc-p-azido-Phe-OH |
| A-4200 | Boc-p-azido-D-Phe-OH |
| A-3540 | Boc-β-(3-benzothienyl)-Ala-OH |
| A-3695 | Boc-p-bromo-Phe-OH |
| A-4205 | Boc-p-bromo-D-Phe-OH |
| A-4490 | Boc-p-tBu-Phe-OH |
| A-4485 | Boc-p-tBu-D-Phe-OH |
| A-3295 | Boc-p-Bz-Phe-OH [Boc-Bpa-OH] |
| A-3S60 | Boc-p-Bz-D-Phe-OH [Boc-D-Bpa-OH] |
| A-4325 | Boc-p-carboxy-Phe(OtBu)-OH • DCHA |
| A-3860 | Boc-β-chloro-Ala-OH |
| A-1525 | Boc-p-chloro-Phe-OH |
| A-2655 | Boc-p-chloro-D-Phe-OH |
| A-1535 | Boc-β-cyano-Ala-OH |

FIG. 1E

| | |
|---|---|
| A-1540 | Boc-ß-cyano-D-Ala-OH |
| A-4375 | Boc-p-cyano-Phe-OH |
| A-3760 | Boc-ß-cyclohexyl-Ala-OH |
| A-3840 | Boc-ß-cyclohexyl-D-Ala-OH |
| A-2960 | Boc-ß-cyclohexyl-Ala-OH • DCHA |
| A-2920 | Boc-ß-cyclohexyl-D-Ala-OH • DCHA |
| A-4465 | Boc-cyclohexyl-Gly-OH |
| A-4470 | Boc-cyclohexyl-D-Gly-OH |
| A-3340 | N-Boc-cyclohexylstatine [N-Boc-(3S,4S)-4-amino-5-cyclohexyl-3-hydroxypentanoic acid] |
| A-4150 | Boc-ß-cyclopropyl-Ala-OH |
| A-3215 | Boc-Dab-OH |
| A-4215 | Boc-D-Dab-OH |
| A-4415 | Boc-Dab-OtBu • HCl |
| A-4125 | Boc-Dab-(Aloc)-OH |
| A-3480 | Boc-Dab-(Boc)-OH • DCHA |
| A-3S20 | Boc-Dab-(Fmoc)-OH |
| A-4230 | Boc-D-Dab(Fmoc)-OH |
| A-2905 | Boc-Dab(Z)-OH • DCHA |
| A-4260 | Boc-D-Dab(Z)-OH •DCHA |
| A-3220 | Boc-Dap-OH |
| A-3S90 | Boc-D-Dap-OH |
| A-4115 | Boc-Dap(Aloc)-OH |
| A-3475 | Boc-Dap(Boc)-OH • DCHA |
| A-4130 | Boc-Dap(bromoacetyl)-OH |
| A-4290 | Boc-Dap(Dnp)-OH |
| A-4295 | Boc-Dap(Dnp)-OSu |

FIG. 1F

| | |
|---|---|
| A-3S80 | Boc-Dap(Fmoc)-OH |
| A-4235 | Boc-D-Dap(Fmoc)-OH |
| A-3000 | Boc-Dap(Z)-OH · DCHA |
| A-4265 | Boc-D-Dap(Z)-OH · DCHA |
| A-3485 | Boc-4,5-dehydro-Leu-OH · DCHA |
| A-1550 | Boc-3,4-dehydro-Pro-OH |
| A-1555 | Boc-3,5-dibromo-Tyr-OH |
| A-4220 | Boc-3,5-dibromo-D-Tyr-OH |
| A-4045 | Boc-3,4-dichloro-D-Phe-OH |
| A-1580 | Boc-3,5-diiodo-Tyr-OH |
| A-4225 | Boc-3,5-diiodo-D-Tyr-OH |
| A-1590 | Boc-3,5-diiodo-Tyr-OMe |
| A-1585 | Boc-3,5-diiodo-Tyr-OSu |
| A-1410 | Boc-3,5-diiodo-Tyr(3'-bromo-Bzl)-OH |
| A-2570 | Boc-3,5-diiodo-Tyr(2',6'-dichloro-Bzl)-OH |
| A-3065 | Boc-p-fluoro-Phe-OH |
| A-2835 | Boc-p-fluoro-D-Phe-OH |
| A-1605 | Boc-p-fluoro-DL-Phe-OH |
| A-4320 | Boc-α-(Fmoc-amino)-Gly-OH [Fmoc-α-(Boc-amino) Gly-OH] |
| A-4040 | Boc-Homoarg-OH · HCl |
| A-3775 | Boc-Homoarg(Et)$_2$-OH |
| A-3780 | Boc-D-Homarg(Et)$_2$-OH |
| A-3935 | Boc-Homoarg(NO$_2$)-OH |
| A-3465 | Boc-Homocit-OH |
| A-2870 | Boc-D-Homocit-OH |
| A-3420 | Boc-Homocys(Mbzl)-OH |

FIG. 1G

| | |
|---|---|
| A-4255 | Boc-D-Homocys(Mbzl)-OH |
| A-3610 | Boc-Homocys(Trt)-OH |
| A-1190 | Boc-Homophe-OH |
| A-1195 | Boc-D-Homophe-OH |
| A-2830 | Boc-Homopro-OH |
| A-3125 | Boc-D-Homopro-OH |
| A-4165 | Boc-7-hydroxy-Tic-OH |
| A-4170 | Boc-7-hydroxy-D-Tic-OH |
| A-1800 | Boc-p-iodo-Phe-OH |
| A-3640 | Boc-p-iodo-D-Phe-OH |
| A-1805 | Boc-p-iodo-DL-Phe-OH |
| A-3815 | Boc-isonipecotic acid [Boc-piperidine-4-carboxylic acid] |
| A-3715 | Boc-N-Me-Abz-OH |
| A-2025 | Boc-N-Me-allo-Ile-OH |
| A-3730 | Boc-N-Me-D-allo-Ile-OH |
| A-2880 | Boc-N-Me-p-chloro-D-Phe-OH |
| A-2070 | Boc-N-Me-p-nitro-Phe-OH · DCHA |
| A-4495 | Boc-p-Me-Phe-OH |
| A-4500 | Boc-p-Me-D-Phe-OH |
| A-1965 | Boc-Met(O)-OH |
| A-2885 | Boc-Met($O_2$)-OH |
| A-4145 | Boc-α-Me-DL-Val-OH |
| A-3225 | Boc-1-Nal-OH |
| A-4305 | Boc-D-1-Nal-OH |
| A-2850 | Boc-2-Nal-OH |
| A-2575 | Boc-D-2-Nal-OH |

FIG. 1H

| | |
|---|---|
| A-3110 | Boc-Neopentylgly-OH |
| A-4210 | Boc-D-Neopentylgly-OH |
| A-2125 | Boc-p-nitro-Phe-OH |
| A-2130 | Boc-p-nitro-D-Phe-OH |
| A-3645 | Boc-Oic-OH<br>[Boc-L-octohydroindole-2-carboxylic acid] |
| A-2965 | Boc-Pen(Acm)-OH |
| A-2970 | Boc-D-Pen(Acm)-OH |
| A-3660 | Boc-Pen(Mbzl)-OH · DCHA |
| A-3665 | Boc-D-Pen(Mbzl)-OH · DCHA |
| A-2900 | Boc-Pen(Mob)-OH |
| A-3990 | Boc-D-Pen(Mob)-OH |
| A-3650 | Boc-Pen(NPys)-OH |
| A-3655 | Boc-D-Pen(NPys)-OH |
| A-3S50 | Boc-Pen(Trt)-OH |
| A-3S55 | Boc-D-Pen(Trt)-OH |
| A-3915 | Boc-pentafluoro-Phe-OH |
| A-3960 | Boc-pentafluoro-D-Phe-OH |
| A-4385 | Boc-p-phenyl-Phe-OH<br>[Boc-β-(4-biphenyl)-Ala-OH; Boc-Bip-OH] |
| A-4390 | Boc-p-phenyl-D-Phe-OH<br>[Boc-β-(4-biphenyl)-D-Ala-OH; Boc-D-Bip-OH] |
| A-4100 | N-Boc-phenylstatine<br>[N-Boc-(3S,4S)-4-amino-3-hydroxy-5-phenylpentanoic acid] |
| B-3115 | 1-Boc-piperidine-4-Fmoc-amino-4-carboxylic acid<br>[Fmoc-Pip(Boc)-OH] |
| A-3745 | Boc-β-(3-pyridyl)-Ala-OH |
| A-2855 | Boc-β-(3-pyridyl)-D-Ala-OH |
| A-4395 | Boc-β-(2-quinolyl)-Ala-OH |
| A-4400 | Boc-β-(2-quinolyl)-D-Ala-OH |

FIG. 1I

| | |
|---|---|
| A-1180 | N-Boc-statine<br>[N-Boc-(3S,4S)-4-amino-3-hydroxy-6-methylheptanoic acid] |
| A-3945 | Boc-L-thiazolidine-4-carboxylic acid<br>[Boc-L-thioproline] |
| A-3940 | Boc-D-thiazolidine-4-carboxylic acid<br>[Boc-D-thioproline] |
| A-2290 | Boc-β-(2-thienyl)-Ala-OH |
| A-2295 | Boc-β-(2-thienyl)-D-Ala-OH |
| A-2300 | Boc-β-(2-thienyl)-DL-Ala-OH |
| A-3700 | Boc-L-thiocitrulline-OtBu |
| A-4360 | Boc-Thionoala-1-(6-nitro)benzotriazolide |
| A-4345 | Boc-Thionoleu-1-(6-nitro)benzotriazolide |
| A-4355 | Boc-Thionophe-1-(6-nitro)benzotriazolide |
| A-4365 | Boc-Thionoser(Bzl)-1-(6-nitro)benzotriazolide |
| A-4350 | Boc-Thionoval-1-(6-nitro)benzotriazolide |
| A-3070 | Boc-Tic-OH |
| A-3075 | Boc-D-Tic-OH |
| A-4090 | Boc-D-Tpi-OH<br>[Boc-D-1,2,3,4-tetrahydronoharman-3-carboxylic acid] |
| F-1305 | H-p-Bromo-Phe-OH |
| F-3700 | H-p-Bromo-D-Phe-OH |
| F-1310 | H-p-Bromo-DL-Phe-OH |
| F-3790 | H-p-tBu-Phe-OH |
| F-3795 | H-p-tBu-D-Phe-OH |
| F-3250 | n-Butyloxycarbonyl-Dap-OH |
| F-2800 | H-p-Bz-Phe-OH<br>[H-Bpa-OH] |
| F-2810 | H-p-Bz-D-Phe-OH<br>[H-D-Bpa-OH] |

FIG. 1J

| | |
|---|---|
| F-2345 | Carbamoyl-DL-Ala-OH |
| F-1375 | Carbamoyl-β-Ala-OH |
| M-2240 | Carbamoyl-Asp-OH · magnesium salt |
| F-2430 | Carbamoyl-Leu-OH |
| Q-1140 | β-Carboline-3-carboxylic acid-ethyl ester |
| Q-1145 | β-Carboline-3-carboxylic acid-propyl ester |
| F-3590 | H-p-Carboxy-Phe-OH |
| F-3585 | H-p-Carboxy-Phe(OtBu)-OH |
| F-2700 | L-Carnitine [(R)-β-Hydroxy-γ-(trimethylammonio)butyrate] |
| F-1425 | H-β-Chloro-Ala-OH |
| F-1430 | H-β-Chloro-Ala-OH · HCl |
| F-1435 | H-β-Chloro-D-Ala-OH · HCl |
| F-1440 | H-β-Chloro-DL-Ala-OH |
| F-2325 | H-β-Chloro-DL-Ala-OH · HCl |
| F-3380 | H-β-Chloro-Ala-NHOH |
| F-3465 | H-β-Chloro-Ala-OMe · HCl |
| F-1445 | H-p-Chloro-Phe-OH |
| F-2520 | H-p-Chloro-D-Phe-OH |
| F-1450 | H-p-Chloro-DL-Phe-OH |
| F-2690 | H-p-Cloro-D-Phe-OMe · HCl |
| F-1455 | H-p-Chloro-DL-Phe-OMe · HCl |
| F-1460 | H-β-Cyano-Ala-OH |
| F-3610 | H-p-Cyano-Phe-OH |
| F-2500 | H-β-Cyclohexyl-Ala-OH · HCl |
| F-2505 | H-β-Cyclohexyl-D-Ala-OH · HCl |
| F-3760 | H-Cyclohexyl-Gly-OH · salt |
| F-3765 | H-Cyclohexyl-D-Gly-OH · salt |

FIG. 1K

| | |
|---|---|
| F-2830 | Cyclohexylstatine<br>[(3S,4S)-4-Amino-5-cyclohexyl-3-hydroxypentanoic acid] |
| F-1470 | H-β-(1-Cyclopentenyl)-DL-Ala-OH |
| F-1465 | H-β-(1-Cyclopentenyl)-DL-Ala-OH |
| F-3470 | H-β-Cyclopropyl-Ala-OH |
| F-1475 | L-Cycloserine |
| F-1480 | D-Cycloserine |
| F-1485 | DL-Cycloserine |
| F-3050 | H-Dob-OH · 2 HCl |
| F-3055 | H-D-Dob-OH · 2 HCl |
| A-3305 | H-Dob(Boc)-OH |
| E-3360 | H-Dob(Boc)-OMe · HCl |
| F-3040 | H-Dop-OH · HCl |
| F-3045 | H-D-Dop-OH · HCl |
| F-3420 | H-Dop(Boc)-OMe · HCl |
| F-2985 | H-4,5-Dehydro-Leu-OH |
| F-2970 | H-trans-4,5-Dehydro-Lys-OH<br>[DL-trans-2,6-Diamino-4-hexenoic acid] |
| F-1490 | H-3,4 Dehydro-Pro-OH |
| F-2705 | H-3,4-Dehydro-DL-Pro-OH |
| F-1495 | H-3,4-Dehydro-Pro-NH$_2$ · HCl |
| F-1500 | H-3,4-Dehydro-Pro-OMe · HCl |
| F-1505 | 2,6-Diaminopimelic (LL,DD and Meso)<br>[2,6-Diaminoheptanedioic acid] |
| F-1510 | H-6-Diazo-5-oxo-Nle-OH<br>[L-DON] |
| F-2185 | H-6-Diazo-5-oxo-D-Nle-OH<br>[D-DON] |

FIG. 1L

| | |
|---|---|
| F-1520 | H-3,5-Dibromo-Tyr-OH |
| F-3395 | H-3,4-Dichloro-Phe-OH |
| F-3400 | H-3,4-Dichloro-D-Phe-OH |
| F-3695 | H-β,β,Dicyclohexyl-DL-Ala-OH |
| F-2395 | H-α-Difluoro-Me-DL-Orn-OH [DFMO] |
| F-1525 | H-β-(3,4-Dihydroxyphenyl)-DL-Ser-OH [DL-Threo-DOPS] |
| F-3460 | H-2,5-Diiodo-His-OH · HCL |
| F-2225 | H-3,5-Diiodo-Tyr-OH |
| F-3005 | H-3,5-Diiodo-D-Tyr-OH |
| E-2385 | H-3,5-Diiodo-Tyr-OMe · HCL |
| M-1925 | FA-Cys(farnesyl)-OH |
| M-1920 | FA-Cys(farnesyl)-OMe |
| F-2530 | H-β-Fluoro-DL-Ala-OH |
| F-3285 | H-m-Fluoro-Phe-OH |
| F-3290 | H-m-Fluoro-D-Phe-OH |
| F-2135 | H-m-Fluoro-DL-Phe-OH |
| F-1530 | H-p-Fluoro-Phe-OH |
| F-2320 | H-p-Fluoro-D-Phe-OH |
| F-1535 | H-p-Fluoro-DL-Phe-OH |
| F-3820 | H-p-Fluoro-Phe-OEt · HCL |
| F-3295 | H-m-Fluoro-D-Phe-OMe · HCL |
| F-1540 | H-p-Fluoro-DL-Phe-OMe · HCL |
| B-1780 | Fmoc-Abu-OH |
| B-2920 | Fmoc-D-Abu-OH |
| B-1910 | Fmoc-γ-Abu-OH |

FIG. 1M

| | |
|---|---|
| B-3260 | Fmoc-Abz-OH |
| B-2985 | Fmoc-4-Abz-OH |
| B-1860 | Fmoc-Aib-OH |
| B-2880 | Fmoc-allo-Ile-OH |
| B-2230 | Fmoc-D-allo-Ile-OH |
| B-3100 | Fmoc-allo-Thr-OH |
| B-3090 | Fmoc-D-allo-Thr-OH |
| B-1815 | Fmoc-allo-Thr(tBu)-OH |
| B-1810 | Fmoc-allo-Thr(tBu)-Odhbt |
| B-3280 | Fmoc-α-allyl-DL-Gly-OH [Fmoc-DL-2-amino-4-pentanoic acid] |
| B-2440 | Fmoc-L-α-aminoadipic acid-δ-t-butyl ester [Fmoc-L-2-aminohexanedioic acid-δ-t-butyl ester] |
| B-1560 | Fmoc-ε-aminocoproic acid |
| B-3310 | 2-(Fmoc-amino)-3-(2,2-dimethyl-4H-benzol[1,3]dioxin-6-yl)-propionic acid |
| B-2070 | Fmoc-p-amino-Phe-OH |
| B-1995 | Fmoc-p-amino-Phe-(Boc)-OH |
| B-2930 | Fmoc-p-amino-D-Phe-(Boc)-OH |
| B-2360 | Fmoc-p-azido-Phe-OH |
| B-2830 | Fmoc-β-(3-benzothienyl)-Ala-OH |
| B-3320 | Fmoc-p-tBu-Phe-OH |
| B-3325 | Fmoc-p-tBu-D-Phe-OH |
| B-2220 | Fmoc-p-Bz-Phe-OH [Fmoc-Bpa-OH] |
| B-2340 | Fmoc-p-Bz-D-Phe-OH [Fmoc-D-Bpa-OH] |
| B-3070 | Fmoc-p-carboxy-Phe(OtBu)-OH |
| B-2115 | Fmoc-p-chloro-Phe-OH |

FIG. 1N

| | |
|---|---|
| B-1900 | Fmoc-p-chloro-D-Phe-OH |
| B-3125 | Fmoc-p-cyano-Phe-OH |
| B-1975 | Fmoc-ß-cyclohexyl-Ala-OH |
| B-2345 | Fmoc-ß-cyclohexyl-D-Ala-OH |
| B-3270 | Fmoc-cyclohexyl-Gly-OH |
| B-3275 | Fmoc-cyclohexyl-D-Gly-OH |
| B-2905 | Fmoc-ß-cyclopropyl-Ala-OH |
| B-3120 | Fmoc-Cys(Boc-3-aminopropyl)-OH |
| B-2300 | Fmoc-Dab-OH |
| B-2365 | Fmoc-D-Dab-OH |
| B-2860 | Fmoc-Dab-(Adpoc)-OH |
| B-2850 | Fmoc-Dab-(aloc)-OH |
| B-1800 | Fmoc-Dab-(Boc)-OH |
| B-2960 | Fmoc-D-Dab(Boc)-OH |
| B-2270 | Fmoc-D-Dab(Fmoc)-OH |
| B-3250 | Fmoc-Dab(Z)-OH |
| B-2385 | Fmoc-Dap-OH |
| B-3055 | Fmoc-D-Dap-OH |
| B-2865 | Fmoc-Dap(Adpoc)-OH |
| B-2845 | Fmoc-Dap(Aloc)-OH |
| B-2380 | Fmoc-Dap(Boc)-OH |
| B-2965 | Fmoc-D-Dap(Boc)-OH |
| B-2995 | Fmoc-Dap(Dnp)-OH |
| B-2265 | Fmoc-Dap(Fmoc)-OH |
| B-2255 | Fmoc-4,5-dehydro-Leu-OH |
| B-1660 | Fmoc-3,4-dehydro-Pro-OH |

FIG. 10

| | |
|---|---|
| B-1275 | Fmoc-3,5-dibromo-Tyr-OH |
| B-1285 | Fmoc-3,5-Diiodo-Tyr-OH |
| B-3265 | Fmoc-3,5,dinitro-Tyr-OH |
| B-2595 | Fmoc-m-fluoro-Phe-OH |
| B-2835 | Fmoc-p-fluoro-Phe-OH |
| B-3210 | Fmoc-p-fluoro-D-Phe-OH |
| B-1550 | Fmoc-p-fluoro-DL-Phe-OH |
| B-3130 | Fmoc-Homoarg(Pmc)-OH |
| B-2250 | Fmoc-Homocit-OH |
| B-2390 | Fmoc-D-Homocit-OH |
| B-2405 | Fmoc-Homocys(Trt)-OH |
| B-1535 | Fmoc-Homophe-OH |
| B-2810 | Fmoc-D-Homophe-OH |
| B-2285 | Fmoc-Homopro-OH |
| B-2290 | Fmoc-D-Homopro-OH |
| B-2750 | Fmoc-p-iodo-Phe-OH |
| B-1740 | Fmoc-3-iodo-Tyr-OH |
| B-3190 | Fmoc-isonipecotic acid |
| B-2590 | Fmoc-DL-Isoser-OH |
| B-3335 | Fmoc-p-Me-Phe-OH |
| B-3330 | Fmoc-p-Me-D-Phe-OH |
| B-2130 | Fmoc-Met(O)-OH |
| B-1905 | Fmoc-Met($O_2$)-OH |
| B-1965 | Fmoc-1-Nal-OH |
| B-3020 | Fmoc-D-1-Nal-OH |
| B-2100 | Fmoc-2-Nal-OH |

FIG. 1P

| | |
|---|---|
| B-1950 | Fmoc-D-2-Nal-OH |
| B-2690 | Fmoc-m-nitro-p-hydroxy-Phe-OH [Fmoc-m-nitro-Tyr-OH] |
| B-1395 | Fmoc-p-nitro-Phe-OH |
| B-2350 | Fmoc-p-nitro-D-Phe-OH |
| B-2690 | Fmoc-m-nitro-Tyr-OH [Fmoc-m-nitro-p-hydroxy-Phe-OH] |
| B-2425 | Fmoc-Oic-OH [Fmoc-L-actahydroindole-2-carboxylic acid] |
| B-1885 | Fmoc-Pen(Acm)-OH |
| B-1915 | Fmoc-D-Pen(Acm)-OH |
| B-1545 | Fmoc-D-Pen(Bzl)-OH |
| B-2315 | Fmoc-Pen-(Trt)-OH |
| B-2320 | Fmoc-D-Pen(Trt)-OH |
| B-3155 | Fmoc-p-phenyl-Phe-OH [Fmoc-ß-(4-biphenyl)-Ala-OH; Fmoc-Bip-OH] |
| B-3160 | Fmoc-p-phenyl-D-Phe-OH [Fmoc-ß-(4-biphenyl)-D-Ala-OH; Fmoc-D-Bip-OH] |
| B-3195 | 1-Fmoc-piperidine-4-Fmoc-amino-4-carboxylic acid [Fmoc-Pip(Fmoc)-OH] |
| B-3175 | Fmoc-4-piperidylacetic acid [Fmoc-4-carboxymethyl-piperidine] |
| B-2005 | Fmoc-ß-(3-pyridyl)-Ala-OH |
| B-2040 | Fmoc-ß-(3-pyridyl)-D-Ala-OH |
| B-3165 | Fmoc-ß-(2-quinolyl)-Ala-OH |
| B-3170 | Fmoc-ß-(2-quinolyl)-D-Ala-OH |
| B-1665 | Fmoc-ß-(2-thienyl)-Ala-OH |
| B-2120 | Fmoc-ß-(2-thienyl)-D-Ala-OH |
| B-1920 | Fmoc-Tic-OH |
| B-1925 | Fmoc-D-Tic-OH |

FIG. 1Q

| | |
|---|---|
| B-2470 | Fmoc-Tyr(PO$_3$H$_2$)-OH |
| B-1990 | Fmoc-Tyr(PO$_3$Me$_2$)-OH |
| B-2275 | Fmoc-D-Tyr(PO$_3$Me$_2$)-OH |
| E-2870 | Glutaryl-Leu-OH · 2DCHA |
| G-4490 | Hippuryl-Cys(2-aminoethyl)-OH<br>[Bz-Gly-Cys(2-aminoethyl)-OH; BZ-Gly-4-thia-Lys-OH] |
| F-3815 | H-α-Homoethyl-Gly-OH |
| F-2780 | H-Homoarg-OH |
| F-2995 | H-Homocit-OH |
| F-2735 | H-D-Homocit-OH |
| F-1610 | H-Homophe-OH |
| F-1615 | H-D-Homophe-OH |
| F-1620 | H-DL-Homophe-OH |
| F-1625 | H-Homopro-OH |
| F-1630 | H-D-Homopro-OH |
| F-2915 | H-DL-Homopro-OH |
| F-2465 | H-Homopro-OMe · HCl |
| F-3125 | H-D-Homopro-OMe · HCl |
| F-3330 | H-(2S,4S)-γ-Hydroxy-Glu-OH |
| F-3335 | H-(2S,4R)-γ-Hydroxy-Glu-OH |
| Q-1420 | o-Hydroxyhippuric acid<br>[Salicyluric acid] |
| E-2655 | p-Hydroxyhippuric acid |
| F-1650 | H-DL-δ-Hydroxy-DL-Lys-OH · HCl |
| F-2335 | H-DL-δ-Hydroxy-DL-Lys(Boc)-OH |
| F-3685 | H-α-Hydroxy-nor-L-arginine<br>[L-2-Amino-(4-2'-hydroxyguanidino) butyric acid] |
| F-2935 | H-7-Hydroxy-Tic-OH |

FIG. 1R

| | |
|---|---|
| F-2990 | H-7-Hydroxy-D-Tic-OH |
| F-1665 | H-p-Iodo-Phe-OH |
| F-1670 | H-p-Iodo-D-Phe-OH |
| F-1675 | H-p-Iodo-DL-Phe-OH |
| F-3350 | H-m-Iodo-Tyr-OH |
| F-1695 | H-DL-Isoser-OH<br>[H-DL-β-Amino-α-hydroxypropionic acid] |
| F-1195 | Lysinoalanine·2 HCl (diastereomeric mixture: LL + LD)<br>H-Lys(DL-2-amino-2-carboxyethyl)-OH · 2HCl |
| F-1765 | N-Me-Aib-OH |
| F-1760 | N-Me-allo-Ile-Obzl · P-tosylate |
| F-1795 | H-α-Me-DL-His-OH · 2HCl |
| Q-1585 | Melphalan-methyl ester · 2HCl<br>[H-p-Di(2-chloroethyl)amino-Phe-OMe · 2HCl] |
| F-1800 | H-α-Me-DL-Leu-OH |
| F-1780 | N-Me-p-nitro-Phe-OH |
| E-3150 | H-α-Me-Phe-OH |
| F-3115 | H-α-Me-D-Phe-OH |
| F-1805 | H-α-Me-DL-Phe-OH |
| F-2805 | H-α-Me-DL-Phe-OMe · HCl |
| F-3780 | H-p-Me-Phe-OH |
| F-3785 | H-p-Me-D-Phe-OH |
| F-3440 | H-α-Me-Pro-OH |
| F-3615 | H-2-Mercapto-His-OH |
| F-3620 | H-2-Mercapto-His-OMe |
| M-2345 | H-β-(7-Methoxycoumarin-4yl)-Ala-OH<br>[L-2-Amino-3-(7-methoxycoumarin-4-yl)-propionic acid] |
| F-3810 | 1-Methylaminocyclopropone-1-carboxylic acid |

FIG. 1S

| | |
|---|---|
| F-1815 | H-γ-Methylene-DL-Glu-OH |
| Q-1645 | (2-Methyl-1-indolyl)acetic · DCHA |
| F-3180 | S-Methyl-L-thiocitrulline · acetate |
| F-2945 | H-Met(O)-OH |
| F-2895 | H-Met($O_2$)-OH |
| F-1810 | H-α-Me-DL-Trp-OH |
| F-2240 | H-α-Me-DL-Trp-OMe |
| F-1820 | H-1-Me-DL-Trp-OH |
| F-3535 | H-α-Me-Val-OH |
| F-3540 | H-α-Me-D-Val-OH |
| F-3355 | H-α-Me-DL-Val-OH |
| F-2550 | Myristoyl-Gly-OH |
| F-1840 | H-1-Nal-OH |
| F-1845 | H-D-1-Nal-OH |
| F-1850 | H-DL-1-Nal-OH |
| F-1855 | H-2-Nal-OH |
| F-1860 | H-D-2-Nal-OH |
| F-1865 | H-DL-2-Nal-OH |
| F-3710 | H-2-Nal-Obzl · salt |
| F-1315 | H-Neopentylgly-OH |
| F-1320 | H-D-Neopentylgly-OH |
| F-1325 | H-DL-Neopentylgly-OH |
| F-3340 | H-m-Nitro-p-hydroxy-Phe-OH [H-m-Nitro-Tyr-OH] |
| F-1895 | H-p-Nitro-Phe-OH |
| F-1900 | H-p-Nitro-D-Phe-OH |
| F-1905 | H-p-Nitro-DL-Phe-OH |

FIG. 1T

| | |
|---|---|
| F-1910 | H-p-Nitro-Phe-OMe · HCl |
| F-3340 | H-m-Nitro-Tyr-OH<br>[H-m-Nitro-p-hydroxy-Phe-OH] |
| F-3105 | H-Oic-OH<br>[L-Octahydroindole-2-carboxylic acid] |
| F-2515 | H-Pan-OH |
| F-3065 | H-Pan(Trt)-OH |
| F-3645 | H-β-Phenyl-Phe-OH<br>[H-β-(4-Biphenyl)-Ala-OH; H-Bip-OH |
| F-3650 | H-p-Phenyl-D-Phe-OH<br>[H-β-(4-Biphenyl)-D-Ala-OH; H-D-Bip-OH |
| F-2040 | H-Propargyl-Gly-OH |
| F-2900 | H-D-Propargyl-Gly-OH |
| F-2860 | H-DL-Propargyl-Gly-OH |
| F-2075 | H-Propargyl-Gly-OMe · HCl |
| F-2825 | H-β-(2-Pyridyl)-Ala-OH |
| F-2790 | H-β-(2-Pyridyl)-D-Ala-OH |
| F-2825 | H-β-(2-Pyridyl)-DL-Ala-OH |
| F-3195 | H-β-(3-Pyridyl)-Ala-OH |
| F-2640 | H-β-(3-Pyridyl)-D-Ala-OH |
| F-3705 | H-β-(3-Pyridyl)-DL-Ala-OH |
| F-3655 | H-β-(2-Quinolyl)-Ala-OH |
| F-3660 | H-β-(2-Quinolyl)-D-Ala-OH |
| F-2030 | H-Ser($PO_3H_2$)-OH |
| F-2035 | H-D-Ser($PO_3H_2$)-OH |
| F-3365 | H-Ser($SO_3H$)-OH |
| F-3370 | H-D-Ser($SO_3H$)-OH |

FIG. 1U

| | |
|---|---|
| F-1220 | Statine<br>[(3S,4S)-4-Amino-3-hydroxy-6-methylheptanoic acid] |
| F-3665 | L-4,5,6,7-Tetrahydra-1H-imidazo(4,5-c)pyridine-6-carboxylic acid |
| Q-1535 | L-Thiozoldin-2-one-4-carboxlic acid<br>[L-2-Oxothiozolidine-4-carboxlic acid] |
| F-2955 | H-β-(2-Thiozolyl)-DL-Ala-OH |
| F-2110 | H-β-(2-Thienyl)-Ala-OH |
| F-2115 | H-β-(2-Thienyl)-D-Ala-OH |
| N-1150 | H-β-(2-Thienyl)-DL-Ala-OH |
| F-2120 | H-β-(2-Thienyl)-DL-Ser-OH |
| N-1195 | DL-Thiorphan<br>[(DL-3-Mercapto-2-benzylproponoyl)-Gly-OH] |
| F-2460 | L-Thyronine<br>[H-p-(p-Hydroxypheonoxy)-Phe-OH] |
| F-2405 | DL-Thyronine<br>[H-p-(p-Hydroxyphenoxy)-DL-Phe-OH] |
| F-2580 | H-Tic-OH |
| F-2585 | H-D-Tic-OH |
| F-3310 | H-D-Tic-OtBu · HCl |
| Q-1700 | H-Tpi-OH<br>[L-1,2,3,4-Tetrahydronorharman-3-carboxlic acid] |
| F-3225 | H-β-(1,2,4-Triozol-1yl)-DL-Ala-OH |
| F-3670 | H-β-(Ureido)-Ala-OH<br>[H-β-((Aminocarbonyl)amino)-Ala-OH; L-Albizziine) |
| C-1260 | Z-Abu-OH |
| C-3160 | Z-γ-Abu-OH |
| C-1265 | Z-Abu-OSu |
| C-3350 | Z-3-Abz-OSu |
| C-3680 | Z-Aib-OH |

FIG. 1V

| | |
|---|---|
| C-3390 | Z-allo-Thr(tBu)-OH · DCHA |
| C-3385 | Z-L-α-aminoadipic acid<br>[Z-L-2-aminohexanedioic acid] |
| C-3790 | Z-L-2-aminoadipic acid-δ-t-butyl ester · DCHA<br>[Z-L-2-aminohexanedioic acid]-δ-t-butyl ester · DCHA] |
| C-1270 | Z-ε -aminocaproic acid |
| C-3975 | Z-p-carboxy-Phe(OtBu)-OH |
| C-3920 | Z-β-cyclohexyl-D-Ala-OH · DCHA |
| C-3705 | Z-Dob-OH |
| C-3770 | Z-D-Dob-OH |
| C-3510 | Z-Dob(Boc)-OH · DCHA |
| C-3765 | Z-D-Dob-(Boc)-OH · DCHA |
| C-3690 | Z-Dob(Z)-OH |
| C-3315 | Z-Dop-OH |
| C-3755 | Z-D-Dop-OH |
| C-3685 | Z-Dop(Boc)-OH · DCHA |
| C-3760 | Z-D-Dop(Boc)-OH |
| C-3695 | Z-Dop(Z)-OH |
| C-1535 | Z-dehydro-Ala-OH |
| C-1540 | Z-dehydro-Ala-OMe |
| C-3525 | Z-p-fluoro-Phe-OH |
| C-3965 | Z—D-Homocit-OH<br>[Z-α-amino-ε-uneidocaproic acid] |
| C-1275 | Z-Homophe-OH |
| C-1280 | Z-D-Homophe-OH |
| C-3010 | Z-1-Nal-OH |
| C3950 | Z-D-1-Nal-OH |
| C-3500 | Z-2-Nal-OH |

FIG. 1W

| | |
|---|---|
| C-2255 | Z-D-2-Nal-OH |
| C-2260 | Z-Neopentylgly-OH • DCHA |
| C-2265 | Z-D-Neopenlylgly-OH |
| C-4030 | Z-p-phenyl—Phe-OH<br>[Z-ß-(4-biphenyl)-Ala-OH; Z-Bip-OH] |
| C-4035 | Z-p-phenyl-D-Phe-OH<br>[Z-ß-(4-biphenyl)-D-Ala-OH;Z-D-Bip-OH] |
| C-3870 | Z-D-Tic-OH |

FIG. 1X

POLYPEPTIDES COMPRISING IL-6 LIGAND-BINDING RECEPTOR DOMAINS

This is a continuation of International application No. PCT/US00/23490, filed Aug. 25, 2000, which designates the U.S., and which claims priority to U.S. Provisional Patent Application No. 60/151,277, filed Aug. 27, 1999, both of which are incorporated by reference.

TECHNICAL FIELD OF THE INVENTION

The present invention relates to polypeptides comprising IL-6 ligand-binding receptor domains, nucleic acids encoding such polypeptides, antibodies, compositions comprising such polypeptides, nucleic acids, or antibodies, and methods of use.

BACKGROUND OF THE INVENTION

Interleukin-6 (IL-6) is a cytokine that is produced in response to various stimulators and is responsible for a variety of biological activities, including the stimulation of B- and T-cell growth and differentiation (Muraguchi et al.,*J. Exp. Med.* 167: 332 (1988)), production of acute-phase proteins in response to inflammation or tissue injury (Gauldie et al., *PNAS USA* 84: 7251 (1987); Geiger et al., *Eur. J. Immunol.* 18: 717 (1988)), multilineage hematopoiesis, osteoclast formation, maturation of megakaryocytes, and platelet production. These biological activities are initiated when IL-6 binds to the extracellular portion of the interleukin-6 receptor, which is variously referred to as the interleukin-6α subunit (IL-6Rα) or B-cell stimulating factor receptor (BSF-2 receptor). When IL-6 binds to IL-6Rα, a complex is formed. The complex then binds to the extracellular portion of the interleukin-6 receptor known as gp130, which is also referred to as the interleukin-6β subunit (IL-6Rβ). The resulting complex then transmits the IL-6 signal intracellularly.

The precursor of the IL-6 receptor reportedly comprises 468 amino acids (Yamasaki et al., *Science* 241: 825–828 (1988)). The mature IL-6 receptor reportedly comprises 449 amino acids (Yamasaki et al. (1988), supra).

Abnormal expression of IL-6 has been implicated in the pathogenesis of a variety of diseases, including multiple myeloma, plasmacytoma, hematological diseases such as plasma cell dyscrasias, leukemia and lymphoma (including non-Hodgkins's lymphoma and Lennert's T-cell lymphoma (Kishimoto, *Blood* 74: 1 (1989)), mesangial proliferative glomerulonephritis, polyclonal B-cell activation conditions, allergic diseases (Type I–IV), rheumatoid arthritis (Hirano et al., *Eur. J. Immunol.* 18: 1797 (1988)), diabetes, multiple sclerosis, SLE, septic shock, bacterial infection, viral infection, post-menopausal osteoporosis, chronic immune deficiency and autoimmune diseases (*Med. Immunol.* 15: 195–201 (1988)), including organ-specific and systemic diseases and AIDS, inflammatory diseases, and Cattleman's disease. In addition, IL-6 production has been associated with cardiac myxoma and cervical cancer (Kishimoto et al., *Ann. Rev. Immunol.* 6: 485 (1988)) in vivo and myelomas, histiocytomas and promyelocytic leukemia (Taga et al., *J. Exp. Med.* 166: 967 (1987)) in vitro. Attempts to abrogate the effects of abnormal expression of IL-6 can be made at its site of production or at its target.

In view of the above, there remains a need for materials and methods for identifying and designing agents that inhibit IL-signaling and for treating diseases involving IL-6 signaling prophylactically and therapeutically. It is an object of the present invention to provide such materials and methods.

This and other objects and advantages, as well as additional inventive features, will become apparent from the detailed description provided herein.

BRIEF SUMMARY OF THE INVENTION

The present invention provides, among other things, a polypeptide, and a pharmaceutically acceptable salt thereof, that inhibits the binding of IL-6 ligand with IL-6 receptor under physiological conditions. In one embodiment, the polypeptide has the formula $R^1R^*R^*L^*L^*L^*R^*R^2$, and pharmaceutically acceptable salts thereof, in which $R^1$ is hydrogen, $R^3C(O)$— or $R^3$, and does not comprise an amino acid residue sequence that is identical to an amino acid residue sequence of the α-chain of the IL-6 receptor and is not linked to the moiety —$R^*R^*L^*L^*L^*R^*$ via a glycinyl residue or via a proprionyl residue, $R^2$ is hydrogen, a polypeptide of from 1 to about 100 amino acid residues, $NHR^3$ or $R^3$, and $R^3$ is a pharmaceutically acceptable substituent group.

In another embodiment, the polypeptide has the formula $R^{10}R^{11}XVL^{*2}L^{*2}VR^{12}$, in which $R^{10}$ and $R^{12}$, independently, are pharmaceutically acceptable substituents, $R^{11}$ is a naturally-occurring or synthetic amino acid residue that has an acidic or neutral side-chain under physiological conditions, X is any naturally-occurring or synthetic amino acid residue, and $L^{*2}$ is leucinyl or isoleucinyl.

In yet another embodiment, the polypeptide has the formula $R^{20}R^{21}L^*R^*Y^*R^*A^*E^*R^*S^*R^{22}$, in which $R^{20}$ and $R^{22}$ are pharmaceutically acceptable substituents, $R^{21}$ is a naturally-occurring or synthetic amino acid residue that has a basic or neutral side-chain under physiological conditions, $L^*$, $Y^*$, $E^*$ and $S^*$ are independently any naturally-occurring or synthetic amino acid residue, $R^*$ is a naturally-occurring or synthetic amino acid residue that has a basic side-chain under physiological conditions, and $A^*$ is alaninyl, glycinyl, isoleucinyl, leucinyl, valinyl, norleucinyl, norvalinyl, sarcosinyl, β-alaninyl or α-aminoisobutyryl.

In still yet another embodiment, the polypeptide comprises at least $I^*A^*I^*V^*L^*R^*F^*$ but less than about 200 amino acid residues that have a sequence that is identical to an amino acid sequence of the α-chain of the IL-6 receptor, in which $I^*$, $L^*$, and $V^*$ are independently a naturally-occurring or synthetic amino acid residue having a side-chain consisting of a $C_1$–$C_6$ straight chain or $C_1$–$C_6$ branched alkyl moiety, $R^*$ is a naturally-occurring or synthetic amino acid residue that has a basic side-chain under physiological conditions, $A^*$ is alaninyl, glycinyl, isoleucinyl, leucinyl, valinyl, norleucinyl, norvalinyl, sarcosinyl, β-alaninyl or α-aminoisobutyryl, and $F^*$ is tyrosinyl, phenylalaninyl, tryptophanyl or α-aminoisobutyryl, with the proviso that at least four of the seven substituents of $I^*A^*I^*V^*L^*R^*F^*$ are selected such that $I^*$ is isoleucinyl, $A^*$ is alaninyl, $V^*$ is valinyl, $L^*$ is leucinyl, $R^*$ is argininyl, and $F^*$ is phenylalaninyl.

In a further embodiment, the polypeptide comprises up to 200 amino acid residues that are identical to an amino acid residue sequence of the β-chain of the IL-6 receptor and comprises the sequence SVIILKYNIQY (SEQ ID NO:6), TRWKSHLQNYTVNATKLTVNLTNDRY-LATLTVRNLVGKSDAAVL (SEQ ID NO:7), QLPVD-VQNGFIRNYTIFYRTIIGN (SEQ ID NO:8), or IVVPV-CLAFLLTTLLGVLFCFNKRDLIKKHIWPNVPDPSKSHIA (SEQ ID NO:9), any one of which can comprise from one to about six conservative or neutral replacements. The polypeptide can further comprise a pharmaceutically acceptable substituent.

Also provided by the present invention is a nucleic acid that encodes an above-described polypeptide, wherein the polypeptide preferably consists of naturally-occurring amino acid residues. The nucleic acid encoding the polypeptide can be expressed in a cell. The nucleic acid encoding the polypeptide can be operably linked to a signal sequence that causes secretion of at least the polypeptide by a cell in which the nucleic acid is expressed. Alternatively, the nucleic acid comprises or encodes an antisense nucleic acid molecule or a ribozyme that is specific for a nucleotide sequence in a nucleic acid encoding the specified amino acid sequence in an above-described polypeptide.

Further provided by the present invention is a composition comprising an above-described polypeptide or nucleic acid and a carrier therefor. Another composition provided by the present invention is a composition comprising an antibody to an above-described polypeptide, an anti-antibody to an above-described polypeptide, or a solid support matrix to which is attached an above-described polypeptide or an anti-antibody to the polypeptide sequence RRLLLR (SEQ ID NO:10), RXVLLV (SEQ ID NO:11), LRYRAERS (SEQ ID NO:12), IAIVLRF (SEQ ID NO:13), SVIILKYNIQY (SEQ ID NO:6), PSIKSVIILKYNIQY (SEQ ID NO:14), or a portion of any of the following polypeptides: WTNPSIKSVIILKYNIQY (SEQ ID NO:15), KLTWTNPSIKSVIILKYNIQY (SEQ ID NO:16), TRWKSHLQNYTVNATKLTVNLTNDRYLATLTVRNLVGKSDAAVL (SEQ ID NO:7), QLPVDVQNGFIRNYTIFYRTIIGN (SEQ ID NO:8), and IVVPVCLAFLLTTLLGVLFCFNKRDLIKKHIWPNVPDPSKSHIA (SEQ ID NO:9).

Also provided by the present invention is a method of prophylactically or therapeutically inhibiting IL-6 signaling in a mammal. The method comprises administering to a mammal in need thereof an IL-6 signaling inhibiting effective amount of an above-described polypeptide, a nucleic acid encoding such a polypeptide or an antibody to such a polypeptide.

In addition, the present invention provides a method of removing IL-6 ligand from a bodily fluid of an animal. The method comprises extracorporeally contacting the bodily fluid of the animal with a solid-support matrix to which is attached an above-described polypeptide or an anti-antibody to the polypeptide sequence RRLLLR (SEQ ID NO:10), RXVLLV (SEQ ID NO:11), LRYRAERS (SEQ ID NO:12), IAIVLRF (SEQ ID NO:13), SVIILKYNIQY (SEQ ID NO:6), PSIKSVIILKYNIQY (SEQ ID NO:14), or a portion of any of the following polypeptides: WTNPSIKSVIILKYNIQY (SEQ ID NO:15), KLTWTNPSIKSVIILKYNIQY (SEQ ID NO:16), TRWKSHLQNYTVNATKLTVNLTNDRYLATLTVRNLVGKSDAAVL (SEQ ID NO:7), QLPVDVQNGFIRNYTIFYRTIIGN (SEQ ID NO:8), and IVVPVCLAFLLTTLLGVLFCFNKRDLIKKHIWPNVPDPSKSHIA (SEQ ID NO:9). Alternatively, the bodily fluid can be contacted with the polypeptide or anti-antibody in solution and then the solution can be contacted with a solid support matrix to which is attached a means to remove the polypeptide or anti-antibody to which is bound IL-6 ligand from the bodily fluid.

BRIEF DESCRIPTION OF THE DRAWING

FIGS. 1a–1x depicts (referred to herein as FIG. 1) a listing of synthetic amino acids available (from Bachem, King of Prussia, Pa.) for incorporation into polypeptides and compounds of the present invention.

DETAILED DESCRIPTION OF THE INVENTION

The present invention provides, among other things, a polypeptide that inhibits the binding of IL-6 ligand with IL-6 receptor under physiological conditions. The present invention is predicated in part on a detailed study of a series of synthetic polypeptides having the same or similar amino acid sequence as that of IL-6 receptor, in which the ability of each synthetic polypeptide to bind to the IL-6 ligand was measured first in a high-throughput in vitro assay, and then confirmed (for at least a subpopulation of the synthetic polypeptides of greater interest) by measuring the ability of the synthetic peptide to inhibit the growth, replication, and survival of IL-6-dependent cells grown in a cellular growth medium comprising IL-6 ligand. Those of skill in the art will recognize that the ability of any particular polypeptide to inhibit IL-6 signaling or function in vivo can be easily and rapidly determined using either the techniques employed in the examples provided below, or by using another suitable testing technique, such as the B9 cell growth and signal transduction assays known in the art (see, e.g., Halimi et al., Eur.Cytokine Netw. 6: 135–43 (1995)). The skilled artisan would expect the results of such in vitro assays to be reasonably predictive of in vivo utility.

While not intending to be bound by any particular theory, it is believed that the present inventive polypeptide, and compositions comprising the same, inhibit the ability of IL-6 ligand to bind to the soluble IL-6 receptor or the membrane-bound IL-6 receptor, by binding to unbound IL-6 ligand with sufficient affinity to interfere competitively with IL-6 signaling, IL-6-dependent cellular responses (including changes in one or more of the group consisting of cellular metabolism, cellular growth, cellular replication, and cellular survival; the term "cellular metabolism" includes the ability of the cell to affect neighboring cells by secretion of biomolecules (e.g., paracrines, or exocrines), and/or display of cell-surface biomolecules (e.g., proteins or lipids)).

In each embodiment provided herein, a letter indicates the standard amino acid designated by that letter, and a letter followed directly by an asterisk (*) preferably represents the amino acid represented by the letter (e.g., N represents asparaginyl and T represents threoninyl), or a synthetic or naturally-occurring conservative or neutral substitution therefor, unless otherwise specified. Additionally, in accordance with convention, all amino acid sequences provided herein are given from left to right, such that the first amino acid is amino-terminal and the last is carboxyl-terminal. The synthesis of polypeptides, whether synthetic (i.e., chemical) or biological, is within the skill in the art.

It is within the skill of the ordinary artisan to select synthetic and naturally-occurring amino acids that effect conservative or neutral substitutions for any particular naturally-occurring amino acids. The skilled artisan desirably will consider the context in which any particular amino acid substitution is made, in addition to considering the hydrophobicity or polarity of the side-chain, the general size of the side chain and the pK value of side-chains with acidic or basic character under physiological conditions. For example, lysine, arginine, and histidine are often suitably substituted for each other, and more often arginine and histidine. As is known in the art, this is because all three amino acids have basic side chains, whereas the pK value for the side-chains of lysine and arginine are much closer to each other (about 10 and 12) than to histidine (about 6). Similarly, glycine, alanine, valine, leucine, and isoleucine are often suitably substituted for each other, with the proviso that glycine is frequently not suitably substituted for the other members of the group. This is because each of these amino acids are relatively hydrophobic when incorporated into a polypeptide, but glycine's lack of an α-carbon allows the phi and psi angles of rotation (around the α-carbon) so much conformational freedom that glycinyl residues can trigger changes in conformation or secondary structure that do not often occur when the other amino acids are substituted for each other. Other groups of amino acids frequently suitably substituted for each other include, but are not limited to, the group consisting of glutamic and aspartic acids; the group consisting of phenylalanine, tyrosine and tryptophan; and the group consisting of serine, threonine and, optionally, tyrosine. Additionally, the skilled artisan can readily group synthetic amino acids with naturally-occurring amino acids.

In the context of the present invention, a polypeptide is "substantially identical" to another polypeptide if it comprises at least about 80% identical amino acids. Desirably, at least about 50% of the non-identical amino acids are conservative or neutral substitutions. Also, desirably, the polypeptides do not differ in length (i.e., due to deletion mutations) by more than about 10%.

In a first embodiment, the present invention provides a polypeptide of the formula $R^1R*R*L*L*L*R*R^2$ (domain I), and pharmaceutically acceptable salts thereof. In this embodiment, $R^1$ is selected from the group consisting of hydrogen, $R^3C(O)$—, and $R^3$. However, $R^1$ does not comprise an amino acid residue sequence that is identical to an amino acid residue sequence of the α-chain of the IL-6 receptor and is not linked to the moiety —$R*R*L*L*L*R*$ via a glycinyl residue or a proprionyl residue. Preferably, $R^1$ is not linked to the moiety —$R*R*L*L*L*R*$ via either a glycinyl, proprionyl, butyryl, or alaninyl residue, and, more preferably, $R^1$ does not comprise an amino acid residue sequence that is greater than 50% identical to the amino acid residue sequence RWAGM— at the site of linkage to the moiety —$R*R*L*L*L*R*$.

R* is independently selected from the group consisting of argininyl, naturally-occurring argininyl equivalents, and synthetic argininyl equivalents.

L* is independently selected from the group consisting of leucinyl, naturally-occurring leucinyl equivalents, and synthetic leucinyl equivalents.

$R^2$ is selected from the group consisting of hydrogen, a polypeptide of from 1 to about 100 amino acid residues, —$NHR^3$, and $R^3$ The substituent $R^3$ is a pharmaceutically acceptable group. $R^3$ is independently selected with respect to size or length and secondary structure so that the present inventive polypeptide is able to bind to the IL-6 ligand with sufficient affinity to interfere competitively with IL-6 signaling under physiological conditions.

An amino acid residue equivalent thereof comprises a primary amine linked by one to three, preferably two, and more preferably one, methylenyl group(s) linked to a carboxylic acid, i.e., $NH_2$—$(CHR^a)_{1-3}$—$COO^-$, preferably $NH_2$—$(CHR^a)_2$—$COO^-$ and more preferably $NH_2$—$(CHR^a)$—$COO^-$. An amino residue (or its equivalent) is linked via a peptide bond (—C(O)NH—) to another amino acid residue (or its equivalent) or a polypeptide. An amino acid residue equivalent is an amino acid residue in which $R^a$ is selected to have the same charge under physiological conditions as the amino acid residue, and, preferably, is selected to have a similar number of atoms as the side-chain substituent of the amino acid residue, i.e., plus or minus 50%, preferably plus or minus 20%. All amino acid residue equivalents preferably have only one $R^a$ moiety that is not hydrogen (except for glycinyl equivalents for which Ra can be, and preferably is, repetitively selected as hydrogen, e.g., 3-amino proprionic acid; NH2—$(CH_2)_2$—$COO^-$. By way of example, an argininyl equivalent residue is preferably selected from the group consisting of argininyl and lysinyl because (1) these residues are naturally-occurring and are encoded by a mammalian gene or genome, and (2) these residues have (a) similar sizes (arginine having 7 side-chain atoms (excluding hydrogen atoms) and lysine having 5, ((5−7)/(7)×100%=28%)), and (b) these residues are bases having similar pK values (about 12 and 10, respectively).

An argininyl residue or an argininyl equivalent residue can be either natural or synthetic. In addition to an argininyl residue per se, a natural amino acid residue equivalent to an argininyl residue includes, but is not limited to, histidinyl and lysinyl, and is preferably lysinyl. A synthetic amino acid residue equivalent to and argininyl residue includes, but is not limited to, d-forms of argininyl, lysinyl, and histidinyl residues, as well as L- and D-, but preferably L-, ornithinyl, citrullinyl, and homoargininyl residues. The skilled artisan will recognize additional argininyl equivalents from FIG. 1.

A leucinyl residue or a leucinyl equivalent residue can be either natural or synthetic. Leucinyl equivalents include, but are not limited to, leucinyl, isoleucinyl, alaninyl, valinyl, norleucinyl, norvalinyl, sarcosinyl, β-alaninyl, and α-aminoisobutyryl. The skilled artisan will recognize additional leucinyl equivalents from FIG. 1. Of course, in any given polypeptide, substitutions are preferably limited in number. For example, in the polypeptide $R*R*L*L*L*R*$, all of the R* residues and all of the L* residues are most preferably argininyl and leucinyl, respectively; less preferably, one residue is other than argininyl or leucinyl, yet less preferably two or three residues are not argininyl or leucinyl, and least preferably four to six residues are not argininyl or leucinyl. Accordingly, a most preferred residue for R* is an argininyl residue.

Similarly, L* can be independently selected from the group consisting of leucinyl, isoleucinyl, and valinyl; preferably L* is leucinyl or isoleucinyl; and most preferably, L* is leucinyl. Additionally, L* can optionally be a d-form amino acid residue, and/or a synthetic residue such as, e.g., an α-aminoisobutyryl residue.

The substituent $R^3$ can be any suitable pharmaceutically acceptable substituent. A pharmaceutically acceptably substituent need not, but can provide a function, such as homing to sites of inflammation, increasing the solubility in water of the present inventive polypeptide, and protecting side-chains of amino acid residues from oxidative or chemical attack. For example, a pharmaceutically acceptable substituent can be a biopolymer, such as a polypeptide, an RNA, a DNA, or a polysaccharide. Suitable polypeptides comprise fusion proteins, an antibody or fragment thereof, a cell adhesion molecule or a fragment thereof, or a peptide hormone. Suitable polysaccharides comprise polyglucose moieties, such as starch and derivatives thereof, such as heparin. $R^3$ also can be any suitable lipid or lipid-containing moiety, such as a lipid of a liposome or a vesicle, saccharide or disaccharide, or even a lipophilic moiety, such as a prostaglandin, a steroid hormone, or a derivative of either of the foregoing. Additionally, $R^3$ can be a nucleotide or a nucleoside, such as nicotine adenine dinucleotide or thymine. $R^3$ also can be a vitamin, such as vitamin C, thiamine, or nicotinic acid. A pharmaceutically acceptable substituent can be a synthetic organic moiety, such as t-butyl carbonyl, an acetyl moiety, quinine, or polystyrene and another biologically acceptable polymer. A pharmaceutically acceptable substituent also can be $R^4$, wherein $R^4$ is selected from the group consisting of a $C_1$–$C_{18}$ alkyl, a $C_2$–$C_{18}$ alkenyl, a $C_2$–$C_{18}$ alkynyl, a $C_6$–$C_{18}$ aryl, a $C_7$–$C_{18}$ alkaryl, a $C_7$–$C_{18}$ aralkyl, and a $C_3$–$C_{18}$ cycloalkyl, wherein any of the foregoing $R^3$ groups that are cyclic comprise from 0 to 2 atoms per carbocyclic ring, which can be the same or different, selected from the group consisting of nitrogen, oxygen, and sulfur.

$R^4$ can be substituted by one to about six substituents, which can be the same or different, selected from the group consisting of an amino moiety, a carbamate moiety, a carbonate moiety, a phosphamate moiety, a phosphate moiety, a phosphonate moiety, a pyrophosphate moiety, a triphosphate moiety, a sulfamate moiety, a sulfate moiety, a sulfonate moiety, a $C_1$–$C_8$ monoalkylamine moiety, a $C_1$–$C_8$ dialkylamine moiety, and a $C_1$–$C_8$ trialkylamine moiety.

A preferred polypeptide of the first embodiment $R^1R*R*L*L*L*R*R^2$ is RRLLLR (SEQ ID NO:10), wherein R is argininyl and L is leucinyl. In a more preferred embodiment, $R^2$ of the formula $R^1R*R*R*L*L*L*R*R^2$ is a -(serinyl-valinyl-$R^5$), and $R^5$ is selected from the group consisting of hydrogen, a polypeptide of from 1 to about 98 amino acid residues, —NHR$^4$, and $R^4$, wherein $R^4$ is as defined above and can be substituted as described above.

In a second embodiment, the present invention provides a polypeptide of the formula $R^{10}R^{11}XVL^{*2}L^{*2}VR^{12}$, as well as pharmaceutically acceptable salts thereof. This embodiment is predicated, at least in part, on two surprising and unexpected discoveries. First, that a second domain of the α-chain of the IL-6 receptor that has the ability to bind to the IL-6 ligand comprises an important amino acid residue sequence —VLLV— (SEQ ID NO:18), which naturally occurs in the context TKAVLLVRF (SEQ ID NO:19). Second, that the binding affinity of this second domain is substantially increased if the lysinyl residue (in the larger subsequence) is replaced by an amino acid residue that does not have a side-chain that is basic under physiological conditions.

In this second embodiment, $R^{10}$ and $R^{12}$ are pharmaceutically acceptable substituents. Examples of pharmaceutically acceptable substituents are provided above with respect to $R^3$.

$R^{11}$ is selected from the group consisting of synthetic and naturally-occurring amino acid residues that have an acidic or neutral side-chain under physiological conditions. For example, $R^{11}$ can be selected from either the group consisting of alaninyl, asparaginyl, aspartyl, cysteinyl, glutaminyl, glutamyl, glycinyl, isoleucinyl, leucinyl, methioninyl, phenylalaninyl, prolinyl, serinyl, threoninyl, tryptophanyl, tyrosinyl, and valinyl, or the group consisting of norleucinyl, norvalinyl, sarcosinyl, β-alaninyl, α-aminoisobutyryl, γ aminopentane-1,5-dioyl, homoserinyl, hydroxyprolinyl, α-carboxyglutamyl, O-phosphoserinyl, O-phosphothreoninyl, and O-phosphotyrosinyl.

Similarly, X can be any synthetic or naturally-occurring amino acid residue, such as any synthetic or naturally-occurring amino acid residue that has an acidic or neutral side-chain under physiological conditions. That is, X can be selected from the group consisting of suitable $R^{11}$ residues, as well as from among the group consisting of argininyl, lysinyl, and histidinyl, or the group consisting of norleucinyl, norvalinyl, sarcosinyl, β-alaninyl, α-aminoisobutyryl, γ-aminopentane-1,5-dioyl, homoserinyl, hydroxyprolinyl, γ-carboxyglutamyl, O-phosphoserinyl, O-phosphothreoninyl, O-phosphotyrosinyl, ornithinyl, citrullinyl, and homoargininyl. However, X is preferably independently selected from the group denoted by $R^{11}$.

In the context of the formula $R^{10}R^{11}XVL^{*2}L^{*2}VR^{12}$, V is valinyl and $L^{*2}$ is leucinyl or isoleucinyl, and preferably leucinyl. As noted above, each substituent of the polypeptide is selected such that this present inventive polypeptide inhibits the binding of IL-6 with IL-6 receptor under physiological conditions.

The pharmaceutically acceptable group $R^{12}$ can optionally be the substituent $R^{13}$–$R^{14}$. Where $R^{12}$ is $R^{13}$–$R^{14}$, $R^{13}$ is selected from the group consisting of synthetic and naturally-occurring amino acid residues having a side-chain that is acidic or neutral under physiological conditions, including, but not limited to norleucinyl, sarcosinyl, β-alaninyl, α-aminoisobutyryl, γ-aminopentane-1,5-dioyl, homoserinyl, hydroxyprolinyl, α-carboxyglutamyl, O-phosphoserinyl, O-phosphothreoninyl, and O-phosphotyrosinyl. Where $R^{12}$ is $R^{13}$–$R^{14}$, $R^{14}$ is selected from the group consisting of hydrogen, a polypeptide of from 1 to about 100 amino acid residues, —NHR$^{15}$, and R$^{15}$. $R^{15}$ is a pharmaceutically acceptable substituent group (see $R^3$, supra). Preferably, $R^{13}$ is selected from the group consisting of naturally-occurring amino acid residues having a side-chain that is acidic or neutral under physiological conditions. Alternatively, $R^{13}$ is preferably selected from the group consisting of synthetic and naturally-occurring amino acid residues having a side-chain consisting of a $C_1$–$C_6$ straight-chained or branched alkyl moiety; for example, from the group consisting of glycinyl, alaninyl, isoleucinyl, leucinyl, valinyl, norleucinyl, sarcosinyl, β-alaninyl, and a-aminoisobutyryl. The polypeptide in which $R^{13}$ is alaninyl is among the preferred polypeptides of the second embodiment.

In one polypeptide of the second embodiment, $R^{15}$ is $R^{16}$, and $R^{16}$ is selected from the group consisting of hydrogen, a $C_1$–$C_{18}$ alkyl, a $C_2$–$C_{18}$ alkenyl, a $C_2$–$C_{18}$ alkynyl, a $C_6$–$C_{18}$ aryl, a $C_7$–$C_{18}$ alkaryl, a $C_7$–$C_{18}$ aralkyl, and a $C_3$–$C_{18}$ cycloalkyl, wherein any of the foregoing $R^{16}$ groups that are cyclic comprise from 0 to 2 atoms per carbocyclic ring, which can be the same or different, selected from the group consisting of nitrogen, oxygen, and sulfur.

Optionally, $R^{16}$ can be substituted by one to about six substituents, which can be the same or different, selected from the group consisting of an amino moiety, a carbamate moiety, a carbonate moiety, a phosphamate moiety, a phosphate moiety, a phosphonate moiety, a pyrophosphate moiety, a triphosphate moiety, a sulfamate moiety, a sulfate moiety, a sulfonate moiety, a $C_1$–$C_8$ monoalkylamine moiety, a $C_1$–$C_8$ dialkylamine moiety, and a $C_1$–$C_8$ trialkylamine moiety.

In another polypeptide of the second embodiment, $R^{10}$ is selected from the group consisting of hydrogen, a polypeptide of from 1 to about 100 amino acid residues, $R^{17}C(O)$—, and $R^{17}$, wherein $R^{17}$ is a pharmaceutically acceptable substituent group (see $R^3$, supra).

Similarly to $R^{16}$, $R^{17}$ can be selected from the group consisting of hydrogen, a $C_1$–$C_{18}$ alkyl, a $C_2$–$C_{18}$ alkenyl, a $C_2$–$C_{18}$ alkynyl, a $C_6$–$C_{18}$ aryl, a $C_7$–$C_{18}$ alkaryl, a $C_7$–$C_{18}$ aralkyl, and a $C_3$–$C_{18}$ cycloalkyl, wherein any of the foregoing $R^{17}$ groups that are cyclic comprise from 0 to 2 atoms per carbocyclic ring, which can be the same or different, selected from the group consisting of nitrogen, oxygen, and sulfur. In a preferred embodiment, $R^{17}$ is hydrogen.

Optionally, $R^{17}$ can be substituted by one to about six substituents, which can be the same or different, selected from the group consisting of an amino moiety, a carbamate moiety, a carbonate moiety, a phosphamate moiety, a phosphate moiety, a phosphonate moiety, a pyrophosphate moiety, a triphosphate moiety, a sulfamate moiety, a sulfate moiety, a sulfonate moiety, a $C_1$–$C_8$ monoalkylamine moiety, a $C_1$–$C_8$ dialkylamine moiety, and a $C_1$–$C_8$ trialkylamine moiety.

In a third embodiment, the present invention provides a polypeptide of the formula $R^{20}R^{21}L^*R^*Y^*R^*A^*E^*R^*S^*R^{22}$. This embodiment is predicated, at least in part, on three surprising and unexpected discoveries. First, that a third domain within the IL-6 receptor has the ability to bind to the IL-6 ligand and this domain has the essential core amino acid residue sequence —LRAERS— (SEQ ID NO:20), which naturally occurs in the larger subsequence -FELRAERSKT (SEQ ID NO:21). Second, that the affinity of this domain for the IL-6 ligand can be substantially enhanced if the acidic side chain of the first glutamyl residue in the larger sequence is eliminated or preferably is replaced by a small hydrophobic side-chain (e.g., as possessed by alanine). Third, that the lysinyl residue is preferably present and more preferably has a side-chain that is basic under physiological conditions.

In this third embodiment, $R^{20}$ and $R^{22}$ are pharmaceutically acceptable substituents. The substituent $R^{21}$ is selected from the group consisting of synthetic and naturally-occurring amino acid residues having a side-chain that is neutral or basic under physiological conditions, which includes, but clearly is not limited to, norleucinyl, norvalinyl, sarcosinyl, βalaninyl, α-aminoisobutyryl, homoserinyl, hydroxyprolinyl, ornithinyl, citrullinyl, and homoargininyl. Preferably, $R^{21}$ is alaninyl.

Additionally, L*, Y*, E*, and S* are each independently selected from the group consisting of synthetic and naturally-occurring amino acid residues. L* is preferably leucinyl or isoleucinyl. More preferably, L* is leucinyl. The substituent Y* is preferably selected from the group consisting of tyrosinyl, phenylalaninyl, tryptophanyl, and α-aminoisobutyryl. More preferably, Y* is tyrosinyl or phenylalaninyl, and most preferably, tyrosinyl. The substituent E* is preferably selected from the group consisting of synthetic and naturally-occurring amino acid residues having acidic side-chains under physiological conditions. For example, E* can be selected from the group consisting of glutamyl, aspartyl, γ aminopentane-1,5-dioyl, O-phosphoserinyl, 0-phosphothreoninyl, and O-phosphotyrosinyl. More preferably, E* is selected from the group consisting of glutamyl, aspartyl, and γ aminopentane-1,5-dioyl. Yet more preferably, E* is glutamyl. The substituent S* is selected from the group consisting of serinyl; threoninyl, phosphoserinyl, and phosphothreoninyl, and preferably is serinyl. The substituent A* is selected from the group consisting of alaninyl, glycinyl, and valinyl, and preferably is alaninyl.

Preferably, $R^{20}$ is selected from the group consisting of a polypeptide of from 1 to about 100 amino acid residues, hydrogen, $R^{23}$ C(O)—, and $R^{23}$. Similarly, $R^{22}$ is preferably selected from the group consisting of a polypeptide of from 1 to about 100 amino acid residues, hydrogen, —NHR$^{23}$, and $R^{23}$.

The substituent $R^{23}$ can be selected from the group consisting of a $C_1$–$C_{18}$ alkyl, a $C_2$–$C_{18}$ alkenyl, a $C_2$–$C_{18}$ alkynyl, a $C_6$–$C_{18}$ aryl, a $C_7$–$C_{18}$ alkaryl, a $C_7$–$C_{18}$ aralkyl, and a $C_3$–$C_{18}$ cycloalkyl, wherein any of the foregoing $R^{23}$ groups that are cyclic comprise from 0 to 2 atoms per carbocyclic ring, which can be the same or different, selected from the group consisting of nitrogen, oxygen, and sulfur.

$R^{23}$ can be substituted by one to about six substituents, which can be the same or different, selected from the group consisting of an amino moiety, a carbamate moiety, a carbonate moiety, a phosphamate moiety, a phosphate moiety, a phosphonate moiety, a pyrophosphate moiety, a triphosphate moiety, a sulfamate moiety, a sulfate moiety, a sulfonate moiety, a $C_1$–$C_8$ monoalkylamine moiety, a $C_1$–$C_8$ dialkylamine moiety, and a $C_1$–$C_8$ trialkylamine moiety.

R* is independently selected from the group consisting of synthetic or naturally-occurring amino acid residues having a side-chain that is basic under physiological conditions; for example, argininyl, lysinyl, ornithinyl, citrullinyl, or homoargininyl. Preferably, R* is selected from the group consisting of argininyl and lysinyl. More preferably, R* is argininyl.

A* is selected from the group consisting of alaninyl, glycinyl, isoleucinyl, leucinyl, valinyl, norleucinyl, norvalinyl, sarcosinyl, β-alaninyl, and α-aminoisobutyryl. Preferably, A* is alaninyl.

Additionally, the polypeptide of the third embodiment of the present invention can comprise additional polypeptides or protein motifs. Preferably, the present inventive polypeptide does not comprise more than about 200, and preferably more than about 50, additional amino acid residues that have an amino acid residue sequence that is identical (or at least 60% identical over a span of five or ten amino acid residues) to another amino acid residue sequence from the same chain of the IL-6 receptor.

In a fourth embodiment, the present invention provides a polypeptide, which comprises a sequence that inhibits binding of IL-6 ligand with IL-6 receptor under physiological conditions. The sequence comprises at least a polypeptide of the formula I*A*I*V*L*R*F*. This embodiment is predicated, at least in part, on the surprising and unexpected discovery that a fourth domain of the IL-6 receptor occurs in the membrane-associated region of the receptor, and this domain is centered about a region of the receptor having an amino acid residue sequence of IAIVLRFK (SEQ ID NO:23). This embodiment is further predicated on the surprising and unexpected discovery that this domain is highly tolerant of amino acid residue substitutions. For example, the basic residues of this sequence (i.e., argininyl and lysinyl) can be replaced by a non-conservative alaninyl substitution, which has the surprising effect of increasing the affinity of the domain for the IL-6 ligand.

In this fourth embodiment I*, L*, and V* are independently selected from the group consisting of synthetic and naturally-occurring amino acid residues having a side-chain consisting of a $C_1$–$C_6$ straight-chain or branched alkyl moiety.

R* is independently selected from the group consisting of synthetic and naturally-occurring amino acid residues having a side-chain that is basic under physiological conditions. For example, R* can be selected from the group consisting of argininyl, lysinyl, ornithinyl, citrullinyl, and homoargininyl. When R* is to be translated from a nucleic acid, R* preferably is selected from the group consisting of argininyl and lysinyl. R* is more preferably argininyl.

A* is selected from the group consisting of alaninyl, glycinyl, isoleucinyl, leucinyl, valinyl, norleucinyl, norvalinyl, sarcosinyl, β-alaninyl, and α-aminoisobutyryl.

F* is selected from the group consisting of tyrosinyl, phenylalaninyl, tryptophanyl, and α-aminoisobutyryl.

Preferably, at least four of the seven substituents, more preferably at least five substituents, yet more preferably at least six substituents of I*A*I*V*L*R*F, are selected such that I* is isoleucinyl, A* is alaninyl, V* is valinyl, L* is leucinyl, R is argininyl, and F* phenylalaninyl. Of course, all seven amino acid residues can be selected such that I*A*I*V*L*R*F* is IAIVLRFK (SEQ ID NO:23). The polypeptide is preferably selected such that it is small enough to bind effectively to IL-6 and does not comprise unnecessary extra atoms (making synthesis and processing of the polypeptide easier). The polypeptide preferably comprises less than about 200 amino acid residues, alternatively less than about 100 amino acid residues, alternatively less than about 30 amino acid residues, and alternatively less than about 16 amino acid residues that have a sequence that is identical to that of a region of the (α-chain of the IL-6 receptor.

Surprisingly, the affinity of the polypeptide for binding with IL-6 increases if any one, preferably two, and more preferably three, amino acid residues are bound via peptide bonds to the carboxyl-terminus of the sequence I*A*I*V*L*R*F*. Accordingly, the polypeptide preferably comprises at least the sequence IAIVLRFKXX (SEQ ID NO:24) in which X is any synthetic or naturally-occurring amino acid residue, as defined above, and preferably a synthetic or naturally-occurring amino acid residue of the formula NH$_2$—(CHR$^a$)—COO$^-$. Optionally, the sequence can comprise an amino-terminal tripeptide of the formula LLC-, or conservatively or neutrally substituted equivalents of LLC-. In this regard, the sequence can comprise at least the sequence LLCIAIVLRFK (SEQ ID NO:25). Additionally, the sequence can comprise at least the sequence FGTLLCIAIVLRFKKT (SEQ ID NO:26).

A fifth embodiment of the present invention is predicated on the surprising and unexpected discovery that the amino acid sequence SVIILKYNIQY (SEQ ID NO:6), which is a subsequence of the β-chain amino acid sequence of the IL-6 receptor, is critical in the binding between IL-6 ligand and IL-6 receptor. Accordingly, the present invention also provides a polypeptide that inhibits the binding of IL-6 ligand with IL-6 receptor under physiological conditions. The present inventive polypeptide of this fifth embodiment comprises the sequence SVIILKYNIQY (SEQ ID NO:6) and has an amino acid residue sequence of up to about 200 amino acid residues, preferably about 100 residues, more preferably about 50 residues, and optionally no or essentially no additional residues, that are identical to the β-chain of the IL-6 receptor or alternatively are at least about 60% identical over a span of about five or ten contiguous amino acid residues.

Biochemical analysis of this sequence revealed that the binding interaction is somewhat stronger if the sequence SVIILKYNIQY (SEQ ID NO:6), is extended on the amino terminus to include the sequence PSIK-. Accordingly, the present invention also provides a polypeptide of this fifth embodiment comprising the sequence PSIKSVIILKYNIQY (SEQ ID NO:14). Similar analyses further defined a region governing the binding between IL-6 ligand and its receptor. These analyses resulted in the identification and provision of polypeptides comprising the sequences WTNPSIKSVI-ILKYNIQY (SEQ ID NO:15)and KLTWTNPSIKSVIILKY-NIQY (SEQ ID NO:16), and up to about 200 amino acid residues that have an identical residue sequence to the sequence of the β-chain of the IL-6 receptor. Preferably, the polypeptides comprising the recited sequences comprise up to about 100 amino acid residues, more preferably, up to about 50 amino acid residues, from the IL-6 receptor β-chain sequence. Optionally, the polypeptide comprises no other, or essentially no other, sequence of amino acid residues that has an identical sequence to the sequence of the IL-6 receptor β-chain over a continuous stretch of five, or more preferably three, amino acid residues other than the sequences explicitly recited above. Additionally, the present inventive sequences preferably do not comprise a region of higher than about 60% homology to the IL-6 receptor over a stretch of at least five or ten contiguous amino acid residues, outside the region of the IL-6 receptor β-chain sequences explicitly recited above.

Alternatively, the present inventive β-chain polypeptides comprise a sequence consisting essentially of the recited sequence and polypeptides from other sources or origins that primarily contribute a function that is not directly related to IL-6 function or signaling.

In additional (sixth, seventh, and eighth) embodiments, the present invention provides a polypeptide of up to about 200 amino acid residues having a sequence that is identical to a portion of the sequence TRWKSHLQNYTVNAT-KLTVNLTNDRYLATLTVRNLVGKSDAAVL (SEQ ID NO:7), QLPVDVQNGFIRNYTIFYRTIIGN (SEQ ID NO:8), or IVVPVCLAFLLTTLLGVLFCFNKRD-LIKKHIWPNVPDPSKSHIA (SEQ ID NO:9), and that inhibits the binding of IL-6 ligand with IL-6 receptor under physiological conditions. The portion of the sequence can be any suitable size. For example, the portion of the amino acid sequence can be about a 6-mer, about a 12-mer, about an 18-mer, or about a 24-mer. An "n"-mer, as is understood in the art, is an oligopolymer consisting of "n" monomeric components or residues. Thus, a polypeptide comprising a portion of any of the preceding sequences that is a 6-mer, would comprise an amino acid sequence of any six adjacent residues of any one of the three preceding amino acid sequences. Preferably, the polypeptide comprises no more than about 100 amino acid residues, and more preferably no more than about 50 amino acid residues, having a sequence identical to that of the IL-6 receptor β-chain.

Conservative or neutral amino acid substitutions that do not destroy the ability of any of the above-described polypeptides to bind to IL-6 can be made. The replacement residues that substitute for the amino acid residues explicitly recited above can be either synthetic or naturally-occurring. Preferably, the number of substitutions is kept to a minimum, e.g., from 1 to about 6 conservative or neutral substitutions, and more preferably from 1 to about 3 conservative or neutral amino acid residue substitutions. While the residues substituted for the recited amino acid residues can be natural or synthetic, natural residues are preferred in those instances in which it is desirable for the amino acid residues to be encoded by a nucleic acid.

Additionally, any embodiment of the foregoing present inventive polypeptide can further comprise a pharmaceutically acceptable substituent, which is selected so that the polypeptide retains the ability to inhibit the binding of IL-6 ligand with IL-6 receptor under physiological conditions.

Also provided by the present invention is a nucleic acid that encodes an above-described polypeptide, which consists of naturally-occurring amino acid residues. The nucleic acid can be expressed in a cell.

In another embodiment, the present invention also provides a vector comprising a nucleic acid molecule as described above. A nucleic acid molecule as described above can be cloned into any suitable vector and can be used to transduce, transform, or transfect any suitable host. The selection of vectors and methods to construct them are commonly known to persons of ordinary skill in the art and are described in general technical references (see, in general, "Recombinant DNA Part D," *Methods in Enzymology*, Vol. 153, Wu and Grossman, eds., Academic Press (1987)). Desirably, the vector comprises regulatory sequences, such as transcription and translation initiation and termination codons, which are specific to the type of host (e.g., bacterium, fungus, plant, or animal) into which the vector is to be inserted, as appropriate and taking into consideration whether the vector is DNA or RNA. Preferably, the vector comprises regulatory sequences that are specific to the genus of the host. Most preferably, the vector comprises regulatory sequences that are specific to the species of the host and is optionally optimized for the expression of an above-described polypeptide.

Constructs of vectors, which are circular or linear, can be prepared to contain an entire nucleic acid sequence as described above or a portion thereof ligated to a replication system that is functional in a prokaryotic or eukaryotic host cell. Replication systems can be derived from ColE1, 2 mµ plasmid, λ, SV40, bovine papilloma virus, and the like.

Suitable vectors include those designed for propagation and expansion, or for expression, or both. A preferred cloning vector is selected from the group consisting of the pUC series, the pBluescript series (Stratagene, LaJolla, Calif.), the pET series (Novagen, Madison, Wis.), the pGEX series (Pharmacia Biotech, Uppsala, Sweden), and the pEX series (Clonetech, Palo Alto, Calif.). Examples of animal expression vectors include pEUK-C1, pMAM and pMAM-neo (Clonetech, Palo Alto, Calif.).

An expression vector can comprise a native or nonnative promoter operably linked to a nucleic acid molecule encoding an above-described polypeptide. The selection of promoters, e.g., strong, weak, inducible, tissue-specific and developmental-specific, is within the skill in the art. Similarly, the combining of a nucleic acid molecule as described above with a promoter is also within the skill in the art.

The nucleic acid encoding the polypeptide can be operably linked to a signal sequence that causes secretion of at least the polypeptide by a cell in which the nucleic acid is expressed. Signal sequences (alternatively called secretion sequences) are well-known in the art.

Alternatively, the nucleic acid comprises or encodes an antisense nucleic acid molecule or a ribozyme that is specific for a naturally-occurring, specified amino acid sequence of an above-described polypeptide. A nucleic acid sequence introduced in antisense suppression generally is substantially identical to at least a portion of the endogenous gene or gene to be repressed, but need not be identical. Thus, the vectors can be designed such that the inhibitory effect applies to other proteins within a family of genes exhibiting homology or substantial homology to the target gene. The introduced sequence also need not be full-length relative to either the primary transcription product or fully processed mRNA. Generally, higher homology can be used to compensate for the use of a shorter sequence. Furthermore, the introduced sequence need not have the same intron or exon pattern, and homology of non-coding segments will be equally effective.

Ribozymes also have been reported to have use as a means to inhibit expression of endogenous genes. It is possible to design ribozymes that specifically pair with virtually any target RNA and cleave the phosphodiester backbone at a specific location, thereby functionally inactivating the target RNA. In carrying out this cleavage, the ribozyme is not itself altered and is, thus, capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., *Nature* 334: 585–591 (1988).

Further provided by the present invention is a composition comprising an above-described polypeptide or nucleic acid and a carrier therefor. Another composition provided by the present invention is a composition comprising an antibody to an above-described polypeptide, an anti-antibody to an above described polypeptide, or a solid support matrix to which is attached an above-described polypeptide or an anti-antibody to the polypeptide sequence RRLLLR (SEQ ID NO:10), RXVLLV (SEQ ID NO:11), LRYRAERS (SEQ ID NO:12), IAIVLRF (SEQ ID NO:13), SVIILKYNIQY (SEQ ID NO:6), PSIKSVIILKYNIQY (SEQ ID NO:14), WTNPSIKSVIILKYNIQY (SEQ ID NO:15), KLTWT-NPSIKSVIILKYNIQY (SEQ ID NO:16), TRWKSHLQNY-TVNATKLTVNLTNDRYLATLTVRNLVGKSDAAVL (SEQ ID NO:7), QLPVDVQNGFIRNYTIFYRTIIGN (SEQ ID NO:6), or IVVPVCLAFLLTTLLGVLFCFNKRD-LIKKHIWPNVPDPSKSHIA (SEQ ID NO:9).

Antibodies can be generated in accordance with methods known in the art. See, for example, Benjamin, *In Immunology: a short course*, Wiley-Liss, NY, 1996, pp. 436–437; Kuby, *In Immunology*, 3rd. ed., Freeman, NY, 1997, pp. 455–456; Greenspan et al., *FASEB J*. 7: 437–443 (1993); and Poskitt, *Vaccine* 9: 792–796 (1991). Anti-antibodies (i.e., anti-idiotypic antibodies) also can be generated in accordance with methods known in the art (see, for example, Benjamin, *In Immunology: a short course*, Wiley-Liss, NY, 1996, pp. 436–437; Kuby, *In Immunology*, 3rd. ed., Freeman, NY, 1997, pp. 455–456; Greenspan et al., *FASEB J*., 7, 437–443, 1993; Poskitt, *Vaccine*, 9, 792–796, 1991; and Madiyalakan et al., *Hybridonor* 14: 199–203 (1995) ("Anti-idiotype induction therapy")). Such antibodies can be obtained and employed either in solution-phase or coupled to a desired solid-phase matrix. Having in hand such antibodies, one skilled in the art will further appreciate that such antibodies, using well-established procedures (e.g., such as described by Harlow and Lane (1988, supra), are useful in the detection, quantification, or purification of IL-6 ligand, IL-6 receptor, conjugates of each and host cells transformed to produce IL-6 receptor or a derivative thereof. Such antibodies are also useful in a method of prevention or treatment of a disease or dysfunction in an animal in which it is desirable to inhibit IL-6 signaling or function, as provided herein.

In view of the above, the present invention also provides a method of producing an antibody to the specific amino acid sequence of an above-described polypeptide. The method comprises administering an above-described polypeptide to an animal. The animal generates anti-polypeptide antibodies. Such an antibody can be administered to an animal to prevent or treat a disease or dysfunction in an animal in which it is desirable to inhibit IL-6 signaling or function, as provided herein.

Although nonhuman antibodies are useful for prophylactic or therapeutic treatment in humans, their favorable properties, in certain instances, can be further enhanced and/or their adverse properties further diminished, through "humanization" strategies, such as those recently reviewed by Vaughan, *Nature Biotech*., 16, 535–539, 1998.

Prior to administration to an animal, such as a mammal, in particular a human, an above-described polypeptide, nucleic acid or antibody can be formulated into various compositions by combination with appropriate carriers, in particular, pharmaceutically acceptable carriers or diluents, and can be formulated to be appropriate for either human or veterinary applications.

Thus, a composition for use in the method of the present invention can comprise one or more of the aforementioned polypeptides, nucleic acids or antibodies, preferably in combination with a pharmaceutically acceptable carrier. Pharmaceutically acceptable carriers are well-known to those skilled in the art, as are suitable methods of administration. The choice of carrier will be determined, in part, by whether a polypeptide or a nucleic acid is to be administered, as well as by the particular method used to administer the composition. One skilled in the art will also appreciate that various routes of administering a composition are available, and, although more than one route can be used for administration, a particular route can provide a more immediate and more effective reaction than another route. Accordingly, there are a wide variety of suitable formulations of compositions that can be used in the present inventive methods.

A composition in accordance with the present invention, alone or in further combination with one or more other active agents, can be made into a formulation suitable for parenteral administration, preferably intraperitoneal administration. Such a formulation can include aqueous and nonaqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives.

The formulations can be presented in unit dose or multi-dose sealed containers, such as ampules and vials, and can be stored in a freeze-dried (lyophilized) condition requiring only the addition of the sterile liquid carrier, for example, water, for injections, immediately prior to use. Extemporaneously injectable solutions and suspensions can be prepared from sterile powders, granules, and tablets, as described herein.

A formulation suitable for oral administration can consist of liquid solutions, such as an effective amount of the compound dissolved in diluents, such as water, saline, or fruit juice; capsules, sachets or tablets, each containing a predetermined amount of the active ingredient, as solid or granules; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers.

Similarly, a formulation suitable for oral administration can include lozenge forms, which can comprise the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, gels, and the like containing, in addition to the active ingredient, such carriers as are known in the art.

An aerosol formulation suitable for administration via inhalation also can be made. The aerosol formulation can be placed into a pressurized acceptable propellant, such as dichlorodifluoromethane, propane, nitrogen, and the like.

A formulation suitable for topical application can be in the form of creams, ointments, or lotions.

A formulation for rectal administration can be presented as a suppository with a suitable base comprising, for example, cocoa butter or a salicylate. A formulation suitable for vaginal administration can be presented as a pessary, tampon, cream, gel, paste, foam, or spray formula containing, in addition to the active ingredient, such carriers as are known in the art to be appropriate.

Important general considerations for design of delivery systems and compositions, and for routes of administration, for polypeptide drugs also apply (Eppstein, *CRC Crit. Rev. Therapeutic Drug Carrier Systems* 5, 99–139, 1988; Siddiqui et al., *CRC Crit. Rev. Therapeutic Drug Carrier Systems* 3, 195–208, 1987); Banga et al., *Int. J. Pharmaceutics* 48, 15–50, 1988; Sanders, *Eur. J. Drug Metab. Pharmacokinetics* 15, 95–102, 1990; Verhoef, *Eur. J. Drug Metab. Pharmacokinetics* 15, 83–93, 1990). The appropriate delivery system for a given polypeptide will depend upon its particular nature, the particular clinical application, and the site of drug action. As with any protein drug, oral delivery will likely present special problems, due primarily to instability in the gastrointestinal tract and poor absorption and bioavailability of intact, bioactive drug therefrom. Therefore, especially in the case of oral delivery, but also possibly in conjunction with other routes of delivery, it will be necessary to use an absorption-enhancing agent in combination with a given polypeptide. A wide variety of absorption-enhancing agents have been investigated and/or applied in combination with protein drugs for oral delivery and for delivery by other routes (Verhoef (1990), supra; van Hoogdalem, *Pharmac. Ther.* 44: 407–443, (1989); Davis, *J. Pharm. Pharmacol.* 44(Suppl. 1): 186–190, (1992). Most commonly, typical enhancers fall into the general categories of (a) chelators, such as EDTA, salicylates, and N-acyl derivatives of collagen, (b) surfactants, such as lauryl sulfate and polyoxyethylene-9-lauryl ether, (c) bile salts, such as glycholate and taurocholate, and derivatives, such as taurodihydrofusidate, (d) fatty acids, such as oleic acid and capric acid, and their derivatives, such as acylcarnitines, monoglycerides, and diglycerides, (e) non-surfactants, such as unsaturated cyclic ureas, (f) saponins, (g) cyclodextrins, and (h) phospholipids.

Other approaches to enhancing oral delivery of protein drugs can include the aforementioned chemical modifications to enhance stability to gastrointestinal enzymes and/or increased lipophilicity. Alternatively, the protein drug can be administered in combination with other drugs or substances that directly inhibit proteases and/or other potential sources of enzymatic degradation of proteins. Yet another alternative approach to prevent or delay gastrointestinal absorption of protein drugs is to incorporate them into a delivery system that is designed to protect the protein from contact with the proteolytic enzymes in the intestinal lumen and to release the intact protein only upon reaching an area favorable for its absorption. A more specific example of this strategy is the use of biodegradable microcapsules or microspheres, both to protect vulnerable drugs from degradation, as well as to effect a prolonged release of active drug (Deasy, in *Microencapsulation and Related Processes*, Swarbrick, ed., Marcell Dekker, Inc.: New York, 1984, pp. 1–60, 88–89, 208–211). Microcapsules also can provide a useful way to effect a prolonged delivery of a protein drug, such as an above-described polypeptide, after injection (Maulding, *J. Controlled Release* 6, 167–176, 1987).

In view of the above, the present invention further provides a method of prophylactically or therapeutically inhibiting IL-6 signaling in a mammal in need thereof. The method comprises administering to the mammal an IL-6 signaling-inhibiting effective amount of an above-described polypeptide, nucleic acid, or antibody to an above-described polypeptide or a nucleic acid encoding such a polypeptide.

The dose administered to an animal, such as a mammal, particularly a human, in the context of the present invention should be sufficient to effect a therapeutic or prophylactic (which desirably, but not necessarily, means absolute prevention as any degree of inhibition of IL-6 signaling in a mammal in need thereof is deemed beneficial) response in the individual over a reasonable time frame. The dose will be determined by the particular polypeptide, nucleic acid or antibody, administered, the severity of any existing disease state, as well as the body weight and age of the individual. The size of the dose also will be determined by the existence of any adverse side effects that may accompany the use of the particular polypeptide, nucleic acid or antibody employed. It is always desirable, whenever possible, to keep adverse side effects to a minimum.

The dosage can be in unit dosage form, such as a tablet or capsule. The term "unit dosage form" as used herein refers to physically discrete units suitable as unitary dosages for human and animal subjects, each unit containing a predetermined quantity of a vector, alone or in combination with other active agents, calculated in an amount sufficient to produce the desired effect in association with a pharmaceutically acceptable diluent, carrier, or vehicle. The specifications for the unit dosage forms of the present invention depend on the particular embodiment employed and the effect to be achieved, as well as the pharmacodynamics associated with each polypeptide, nucleic acid or antibody in the host. The dose administered should be an "IL-6 signaling-inhibiting effective amount" of an above-described active agent to achieve an "effective level" in the individual patient.

With respect to the above methods, sufficient amounts can be determined in accordance with methods known in the art. Similarly, the sufficiency of an immune response in an animal also can be assessed in accordance with methods known in the art. Either one of the above methods can further comprise concurrent, pre- or post-treatment with an adjuvant to enhance the immune response (see, for example, Harlow et al. (1988), supra).

Since the "effective level" is used as the preferred endpoint for dosing, the actual dose and schedule can vary, depending on interindividual differences in pharmacokinetics, drug distribution, and metabolism. The "effective level" can be defined, for example, as the blood or tissue level desired in the patient that corresponds to a concentration of one or more polypeptides, nucleic acids or antibodies according to the invention. The "effective level" for a polypeptide, nucleic acid or antibody of the present invention also can vary when the compositions of the present invention are used in combination with other known active agents.

One skilled in the art can easily determine the appropriate dose, schedule, and method of administration for the exact formulation of the composition being used, in order to achieve the desired "effective level" in the individual patient. One skilled in the art also can readily determine and use an appropriate indicator of the "effective level" of a polypeptide, nucleic acid or antibody of the present invention by a direct or indirect analysis of appropriate patient samples (e.g., blood and/or tissues).

It also will be appreciated by one skilled in the art that an above-described nucleic acid can be inserted ex vivo into animal cells, such as mammalian cells, in particular human cells, previously removed from such an animal. Such transformed autologous or homologous host cells, reintroduced into the animal or human, will express directly the corresponding polypeptide in vivo. The feasibility of such a therapeutic strategy to deliver a therapeutic amount of an agent in close proximity to the desired target cells has been demonstrated in studies with cells engineered ex vivo to express sCD4 (Morgan et al., (1994), supra). As an alternative to ex vivo insertion of the DNA sequences of the present invention, such sequences can be inserted into cells directly in vivo, such as by use of an appropriate viral or other suitable vector. Such cells transfected in vivo are expected to produce effective amounts of an above-described polypeptide directly in vivo.

Given the present disclosure, it will be additionally appreciated that an above-described nucleic acid sequence can be inserted into suitable nonmammalian host cells, and that such host cells will express therapeutic or prophylactic amounts of the desired polypeptide directly in vivo within a desired body compartment of an animal, in particular a human.

In addition, the present invention provides a method of removing IL-6 ligand from a bodily fluid of a mammal. The method comprises extracorporeally contacting the bodily fluid of the animal with a solid-support matrix to which is attached an above-described polypeptide or an anti-antibody to the polypeptide sequence RRLLLR (SEQ ID NO:10), RXVLLV (SEQ ID NO:11), LRYRAERS (SEQ ID NO:12), IAIVLRF (SEQ ID NO:13), SVIILKYNIQY (SEQ ID NO:6), PSIKSVIILKYNIQY (SEQ ID NO:14), WTNPSIKSVIILKYNIQY (SEQ ID NO:15), KLTWT-NPSIKSVIILKYNIQY (SEQ ID NO:16), TRWKSHLQNY-TVNATKLTVNLTNDRYLATLTVRNLVGKSDAAVL (SEQ ID NO:7), QLPVDVQNGFIRNYTIFYRTIIGN (SEQ ID NO:8), or IVVPVCLAFLLTTLLGVLFCFNKRD-LIKKHIWPNVPDPSKSHIA (SEQ ID NO:9). Alternatively, the bodily fluid can be contacted with the polypeptide or anti-antibody in solution and then the solution can be contacted with a solid support matrix to which is attached a means to remove the polypeptide or anti-antibody to which is bound IL-6 ligand from the bodily fluid. The method further comprises separating the bodily fluid and the solid support matrix by any suitable means.

Methods of attaching an above-described polypeptide or an anti-antibody to a solid support matrix are known in the art. "Attached" is used herein to refer to attachment to (or coupling to) and immobilization in or on a solid support matrix. See, for example, Harris, in *Poly(Ethylene Glycol) Chemistry: Biotechnical and Biomedical Applications*, Harris, ed., Plenum Press: New York (1992), pp. 1–14) and international patent application WO 91/02714 (Saxinger). Diverse applications and uses of functional polypeptides attached to or immobilized on a solid support matrix are exemplified more specifically for poly(ethylene glycol) conjugated proteins or peptides in a review by Holmberg et al. (In *Poly(Ethylene Glycol) Chemistry: Biotechnical and Biomedical Applications*, Harris, ed., Plenum Press: New York, 1992, pp. 303–324).

EXAMPLES

The following examples further illustrates the present invention but, of course, should not be construed as limiting the scope of the claimed invention in any way.

Synthetic peptide arrays were constructed in 96-well microtiter plates in accordance with the method set forth in WO 91/02714 (Saxinger), and used to test the binding of recombinant human IL-6 that had been labeled with radioactive iodine (radiolabeling by standard methods). After incubating the radiolabeled IL-6 ligand in a well with each synthetic peptide, a washing step was performed to remove unbound label, and the relative level of radioactivity remaining in each well of the plate was evaluated to determine the relative affinity of each peptide for IL-6 ligand. The synthesis of the peptides and the quantity of binding between the synthetic peptides and IL-6 ligand were found to be suitably reproducible, precise, and sensitive. Initial screening of the entire primary sequence of the IL-6 receptor molecule, taken 21 amino acid residues at a time, identified active binding sequences in four regions of the receptor corresponding to amino acid residues 66–86 (AAGSHPSRWAGMGRRLLLRSV) (SEQ ID NO:27), 136–156 (PRSTPSLTTKAVLLVRKFQNS) (SEQ ID NO:72), 246–266 (SSFYRLRFELRYRAERSKTFT) (SEQ ID NO:119), and 371–391 (GGSLAFGTLLCIAIVLRFKKT) (SEQ ID NO:168) (hereinafter domains I, II, III, and IV).

The authenticity of the binding signal was confirmed, at least for domains I–III, by demonstrating that antibodies that specifically bind to IL-6 ligand were able to inhibit the binding reactions. The binding between domain IV and IL-6 ligand was not similarly shown to be authentic because domain IV resides in the transmembrane region of the protein and is not believed to have been present in the soluble receptor used as an immunogen to raise the antibodies to IL-6 ligand.

Each of the four binding domains was analyzed in detail, which is set forth in these examples. First, serial truncations (or nested truncations) were performed from each end of the peptides to determine the location of the critical binding residues within each domain. Second, each amino acid residue in the critical regions of each domain were serially replaced by an alaninyl residue to indicate whether the side-chain of the residue at each particular location is likely to be essential or important to the mechanism of binding.

Example 1

This example provides data identifying domain I, as well as amino acid residues that are essential and/or important in the binding of domain I to human IL-6.

| Peptide Identifier | Peptide Sequence | SEQ ID No: | Counts/minute bound |
|---|---|---|---|
| A1: | AAGSHPSRWAGMGRRLLLRSV | 27 | 10739 |
| A2: | AAGSHPSRWAGMGRRLLLRS | 28 | 9764 |
| A3: | AAGSHPSRWAGMGRRLLLR | 29 | 8007 |
| A4: | AAGSHPSRWAGMGRRLLL | 30 | 5276 |
| A5: | AAGSHPSRWAGMGRRLL | 31 | 2747 |
| A6: | AAGSHPSRWAGMGRRL | 32 | 1753 |
| A7: | AAGSHPSRWAGMGRR | 33 | 1344 |
| A8: | AAGSHPSRWAGMGR | 34 | 1478 |
| A9: | AAGSHPSRWAGMG | 35 | 1474 |
| A10: | AAGSHPSRWAGM | 36 | 1444 |
| A11: | AAGSHPSRWAG | 37 | 1427 |
| A12: | AAGSHPSRWA | 38 | 1328 |
| A13: | AAGSHPSRW | 39 | 1520 |
| A14: | AAGSHPSR | 40 | 1353 |
| A15: | AAGSHPS | 41 | 1316 |
| A16: | AAGSHP | 42 | 1574 |
| A17: | AAGSHPSRWAGMGRRLLLRSV | 43 | 10884 |
| A18: | AGSHPSRWAGMGRRLLLRSV |  | 13393 |
| A19: | GSHPSRWAGMGRRLLLRSV | 44 | 10994 |
| A20: | SHPSRWAGMGRRLLLRSV | 45 | 12048 |
| A21: | HPSRWAGMGRRLLLRSV | 46 | 11969 |
| A22: | PSRWACMGRRLLLRSV | 47 | 11087 |
| A23: | SRWAGMGRRLLLRSV | 48 | 8272 |
| A24: | RWAGMGRRLLLRSV | 49 | 12069 |
| A25: | WAGMGRRLLLRSV | 50 | 12166 |
| A26: | AGMGRRLLLRSV | 51 | 7623 |
| A27: | GMGRRLLLRSV | 52 | 6820 |
| A28: | MGRRLLLRSV | 53 | 7136 |
| A29: | GRRLLLRSV | 54 | 5367 |
| A30: | RRLLLRSV | 55 | 5972 |
| A31: | RLLLRSV | 56 | 5464 |
| A32: | LLLRSV | 57 | 1599 |
| A33: | AAGSHPSRWAGMGRRLLLRSV | 27 | 10213 |
| A34: | AAGSHPSRWAGMGRRLLLRSA | 58 | 11797 |
| A35: | AAGSHPSRWAGMGRRLLLRAV | 59 | 11201 |
| A36: | AAGSHPSRWAGMGRRLLLASV | 60 | 4895 |
| A37: | AAGSHPSRWAGMGRRLLARSV | 61 | 7728 |
| A38: | AAGSHPSRWAGMGRRLALRSV | 62 | 7079 |
| A39: | AAGSHPSRWAGMGRRALLRSV | 63 | 5283 |
| A40: | AAGSHPSRWAGMGRALLLRSV | 64 | 4247 |
| A41: | AAGSHPSRWA*GMGA*RLLLRSV | 65 | 4461 |
| A42: | AAGSHPSRWAGM*ARRLLLRSV* | 66 | 12259 |
| A43: | AAGSHPSRWAGAGRRLLLRSV | 67 | 13521 |
| A44: | AAGSHPSRWAAMGRRLLLRSV | 68 | 11854 |

-continued

| Peptide Identifier | Peptide Sequence | SEQ ID No: | Counts/minute bound |
|---|---|---|---|
| A45: | AAGSHPSRAAGMGRRLLLRSV | 69 | 8040 |
| A46: | AAGSHPSAWAGMGRRLLLRSV | 70 | 9523 |
| A47: | AAGSHPARWAGMGRRLLLRSV | 71 | 11291 |

These data indicate that the sequence RRLLLR (SEQ ID NO:10) is a critical binding region within domain I, that domain I is preferably flanked on the amino-terminus by a pharmaceutically acceptable substituent equivalent in size to three amino acid residues, e.g., any three amino acid residues, and is preferably flanked on the carboxyl-terminus by a pharmaceutically acceptable substituent equivalent in size to at least one amino acid residue, and preferably two or three or more amino acid residues.

Example 2

This example provides data identifying the critical binding regions of domain II, as well as which residues within the critical binding domain that are essential and/or important in the binding of human IL-6 to IL-6 receptor within domain II.

| Peptide identifier | Peptide Sequence | SEQ ID NO: | Counts/minute bound |
|---|---|---|---|
| B1: | PRSTPSLTTKAVLLVRKFQNS | 72 | 10790 |
| B2: | PRSTPSLTTKAVLLVRKFQN | 73 | 7930 |
| B3: | PRSTPSLTTKAVLLVRKFQ | 74 | 7075 |
| B4: | PRSTPSLTTKAVLLVRKF | 75 | 4689 |
| B5: | PRSTPSLTTKAVLLVRK | 76 | 3962 |
| B6: | PRSTPSLTTKAVLLVR | 77 | 4355 |
| B7: | PRSTPSLTTKAVLLV | 78 | 3401 |
| B8: | PRSTPSLTTKAVLL | 79 | 1846 |
| B9: | PRSTPSLTTKAVL | 80 | 1402 |
| B10: | PRSTPSLTTKAV | 81 | 1216 |
| B11: | PRSTPSLTTKA | 82 | 1240 |
| B12: | PRSTPSLTTK | 83 | 1313 |
| B13: | PRSTPSLTT | 84 | 1053 |
| B14: | PRSTPSLT | 85 | 930 |
| B15: | PRSTPSL | 86 | 985 |
| B16: | PRSTPS | 87 | 1015 |
| B17: | PRSTPSLTTKAVLLVRKFQNS | 72 | 12347 |
| B18: | RSTPSLTTKAVLLVRKFQNS | 88 | 12958 |
| B19: | STPSLTTKAVLLVRKFQNS | 89 | 12150 |
| B20: | TPSLTTKAVLLVRKFQNS | 90 | 12885 |
| B21: | PSLTTKAVLLVRKFQNS | 91 | 13294 |
| B22: | SLTTKAVLLVRKFQNS | 92 | 12645 |
| B23: | LTTKAVLLVRKFQNS | 93 | 12153 |
| B24: | TTKAVLLVRKFQNS | 94 | 7014 |
| B25: | TKAVLLVRKFQNS | 95 | 5753 |
| B26: | TKAVLLVRKFQNS | 95 | 5226 |
| B27: | KAVLLVRKFQNS | 96 | 5604 |
| B28: | AVLLVRKFQNS | 97 | 9073 |
| B29: | VLLVRKFQNS | 98 | 9099 |
| B30: | LLVRKFQNS | 99 | 7205 |
| B31: | LVRKFQNS | 100 | 2525 |
| B32: | VRKFQNS | 101 | 1182 |
| B33: | PRSTPSLTTKAVLLVRKFQNS | 72 | 11699 |
| B34: | PRSTPSLTTKAVLLVRKFQNA | 102 | 11450 |
| B35: | PRSTPSLTTKAVLLVRKFQAS | 103 | 13185 |
| B36: | PRSTPSLTTKAVLLVRKFANS | 104 | 10090 |
| B37: | PRSTPSLTTKAVLLVRKAQNS | 105 | 11556 |
| B38: | PRSTPSLTTKAVLLVRAFQNS | 106 | 11117 |
| B39: | PRSTPSLTTKAVLLVAKFQNS | 107 | 10786 |
| B40: | PRSTPSLTTKAVLLARKFQNS | 108 | 4542 |
| B41: | PRSTPSLTTKAVLAVRKFQNS | 109 | 3758 |
| B42: | PRSTPSLTTKAV*ALVRKFQNS* | 110 | 3838 |
| B43: | PRSTPSLTTKAALLVRKFQNS | 111 | 7157 |
| B44: | PRSTPSLTTAAVLLVRKFQNS | 112 | 19499 |
| B45: | PRSTPSLTAKAVLLVRKFQNS | 113 | 7487 |
| B46: | PRSTPSLATKAVLLVRKFQNS | 114 | 7685 |
| B47: | PRSTPSATTKAVLLVRKFQNS | 115 | 8566 |

These data indicate that the sequence VLLV (SEQ ID NO:116) is a critical binding region within domain II, that domain II is preferably flanked on the amino-terminus by an amino acid sequence $R^{11}$—X—, wherein $R^{11}$ is a synthetic or naturally-occurring amino acid residue that is neutral or acidic under physiological conditions and X is any amino acid residue. More preferably, the sequence includes LTTR$^{11}$XVLLV (SEQ ID NO:117), wherein X can optionally be alaninyl. Additionally, these data indicate that the sequence VLLV (SEQ ID NO:116) is preferably flanked on the carboxyl-terminus by a pharmaceutically acceptable substituent equivalent in size to 1 to 3 amino acid residues, or more preferably, by 4 to 6 amino acid residues.

Example 3

This example provides data identifying the critical binding regions of domain III, as well as which residues within the critical binding domain are essential and/or important in the binding of human IL-6 ligand to IL-6 receptor within domain III.

These data indicate that the sequence LRYRAERS (SEQ ID NO:163) is a critical binding region within domain III, that domain III is preferably flanked on the amino-terminus by an amino acid residue $R^{21}$, wherein $R^{21}$ is a synthetic or naturally-occurring amino acid residue that has a side-chain that is neutral or basic under physiological conditions. Additionally, these data show that any of the amino acid residues of the critical binding domain can be replaced, preferably by a conservative substitution, and that the argininyl residues of the critical binding region are most important to the binding of the peptide. Moreover, while not meaning to be bound by any particular theory, it is apparent that this region of the protein exists in a pleated-sheet motif. Accordingly, substitutions of amino acid residues by structure-breaking amino acid residues, e.g., prolinyl, is less preferred.

Example 4

This example provides data identifying the critical binding regions of domain IV, as well as which residues within

| Peptide Identifier | Peptide Sequence | SEQ ID NO: | Counts/mininute bound |
|---|---|---|---|
| C1: | SSFYRLRFELRYRAERSKTFT | 118 | 14571 |
| C2: | SSFYRLRFELRYRAERSKTF | 119 | 13763 |
| C3: | SSFYRLRFELRYRAERSKT | 120 | 8210 |
| C4: | SSFYRLRFELRYRAERSK | 121 | 7619 |
| C5: | SSFYRLRFELRYRAERS | 122 | 4707 |
| C6: | SSFYRLRFELRYPAER | 123 | 2653 |
| C7: | SSEYRLRFELRYRAE | 124 | 1821 |
| C8: | SSFYRLRFELRYRA | 125 | 2509 |
| C9: | SSFYRLRFELRYR | 126 | 2173 |
| C10: | SSFYRLRFELRY | 127 | 1354 |
| C11: | SSFYRLRFELR | 128 | 1127 |
| C12: | SSEYRLRFEL | 129 | 1031 |
| C13: | SSFYRLRFE | 130 | 1019 |
| C14: | SSFYRLRF | 131 | 952 |
| C15: | SSFYRLR | 132 | 991 |
| C16: | SSFYRL | 133 | 865 |
| C17: | SSFYRLRFELRYRAERSKTFT | 118 | 15127 |
| C18: | SFYRLREELRYRAERSKTFT | 134 | 12750 |
| C19: | FYRLRFELRYRAERSKTFT | 135 | 10136 |
| C20: | YRLRFELRYRAERSKTFT | 136 | 7574 |
| C21: | RLRFELRYRAERSKTFT | 137 | 5991 |
| C22: | LRFELRYRAERSKTFT | 138 | 9610 |
| C23: | RFELRYRAERSKTFT | 139 | 5307 |
| C24: | FELRYRAERSKTFT | 140 | 5113 |
| C25: | ELRYRAERSKTFT | 141 | 2204 |
| C26: | LRYRAERSKTFT | 142 | 6382 |
| C27: | RYRAERSKTFT | 143 | 3150 |
| C28: | YRAERSKTFT | 144 | 2401 |
| C29: | RAERSKTFT | 145 | 1432 |
| C30: | AERSKTFT | 146 | 1202 |
| C31: | ERSKTFT | 147 | 1033 |
| C32: | RSKTFT | 148 | 1345 |
| C33: | SSFYRLRFELRYRAERSKTFT | 118 | 14610 |
| C34: | SSFYRLRFELRYRAERSKTFA | 149 | 16952 |
| C35: | SSFYRLRFELRYRAERSKTAT | 150 | 14809 |
| C36: | SSFYRLRFELRYRAERSKAFT | 151 | 15011 |
| C37: | SSFYRLRFELRYRAERSATFT | 152 | 7223 |
| C38: | SSFYRLRFELRYRAERAKTFT | 153 | 12308 |
| C39: | SSFYRLRFELRYRAEASKTFT | 154 | 3430 |
| C40: | SSFYRLRFELRYRAARSKTFT | 155 | 17299 |
| C41: | SSFYRLRFELRYAAERSKTFT | 156 | 6743 |
| C42: | SSFYRLRFELRARAERSKTFT | 157 | 17461 |
| C43: | SSFYRLRFELAYRAERSKTFT | 158 | 7548 |
| C44: | SSFYRLRFEARYRAERSKTFT | 159 | 14120 |
| C45: | SSFYRLRFALRYRAERSKTFT | 160 | 26802 |
| C46: | SSFYRLRAELRYRAERSKTFT | 161 | 13395 |
| C47: | SSFYRLAFELRYRAERSKTFT | 162 | 9762 | the critical binding domain are essential and/or important in the binding of human IL-6 ligand to IL-6 receptor within domain IV. In the following tabulation of data, rows D1–D10 were examined in one experiment, and rows D11–57 were examined in a separate experiment. Thus, the numerical data obtained from rows D1–10 should not be directly compared to the numerical data from rows D11–57.

a pharmaceutically acceptable substituent comparable in size to one to three amino acid residues, which are —KKT in the sequence of the human IL-6 receptor. These data also show that the sequence is preferably flanked on the amino-terminus by a pharmaceutically acceptable substituent comparable in size to one, two, three, four, five, or six or more amino acid residues. Of course, the pharmaceutically accept-

| Peptide Identifier | Peptide Sequence | SEQ ID NO: | Counts/minute bound |
|---|---|---|---|
| D1: | ATSLPVQDSSSVPLPTFLVAG | 164 | 3995 |
| D2: | VQDSSSVPLPTFLVAGGSLAF | 165 | 4521 |
| D3: | SVPLPTFLVAGGSLAFGTLLC | 166 | 19756 |
| D4: | TFLVAGGSLAFGTLLCIAIVL | 167 | 32022 |
| D5: | GGSLAFGTLLCIAIVLRFKKT | 168 | 159174 |
| D6: | FGTLLCIAIVLRFKKTWKLRA | 169 | 143540 |
| D7: | CIAIVLRFKKTWKLRALKEGK | 170 | 52538 |
| D8: | LRFKKTWKLRALKEGKTSMHP | 171 | 20399 |
| D9: | TWKLRALKEGKTSMHPPYSLG | 172 | 5530 |
| D10: | ALKEGKTSMHPPYSLGQLVPE | 173 | 4969 |
| D11: | GGSLAFGTLLCIAIVLRFKKT | 168 | 20349 |
| D12: | GGSLAFGTLLCIAIVLRFKK | 174 | 18081 |
| D13: | GGSLAFGTLLCIAIVLRFK | 175 | 16082 |
| D14: | GGSLAFGTLLCIAIVLRF | 176 | 7694 |
| D15: | GGSLAFGTLLCIAIVLR | 177 | 3948 |
| D16: | GGSLAFGTLLCIAIVL | 178 | 2456 |
| D17: | GGSLAFGTLLCIAIV | 179 | 1344 |
| D18: | GGSLAFGTLLCIAI | 180 | 1175 |
| D19: | GGSLAFGTLLCIA | 181 | 1153 |
| D20: | GGSLAFGTLLCI | 182 | 1202 |
| D21: | GGSLAFGTLLC | 183 | 1108 |
| D22: | GGSLAFGTLL | 184 | 1001 |
| D23: | GGSLAFGTL | 185 | 997 |
| D24: | GGSLAFGT | 186 | 981 |
| D25: | GGSLAFG | 187 | 952 |
| D26: | GGSLAF | 188 | 1047 |
| D27: | GGSLAFGTLLCIAIVLRFKKT | 168 | 21945 |
| D28: | GSLAFGTLLCIAIVLRFKKT | 189 | 26441 |
| D29: | SLAFGTLLCIAIVLRFKKT | 190 | 24724 |
| D30: | LAFGTLLCIAIVLRFKKT | 191 | 22737 |
| D31: | AFGTLLCIAIVLRFKKT | 192 | 24047 |
| D32: | FGTLLCIAIVLRFKKT | 193 | 21799 |
| D33: | GTLLCIAIVLRFKKT | 194 | 15730 |
| D34: | TLLCIAIVLRFKKT | 195 | 12412 |
| D35: | LLCIAIVLRFKKT | 196 | 15510 |
| D36: | LCIAIVLRFKKT | 197 | 12422 |
| D37: | CIAIVLRFKKT | 198 | 8352 |
| D38: | IAIVLRFKKT | 199 | 6800 |
| D39: | AIVLRFKKT | 200 | 4879 |
| D40: | IVLRFKKT | 201 | 4452 |
| D41: | VLRFKKT | 202 | 2551 |
| D42: | LRFKKT | 203 | 1958 |
| D43: | GGSLAFGTLLCIAIVLRFKKT | 168 | 20385 |
| D44: | GGSLAFGTLLCIAIVLRFKKA | 204 | 21366 |
| D45: | GGSLAFGTLLCIAIVLRFKAT | 205 | 28625 |
| D46: | GGSLAFGTLLCIAIVLRFAKT | 206 | 30792 |
| D47: | GGSLAFGTLLCIAIVLRAKT | 207 | 20934 |
| D48: | GGSLAFGTLLCIAIVLAFKKT | 208 | 29450 |
| D49: | GGSLAFGTLLCIAIVARFKKT | 209 | 22065 |
| D50: | GGSLAFGTLLCIAIALRFKKT | 210 | 17857 |
| D51: | GGSLAFGTLLCIAAVLRFKKT | 211 | 28461 |
| D52: | GGSLAFGTLLCAAIVLRFKKT | 212 | 27699 |
| D53: | GGSLAFGTLLAIAIVLRFKKT | 213 | 34879 |
| D54: | GGSLAFGTLACIAIVLRFKKT | 214 | 22037 |
| D55: | GGSLAFGTALCIAIVLRFKKT | 215 | 22123 |
| D56: | GGSLAFGALLCIAIVLRFKKT | 216 | 22973 |
| D57: | GGSLAFATLLCIAIVLRFKKT | 217 | 22324 |

These data indicate that the sequence IAIVLRF (SEQ ID NO:218) is a critical binding region within domain IV, that this critical binding domain is preferably flanked on the carboxyl-terminus by one or two lysinyl residues, or at least able substituents could be synthetic or naturally-occurring amino acid residues. Moreover, the data show that any one of the amino acid residues can be replaced by an alaninyl residue, resulting in an increase in affinity for IL-6. One skilled in the art will also appreciate that multiple (e.g., two or three) substitutions can be made in the critical binding region, and that when multiple replacements or substitutions are made, then the substitutions are preferably conservatively selected. Additionally, the skilled artisan will note that the critical amino acid sequence IAIVLRF (SEQ ID NO:218) resides in an extended region that has high affinity for the IL-6 ligand and that four of the seven amino acid residues of this critical region can be found at either the amino- or carboxyl terminus of a polypeptide comprising the sequence.

Example 5

This example employs essentially the same techniques as Examples 1–4 except that fragments of the β-chain of the IL-6 receptor are used. As is known in the art, the β-chain is shared by multiple receptors. Thus, the identified fragments here are effective inhibitors of a multiplicity of binding reactions in addition to the IL-6 ligand:IL-6 receptor interaction.

| Peptide Identifier | Peptide Sequence | SEQ ID NO: | Counts/ minute bound |
|---|---|---|---|
| E1: | MLTLQTWVVQALFIFLTTESTGEL | 219 | 3365 |
| E2: | ALFIFLTTESTGELLDPCGYISPE | 220 | 1531 |
| E3: | TGELLDPCGYISPESPVVQLHSNF | 221 | 1300 |
| E4: | ISPESPVVQLHSNFTAVCVLKEKC | 222 | 1499 |
| E5: | HSNFTAVCVLKEKCMDYFHVNANY | 223 | 1292 |
| E6: | KEKCMDYFHVNANYIVWKTNHFTI | 224 | 1443 |
| E7: | NANYIVWKTNHFTIPKEQYTIINR | 225 | 1327 |
| E8: | HFTIPKEQYTIINRTASSVTFTDI | 226 | 1143 |
| E9: | IINRTASSVTFTDIASLNIQLTCN | 227 | 1628 |
| E10: | FTDIASLNIQLTCNILTFGQLEQN | 228 | 3376 |
| E11: | LTCNILTFGQLEQNVYGITIISGL | 229 | 1816 |
| E12: | LEQNVYGITIISGLPPEKPKNLSC | 230 | 1669 |
| E13: | ISGLPPEKPKNLSCIVNEGKKMRC | 231 | 1202 |
| E14: | NLSCIVNEGKKMRCEWDGGRETHL | 232 | 1171 |
| E15: | KMRCEWDGGRETHLETNFTLKSEW | 233 | 1573 |
| E16: | ETHLETNFTLKSEWATHKFADCKA | 234 | 1035 |
| E17: | KSEWATHKFADCKAKRDTPTSCTV | 235 | 1409 |
| E18: | DCKAKRDTPTSCTVDYSTVYFVNI | 236 | 1548 |
| E19: | SCTVDYSTVYFVNIEVWVEAENAL | 237 | 3317 |
| E20: | FVNIEVWVEAENALGKVTSDHINF | 238 | 1413 |
| E21: | ENALGKVTSDHINFDPVYKVKPNP | 239 | 1122 |
| E22: | HINFDPVYKVKPNPPHNLSVINSE | 240 | 1728 |
| E23: | KPNPPHNLSVINSEELSSILKLTW | 241 | 1414 |
| E24: | INSEELSSILKLTWTNPSIKSVII | 242 | 1007 |
| E25: | KLTWTNPSIKSVIILKYNIQYRTK | 243 | 10331 |
| E26: | SVIILKYNIQYRTKDASTWSQIPP | 244 | 2832 |
| E27: | YRTKDASTWSQIPPEDTASTRSSF | 245 | 1162 |
| E28: | QIPPEDTASTRSSFTVQDLKPFTE | 246 | 1202 |
| E29: | RSSFTVQDLKPFTEYVFRIRCMKE | 247 | 1318 |
| E30: | PFTEYVFRIRCMKEDGKGYWSDWS | 248 | 1263 |
| E31: | CMKEDGKGYWSDWSEEASGITYED | 249 | 1732 |
| E32: | SDWSEEASGITYEDRPSKAPSFWY | 250 | 1161 |
| E33: | TYEDRPSKAPSFWYKIDPSHTQGY | 251 | 1215 |
| E34: | SFWYKIDPSHTQGYRTVQLVWKTL | 252 | 1145 |
| E35: | TQGYRTVQLVWKTLPPFEANGKIL | 253 | 1169 |
| E36: | WKTLPPFEANGKILDYEVTLTRWK | 254 | 1465 |
| E37: | GKILDYEVTLTRWKSHLQNYTVNA | 255 | 1791 |
| E38: | TRWKSHLQNYTVNATKLTVNLTND | 256 | 3652 |
| E39: | TVNATKLTVNLTNDRYLATLTVRN | 257 | 4360 |
| E40: | LTNDRYLATLTVRNLVGKSDAAVL | 258 | 4802 |
| E41: | TVRNLVGKSDAAVLTIPACDFQAT | 259 | 1104 |
| E42: | AAVLTIPACDFQATHPVMDLKAFP | 260 | 1121 |
| E43: | FQATHPVMDLKAFPKDNMLWVEWT | 261 | 1299 |
| E44: | KAFPKDNMLWVEWTTPRESVKKYI | 262 | 1175 |
| E45: | VEWTTPRESVKKYILEWCVLSDKA | 263 | 1389 |
| E46: | KKYILEWCVLSDKAPCITDWQQED | 264 | 1712 |
| E47: | SDKAPCITDWQQEDGTVHRTYLRG | 265 | 2079 |
| E48: | QQEDGTVHRTYLRGNLAESKCYLI | 266 | 1082 |
| E49: | YLRGNLAESKCYLITVTPVYADGP | 267 | 1541 |
| E50: | CYLITVTPVYADGPGSPESIKAYL | 268 | 1259 |
| E51: | ADGPGSPESIKAYLKQAPPSKGPT | 269 | 1194 |
| E52: | KAYLKQAPPSKGPTVRTKKVGKNE | 270 | 1816 |
| E53: | KGPTVRTKKVGKNEAVLEWDQLPV | 271 | 1636 |
| E54: | GKNEAVLEWDQLPVDVQNGFIRNY | 272 | 1307 |
| E55: | QLPVDVQNGFIRNYTIFYRTIIGN | 274 | 4355 |
| E56: | IRNYTIFYRTIIGNETAVNVDSSH | 275 | 1635 |
| E57: | IIGNETAVNVDSSHTEYTLSSLTS | 276 | 1232 |
| E58: | DSSHTEYTLSSLTSDTLYMVRMAA | 277 | 1353 |
| E59: | SLTSDTLYMVRMAAYTDEGGKDGP | 278 | 1270 |
| E60: | RMAAYTDEGGKDGPEFTFTTPKFA | 279 | 1447 |
| E61: | KDGPEFTFTTPKFAQGEIEAIVVP | 280 | 1393 |
| E62: | PKFAQGEIEAIVVPVCLAFLLTTL | 281 | 2794 |
| E63: | IVVPVCLAFLLTTLLGVLFCFNKR | 282 | 4519 |
| E64: | LTTLLGVLFCFNKRDLIKKHIWPN | 283 | 4501 |
| E65: | FNKRDLIKKHIWPNVPDPSKSHIA | 284 | 5741 |
| E66: | IWPNVPDPSKSHIAQWSPHTPPRH | 285 | 1203 |
| E67: | SHIAQWSPHTPPRHNFNSKDQMYS | 286 | 1199 |
| E68: | PPRHNFNSKDQMYSDGNFTDVSVV | 287 | 1231 |
| E69: | QMYSDGNFTDVSVVEIEANDKKPF | 288 | 1194 |
| E70: | VSVVEIEANDKKPFPEDLKSLDLF | 289 | 1305 |
| E71: | KKPFPEDLKSLDLFKKEKINTEGH | 290 | 2694 |
| E72: | LDLFKKEKINTEGHSSGIGGSSCM | 291 | 1443 |
| E73: | TEGHSSGIGGSSCMSSSRPSISSS | 292 | 1060 |
| E74: | SSCMSSSRPSISSSDENESSQNTS | 293 | 1131 |
| E75: | ISSSDENESSQNTSSTVQYSTVVH | 294 | 1118 |
| E76: | QNTSSTVQYSTVVHSGYRHQVPSV | 295 | 1197 |
| E77: | TVVHSGYRHQVPSVQVFSRSESTQ | 296 | 1247 |
| E78: | VPSVQVFSRSESTQPLLDSEERPE | 297 | 1229 |
| E79: | ESTQPLLDSEERPEDLQLVDHVDG | 298 | 1384 |
| E80: | ERPEDLQLVDHVDGGDGILPRQQY | 299 | 1214 |
| E81: | HVDGGDGILPRQQYFKQNCSQHES | 300 | 1097 |
| E82: | RQQYFKQNCSQHESSPDISHFERS | 301 | 1087 |
| E83: | QHESSPDISHFERSKQVSSVNEED | 301 | 1250 |
| E84: | FERSKQVSSVNEEDFVRLKQQISD | 302 | 1015 |
| E85: | NEEDFVRLKQQISDHISQSCGSGQ | 303 | 1113 |
| E86: | QISDHISQSCGSGQMKMFQEVSAA | 304 | 1239 |
| E87: | GSGQMKMFQEVSAADAFGPGTEGQ | 305 | 1001 |
| E88: | VSAADAFGPGTEGQVERFETVGME | 306 | 1091 |
| E89: | TEGQVERFETVGMEAATDEGMPKS | 307 | 1131 |
| E90: | VGMEAATDEGMPKSYLPQTVRQGG | 308 | 1385 |
| E91: | MPKSYLPQTVRQGGYMPQ | 309 | 1226 |

These data demonstrate that the sequence SVIILKYNIQY (SEQ ID NO:6) is sufficient to bind to IL-6 ligand; however, better binding can be obtained by a sequence comprising the sequence PSIKSVIILKYNIQY (SEQ ID NO:14) and the sequence can optionally comprise either WTNPSIKSVI-ILKYNIQY (SEQ ID NO:15) or even KLTWTNPSIKSVI-ILKYNIQY (SEQ ID NO:16).

These data also indicate that the sequence TRWK-SHLQNYTVNATKLTVNLTNDRY-LATLTVRNLVGKSDAAVL (SEQ ID NO:7) comprises a multiplicity of subsequences, each of which can bind with IL-6 ligand. Similarly, QLPVDVQNGFIRNYTIFYRTIIGN (SEQ ID NO:8) comprises a multiplicity of subsequences, each of which can bind with IL-6 ligand. Additionally, the sequence IVVPVCLAFLLTTLLGVLFCFNKRD-LIKKHIWPNVPDPSKSHIA (SEQ ID NO:9)comprises a multiplicity of subsequences, each of which can bind with IL-6 ligand.

For example, one skilled in the art will appreciate that any segment of the foregoing sequences comprising about six, twelve, eighteen, or twenty-four amino acid residues is expected to bind with IL-6 ligand. Moreover, these data indicate to the skilled artisan that a multiplicity of amino acid substitutions, particularly conservative amino acid substitutions, within any of the above-described polypeptides can yield additional polypeptides having a substantial ability to bind with IL-6 ligand and to inhibit the binding of IL-6 ligand to IL-6 receptor and thereby inhibit IL-6 signaling under physiological conditions.

All publications cited herein are hereby incorporated by reference to the same extent as if each publication were individually and specifically indicated to be incorporated by reference and were set forth in its entirety herein.

While this invention has been described with an emphasis upon preferred embodiments, it will be obvious to those of ordinary skill in the art that variations of the preferred polypeptides, nucleic acids, compositions and methods, and the like can be used and that it is intended that the invention can be practiced otherwise than as specifically described herein. Accordingly, this invention includes all modifications encompassed within the spirit and scope of the invention as defined by the following claims.

What is claimed is:

1. An isolated polypeptide consisting of a fragment of the IL-6 receptor, wherein said fragment comprises SEQ ID NO:23 or SEQ ID NO:25, wherein said polypeptide inhibits the binding of IL-6 ligand with the IL-6 receptor under physiological conditions and wherein said fragment is not more than 200 contiguous amino acids.

* * * * *

UNITED STATES PATENT AND TRADEMARK OFFICE
CERTIFICATE OF CORRECTION

PATENT NO.    : 6,664,374 B1
DATED         : December 16, 2003
INVENTOR(S)   : Saxinger It is certified that error appears in the above-identified patent and that said Letters Patent is hereby corrected as shown below:

Column 153,
Line 3, "SEQ ID NO:25" should read -- SEQ ID NO:24 --.

Signed and Sealed this

Sixth Day of April, 2004

JON W. DUDAS
*Acting Director of the United States Patent and Trademark Office*

SEQUENCE LISTING

```
<160> NUMBER OF SEQ ID NOS:  309

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: synthetic
<221> NAME/KEY: PEPTIDE
<222> LOCATION: (1)..(6)
<223> OTHER INFORMATION: "Xaa" is a variable amino acid.

<400> SEQUENCE: 1

Xaa Xaa Xaa Xaa Xaa Xaa
 1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: synthetic
<221> NAME/KEY: PEPTIDE
<222> LOCATION: (1)..(6)
<223> OTHER INFORMATION: "Xaa" is a variable amino acid.

<400> SEQUENCE: 2

Xaa Xaa Xaa Xaa Xaa Xaa
 1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: synthetic
<221> NAME/KEY: PEPTIDE
<222> LOCATION: (1)
<223> OTHER INFORMATION: "Xaa" is a variable amino acid.
<221> NAME/KEY: PEPTIDE
<222> LOCATION: (3)..(4)
<223> OTHER INFORMATION: "Xaa" is a variable amino acid.

<400> SEQUENCE: 3

Xaa Val Xaa Xaa Val
 1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: synthetic
<221> NAME/KEY: PEPTIDE
<222> LOCATION: (1)..(8)
<223> OTHER INFORMATION: "Xaa" is a variable amino acid.
```

-continued

```
<400> SEQUENCE: 4

Xaa Xaa Xaa Xaa Xaa Xaa Xaa Xaa
 1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: synthetic
<221> NAME/KEY: PEPTIDE
<222> LOCATION: (1)..(7)
<223> OTHER INFORMATION: "Xaa" is a variable amino acid.

<400> SEQUENCE: 5

Xaa Xaa Xaa Xaa Xaa Xaa Xaa
 1               5

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Binding
      peptide

<400> SEQUENCE: 6

Ser Val Ile Ile Leu Lys Tyr Asn Ile Gln Tyr
 1               5                  10

<210> SEQ ID NO 7
<211> LENGTH: 44
<212> TYPE: PRT
<213> ORGANISM: Artificial Sequence
<220> FEATURE:
<223> OTHER INFORMATION: Description of Artificial Sequence: Binding
      peptide

<400> SEQUENCE: 7

Thr Arg Trp Lys Ser His Leu Gln Asn Tyr Thr Val Asn Ala Thr Lys
 1               5                  10                  15

Leu Thr Val Asn Leu Thr Asn Asp Arg Tyr Leu Ala Thr Leu Thr Val
             20                  25                  30

Arg Asn Leu Val Gly Lys Ser Asp Ala Ala Val Leu
         35                  40

<210> SEQ ID NO 8
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 8

Gln Leu Pro Val Asp Val Gln Asn Gly Phe Ile Arg Asn Tyr Thr Ile
 1               5                  10                  15

Phe Tyr Arg Thr Ile Ile Gly Asn
             20

<210> SEQ ID NO 9
<211> LENGTH: 44
<212> TYPE: PRT
<213> ORGANISM: Artificial Sequence
<220> FEATURE:
<223> OTHER INFORMATION: Description of Artificial Sequence: Binding
``` peptide

<400> SEQUENCE: 9

Ile Val Val Pro Val Cys Leu Ala Phe Leu Leu Thr Thr Leu Leu Gly
1               5                   10                  15

Val Leu Phe Cys Phe Asn Lys Arg Asp Leu Ile Lys Lys His Ile Trp
            20                  25                  30

Pro Asn Val Pro Asp Pro Ser Lys Ser His Ile Ala
        35                  40

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Binding
      peptide

<400> SEQUENCE: 10

Arg Arg Leu Leu Leu Arg
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: synthetic
<221> NAME/KEY: PEPTIDE
<222> LOCATION: (2)
<223> OTHER INFORMATION: "Xaa" is a variable amino acid.

<400> SEQUENCE: 11

Arg Xaa Val Leu Leu Val
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Binding
      peptide

<400> SEQUENCE: 12

Leu Arg Tyr Arg Ala Glu Arg Ser
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Binding
      peptide

<400> SEQUENCE: 13

Ile Ala Ile Val Leu Arg Phe
1               5

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Binding
      peptide

```
<400> SEQUENCE: 14

Pro Ser Ile Lys Ser Val Ile Ile Leu Lys Tyr Asn Ile Gln Tyr
 1               5                  10                  15

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: Binding
      peptide

<400> SEQUENCE: 15

Trp Thr Asn Pro Ser Ile Lys Ser Val Ile Ile Leu Lys Tyr Asn Ile
 1               5                  10                  15

Gln Tyr

<210> SEQ ID NO 16
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 16

Lys Leu Thr Trp Thr Asn Pro Ser Ile Lys Ser Val Ile Ile Leu Lys
 1               5                  10                  15

Tyr Asn Ile Gln Tyr
            20

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: synthetic
<221> NAME/KEY: PEPTIDE
<222> LOCATION: (1)..(6)
<223> OTHER INFORMATION: "Xaa" is a variable amino acid.

<400> SEQUENCE: 17

Xaa Xaa Xaa Xaa Xaa Xaa
 1               5

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Binding
      peptide

<400> SEQUENCE: 18

Val Leu Leu Val
 1

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Binding
      peptide

<400> SEQUENCE: 19
```

```
Thr Lys Ala Val Leu Leu Val Arg Phe
  1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Binding
      peptide

<400> SEQUENCE: 20

Leu Arg Ala Glu Arg Ser
  1               5

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Binding
      peptide

<400> SEQUENCE: 21

Phe Glu Leu Arg Ala Glu Arg Ser Lys Thr
  1               5                  10

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Binding
      peptide

<400> SEQUENCE: 22

Ile Ala Ile Val Leu Arg Phe
  1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Binding
      peptide

<400> SEQUENCE: 23

Ile Ala Ile Val Leu Arg Phe Lys
  1               5

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
<221> NAME/KEY: PEPTIDE
<222> LOCATION: (9)..(10)
<223> OTHER INFORMATION: "Xaa" is a variable amino acid.

<400> SEQUENCE: 24

Ile Ala Ile Val Leu Arg Phe Lys Xaa Xaa
  1               5                  10

<210> SEQ ID NO 25
<211> LENGTH: 11
```

```
<212> TYPE: PRT
<213> ORGANISM: Artificial Sequence
<220> FEATURE:
<223> OTHER INFORMATION: Description of Artificial Sequence: Binding
      peptide

<400> SEQUENCE: 25

Leu Leu Cys Ile Ala Ile Val Leu Arg Phe Lys
  1               5                  10

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Binding
      peptide

<400> SEQUENCE: 26

Phe Gly Thr Leu Leu Cys Ile Ala Ile Val Leu Arg Phe Lys Lys Thr
  1               5                  10                  15

<210> SEQ ID NO 27
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 27

Ala Ala Gly Ser His Pro Ser Arg Trp Ala Gly Met Gly Arg Arg Leu
  1               5                  10                  15

Leu Leu Arg Ser Val
             20

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence: Binding
      peptide

<400> SEQUENCE: 28

Ala Ala Gly Ser His Pro Ser Arg Trp Ala Gly Met Gly Arg Arg Leu
  1               5                  10                  15

Leu Leu Arg Ser
             20

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Binding
      peptide

<400> SEQUENCE: 29

Ala Ala Gly Ser His Pro Ser Arg Trp Ala Gly Met Gly Arg Arg Leu
  1               5                  10                  15

Leu Leu Arg

<210> SEQ ID NO 30
<211> LENGTH: 18
<212> TYPE: PRT
```

```
<213> ORGANISM: Artificial Sequence
<220> FEATURE:
<223> OTHER INFORMATION: Description of Artificial Sequence: Binding
      peptide

<400> SEQUENCE: 30

Ala Ala Gly Ser His Pro Ser Arg Trp Ala Gly Met Gly Arg Arg Leu
  1               5                  10                  15

Leu Leu

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Binding
      peptide

<400> SEQUENCE: 31

Ala Ala Gly Ser His Pro Ser Arg Trp Ala Gly Met Gly Arg Arg Leu
  1               5                  10                  15

Leu

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Binding
      peptide

<400> SEQUENCE: 32

Ala Ala Gly Ser His Pro Ser Arg Trp Ala Gly Met Gly Arg Arg Leu
  1               5                  10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Binding
      peptide

<400> SEQUENCE: 33

Ala Ala Gly Ser His Pro Ser Arg Trp Ala Gly Met Gly Arg Arg
  1               5                  10                  15

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Binding
      peptide

<400> SEQUENCE: 34

Ala Ala Gly Ser His Pro Ser Arg Trp Ala Gly Met Gly Arg
  1               5                  10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Binding
      peptide
```

```
<400> SEQUENCE: 35

Ala Ala Gly Ser His Pro Ser Arg Trp Ala Gly Met Gly
 1               5                  10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Binding
      peptide

<400> SEQUENCE: 36

Ala Ala Gly Ser His Pro Ser Arg Trp Ala Gly Met
 1               5                  10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Binding
      peptide

<400> SEQUENCE: 37

Ala Ala Gly Ser His Pro Ser Arg Trp Ala Gly
 1               5                  10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Binding
      peptide

<400> SEQUENCE: 38

Ala Ala Gly Ser His Pro Ser Arg Trp Ala
 1               5                  10

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Binding
      peptide

<400> SEQUENCE: 39

Ala Ala Gly Ser His Pro Ser Arg Trp
 1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Binding
      peptide

<400> SEQUENCE: 40

Ala Ala Gly Ser His Pro Ser Arg
 1               5

<210> SEQ ID NO 41
<211> LENGTH: 7
<212> TYPE: PRT
```

```
<213> ORGANISM: Artificial Sequence
<220> FEATURE:
<223> OTHER INFORMATION: Description of Artificial Sequence: Binding
      peptide

<400> SEQUENCE: 41

Ala Ala Gly Ser His Pro Ser
 1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Binding
      peptide

<400> SEQUENCE: 42

Ala Ala Gly Ser His Pro
 1               5

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 43

Ala Ala Gly Ser His Pro Ser Arg Trp Ala Gly Met Gly Arg Arg Leu
 1               5                  10                  15

Leu Leu Arg Ser Val
            20

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Binding
      peptide

<400> SEQUENCE: 44

Gly Ser His Pro Ser Arg Trp Ala Gly Met Gly Arg Arg Leu Leu Leu
 1               5                  10                  15

Arg Ser Val

<210> SEQ ID NO 45
<211> LENGTH: 18
<212> TYPE: PRT
<213> ORGANISM: Artificial Sequence
<220> FEATURE:
<223> OTHER INFORMATION: Description of Artificial Sequence: Binding
      peptide

<400> SEQUENCE: 45

Ser His Pro Ser Arg Trp Ala Gly Met Gly Arg Arg Leu Leu Leu Arg
 1               5                  10                  15

Ser Val

<210> SEQ ID NO 46
<211> LENGTH: 17
<212> TYPE: PRT
<213> ORGANISM: Artificial Sequence
<220> FEATURE:
```

-continued

```
<223> OTHER INFORMATION: Description of Artificial Sequence: Binding
      peptide

<400> SEQUENCE: 46

His Pro Ser Arg Trp Ala Gly Met Gly Arg Arg Leu Leu Leu Arg Ser
 1               5                  10                  15

Val

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Binding
      peptide

<400> SEQUENCE: 47

Pro Ser Arg Trp Ala Gly Met Gly Arg Arg Leu Leu Leu Arg Ser Val
 1               5                  10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Binding
      peptide

<400> SEQUENCE: 48

Ser Arg Trp Ala Gly Met Gly Arg Arg Leu Leu Leu Arg Ser Val
 1               5                  10                  15

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Binding
      peptide

<400> SEQUENCE: 49

Arg Trp Ala Gly Met Gly Arg Arg Leu Leu Leu Arg Ser Val
 1               5                  10

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Binding
      peptide

<400> SEQUENCE: 50

Trp Ala Gly Met Gly Arg Arg Leu Leu Leu Arg Ser Val
 1               5                  10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Binding
      peptide

<400> SEQUENCE: 51

Ala Gly Met Gly Arg Arg Leu Leu Leu Arg Ser Val
 1               5                  10
```

```
<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Binding
      peptide

<400> SEQUENCE: 52

Gly Met Gly Arg Arg Leu Leu Leu Arg Ser Val
 1               5                  10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Binding
      peptide

<400> SEQUENCE: 53

Met Gly Arg Arg Leu Leu Leu Arg Ser Val
 1               5                  10

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Binding
      peptide

<400> SEQUENCE: 54

Gly Arg Arg Leu Leu Leu Arg Ser Val
 1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Binding
      peptide

<400> SEQUENCE: 55

Arg Arg Leu Leu Leu Arg Ser Val
 1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Binding
      peptide

<400> SEQUENCE: 56

Arg Leu Leu Leu Arg Ser Val
 1               5

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Binding
      peptide
```

```
<400> SEQUENCE: 57

Leu Leu Leu Arg Ser Val
 1               5

<210> SEQ ID NO 58
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 58

Ala Ala Gly Ser His Pro Ser Arg Trp Ala Gly Met Gly Arg Arg Leu
 1               5                  10                  15

Leu Leu Arg Ser Ala
            20

<210> SEQ ID NO 59
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 59

Ala Ala Gly Ser His Pro Ser Arg Trp Ala Gly Met Gly Arg Arg Leu
 1               5                  10                  15

Leu Leu Arg Ala Val
            20

<210> SEQ ID NO 60
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 60

Ala Ala Gly Ser His Pro Ser Arg Trp Ala Gly Met Gly Arg Arg Leu
 1               5                  10                  15

Leu Leu Ala Ser Val
            20

<210> SEQ ID NO 61
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 61

Ala Ala Gly Ser His Pro Ser Arg Trp Ala Gly Met Gly Arg Arg Leu
 1               5                  10                  15

Leu Ala Arg Ser Val
            20

<210> SEQ ID NO 62
<211> LENGTH: 21
<212> TYPE: PRT
<213> ORGANISM: Artificial Sequence
```

```
<220> FEATURE:
<223> OTHER INFORMATION: Description of Artificial Sequence: Binding
      peptide

<400> SEQUENCE: 62

Ala Ala Gly Ser His Pro Ser Arg Trp Ala Gly Met Gly Arg Arg Leu
 1               5                  10                  15

Ala Leu Arg Ser Val
            20

<210> SEQ ID NO 63
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 63

Ala Ala Gly Ser His Pro Ser Arg Trp Ala Gly Met Gly Arg Arg Ala
 1               5                  10                  15

Leu Leu Arg Ser Val
            20

<210> SEQ ID NO 64
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 64

Ala Ala Gly Ser His Pro Ser Arg Trp Ala Gly Met Gly Arg Ala Leu
 1               5                  10                  15

Leu Leu Arg Ser Val
            20

<210> SEQ ID NO 65
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 65

Ala Ala Gly Ser His Pro Ser Arg Trp Ala Gly Met Gly Ala Arg Leu
 1               5                  10                  15

Leu Leu Arg Ser Val
            20

<210> SEQ ID NO 66
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 66

Ala Ala Gly Ser His Pro Ser Arg Trp Ala Gly Met Ala Arg Arg Leu
 1               5                  10                  15

Leu Leu Arg Ser Val
            20
```

```
<210> SEQ ID NO 67
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 67

Ala Ala Gly Ser His Pro Ser Arg Trp Ala Gly Ala Gly Arg Arg Leu
 1               5                  10                  15

Leu Leu Arg Ser Val
            20

<210> SEQ ID NO 68
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 68

Ala Ala Gly Ser His Pro Ser Arg Trp Ala Ala Met Gly Arg Arg Leu
 1               5                  10                  15

Leu Leu Arg Ser Val
            20

<210> SEQ ID NO 69
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 69

Ala Ala Gly Ser His Pro Ser Arg Ala Ala Gly Met Gly Arg Arg Leu
 1               5                  10                  15

Leu Leu Arg Ser Val
            20

<210> SEQ ID NO 70
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 70

Ala Ala Gly Ser His Pro Ser Ala Trp Ala Gly Met Gly Arg Arg Leu
 1               5                  10                  15

Leu Leu Arg Ser Val
            20

<210> SEQ ID NO 71
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 71
```

Ala Ala Gly Ser His Pro Ala Arg Trp Ala Gly Met Gly Arg Arg Leu
 1               5                  10                 15

Leu Leu Arg Ser Val
            20

<210> SEQ ID NO 72
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 72

Pro Arg Ser Thr Pro Ser Leu Thr Thr Lys Ala Val Leu Leu Val Arg
 1               5                  10                 15

Lys Phe Gln Asn Ser
            20

<210> SEQ ID NO 73
<211> LENGTH: 20
<212> TYPE: PRT
<213> ORGANISM: Artificial Sequence
<220> FEATURE:
<223> OTHER INFORMATION: Description of Artificial Sequence: Binding
      peptide

<400> SEQUENCE: 73

Pro Arg Ser Thr Pro Ser Leu Thr Thr Lys Ala Val Leu Leu Val Arg
 1               5                  10                 15

Lys Phe Gln Asn
            20

<210> SEQ ID NO 74
<211> LENGTH: 19
<212> TYPE: PRT
<213> ORGANISM: Artificial Sequence
<220> FEATURE:
<223> OTHER INFORMATION: Description of Artificial Sequence: Binding
      peptide

<400> SEQUENCE: 74

Pro Arg Ser Thr Pro Ser Leu Thr Thr Lys Ala Val Leu Leu Val Arg
 1               5                  10                 15

Lys Phe Gln

<210> SEQ ID NO 75
<211> LENGTH: 18
<212> TYPE: PRT
<213> ORGANISM: Artificial Sequence
<220> FEATURE:
<223> OTHER INFORMATION: Description of Artificial Sequence: Binding
      peptide

<400> SEQUENCE: 75

Pro Arg Ser Thr Pro Ser Leu Thr Thr Lys Ala Val Leu Leu Val Arg
 1               5                  10                 15

Lys Phe

<210> SEQ ID NO 76
<211> LENGTH: 17
<212> TYPE: PRT
<213> ORGANISM: Artificial Sequence
<220> FEATURE:

-continued

<223> OTHER INFORMATION: Description of Artificial Sequence: Binding
      peptide

<400> SEQUENCE: 76

Pro Arg Ser Thr Pro Ser Leu Thr Thr Lys Ala Val Leu Leu Val Arg
 1               5                   10                  15

Lys

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Binding
      peptide

<400> SEQUENCE: 77

Pro Arg Ser Thr Pro Ser Leu Thr Thr Lys Ala Val Leu Leu Val Arg
 1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Binding
      peptide

<400> SEQUENCE: 78

Pro Arg Ser Thr Pro Ser Leu Thr Thr Lys Ala Val Leu Leu Val
 1               5                   10                  15

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Binding
      peptide

<400> SEQUENCE: 79

Pro Arg Ser Thr Pro Ser Leu Thr Thr Lys Ala Val Leu Leu
 1               5                   10

<210> SEQ ID NO 80
<211> LENGTH: 13
<212> TYPE: PRT
<213> ORGANISM: Artificial Sequence
<220> FEATURE:
<223> OTHER INFORMATION: Description of Artificial Sequence: Binding
      peptide

<400> SEQUENCE: 80

Pro Arg Ser Thr Pro Ser Leu Thr Thr Lys Ala Val Leu
 1               5                   10

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Binding
      peptide

<400> SEQUENCE: 81

Pro Arg Ser Thr Pro Ser Leu Thr Thr Lys Ala Val
 1               5                   10

```
<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Binding
      peptide

<400> SEQUENCE: 82

Pro Arg Ser Thr Pro Ser Leu Thr Thr Lys Ala
 1               5                  10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Binding
      peptide

<400> SEQUENCE: 83

Pro Arg Ser Thr Pro Ser Leu Thr Thr Lys
 1               5                  10

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Binding
      peptide

<400> SEQUENCE: 84

Pro Arg Ser Thr Pro Ser Leu Thr Thr
 1               5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Binding
      peptide

<400> SEQUENCE: 85

Pro Arg Ser Thr Pro Ser Leu Thr
 1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Binding
      peptide

<400> SEQUENCE: 86

Pro Arg Ser Thr Pro Ser Leu
 1               5

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: Binding
      peptide
```

<400> SEQUENCE: 87

Pro Arg Ser Thr Pro Ser
 1               5

<210> SEQ ID NO 88
<211> LENGTH: 20
<212> TYPE: PRT
<213> ORGANISM: Artificial Sequence
<220> FEATURE:
<223> OTHER INFORMATION: Description of Artificial Sequence: Binding
      peptide

<400> SEQUENCE: 88

Arg Ser Thr Pro Ser Leu Thr Thr Lys Ala Val Leu Leu Val Arg Lys
 1               5                  10                  15

Phe Gln Asn Ser
             20

<210> SEQ ID NO 89
<211> LENGTH: 19
<212> TYPE: PRT
<213> ORGANISM: Artificial Sequence
<220> FEATURE:
<223> OTHER INFORMATION: Description of Artificial Sequence: Binding
      peptide

<400> SEQUENCE: 89

Ser Thr Pro Ser Leu Thr Thr Lys Ala Val Leu Leu Val Arg Lys Phe
 1               5                  10                  15

Gln Asn Ser

<210> SEQ ID NO 90
<211> LENGTH: 18
<212> TYPE: PRT
<213> ORGANISM: Artificial Sequence
<220> FEATURE:
<223> OTHER INFORMATION: Description of Artificial Sequence: Binding
      peptide

<400> SEQUENCE: 90

Thr Pro Ser Leu Thr Thr Lys Ala Val Leu Leu Val Arg Lys Phe Gln
 1               5                  10                  15

Asn Ser

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Binding
      peptide

<400> SEQUENCE: 91

Pro Ser Leu Thr Thr Lys Ala Val Leu Leu Val Arg Lys Phe Gln Asn
 1               5                  10                  15

Ser

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Binding
      peptide

```
<400> SEQUENCE: 92

Ser Leu Thr Thr Lys Ala Val Leu Leu Val Arg Lys Phe Gln Asn Ser
  1               5                  10                  15

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Binding
      peptide

<400> SEQUENCE: 93

Leu Thr Thr Lys Ala Val Leu Leu Val Arg Lys Phe Gln Asn Ser
  1               5                  10                  15

<210> SEQ ID NO 94
<211> LENGTH: 14
<212> TYPE: PRT
<213> ORGANISM: Artificial Sequence
<220> FEATURE:
<223> OTHER INFORMATION: Description of Artificial Sequence: Binding
      peptide

<400> SEQUENCE: 94

Thr Thr Lys Ala Val Leu Leu Val Arg Lys Phe Gln Asn Ser
  1               5                  10

<210> SEQ ID NO 95
<211> LENGTH: 13
<212> TYPE: PRT
<213> ORGANISM: Artificial Sequence
<220> FEATURE:
<223> OTHER INFORMATION: Description of Artificial Sequence: Binding
      peptide

<400> SEQUENCE: 95

Thr Lys Ala Val Leu Leu Val Arg Lys Phe Gln Asn Ser
  1               5                  10

<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: Binding
      peptide

<400> SEQUENCE: 96

Lys Ala Val Leu Leu Val Arg Lys Phe Gln Asn Ser
  1               5                  10

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Binding
      peptide

<400> SEQUENCE: 97

Ala Val Leu Leu Val Arg Lys Phe Gln Asn Ser
  1               5                  10

<210> SEQ ID NO 98
<211> LENGTH: 10
```

<212> TYPE: PRT
<213> ORGANISM: Artificial Sequence
<220> FEATURE:
<223> OTHER INFORMATION: Description of Artificial Sequence: Binding
      peptide

<400> SEQUENCE: 98

Val Leu Leu Val Arg Lys Phe Gln Asn Ser
 1               5                  10

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Binding
      peptide

<400> SEQUENCE: 99

Leu Leu Val Arg Lys Phe Gln Asn Ser
 1               5

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Binding
      peptide

<400> SEQUENCE: 100

Leu Val Arg Lys Phe Gln Asn Ser
 1               5

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Binding
      peptide

<400> SEQUENCE: 101

Val Arg Lys Phe Gln Asn Ser
 1               5

<210> SEQ ID NO 102
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 102

Pro Arg Ser Thr Pro Ser Leu Thr Thr Lys Ala Val Leu Leu Val Arg
 1               5                  10                  15

Lys Phe Gln Asn Ala
            20

<210> SEQ ID NO 103
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 103

Pro Arg Ser Thr Pro Ser Leu Thr Thr Lys Ala Val Leu Leu Val Arg
1               5                   10                  15

Lys Phe Gln Ala Ser
            20

<210> SEQ ID NO 104
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 104

Pro Arg Ser Thr Pro Ser Leu Thr Thr Lys Ala Val Leu Leu Val Arg
1               5                   10                  15

Lys Phe Ala Asn Ser
            20

<210> SEQ ID NO 105
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 105

Pro Arg Ser Thr Pro Ser Leu Thr Thr Lys Ala Val Leu Leu Val Arg
1               5                   10                  15

Lys Ala Gln Asn Ser
            20

<210> SEQ ID NO 106
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 106

Pro Arg Ser Thr Pro Ser Leu Thr Thr Lys Ala Val Leu Leu Val Arg
1               5                   10                  15

Ala Phe Gln Asn Ser
            20

<210> SEQ ID NO 107
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 107

Pro Arg Ser Thr Pro Ser Leu Thr Thr Lys Ala Val Leu Leu Val Ala
1               5                   10                  15

Lys Phe Gln Asn Ser
            20

<210> SEQ ID NO 108
<211> LENGTH: 21

```
<212> TYPE: PRT
<213> ORGANISM: Artificial Sequence
<220> FEATURE:
<223> OTHER INFORMATION: Description of Artificial Sequence: Binding
      peptide

<400> SEQUENCE: 108

Pro Arg Ser Thr Pro Ser Leu Thr Thr Lys Ala Val Leu Leu Ala Arg
 1               5                  10                  15

Lys Phe Gln Asn Ser
            20

<210> SEQ ID NO 109
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 109

Pro Arg Ser Thr Pro Ser Leu Thr Thr Lys Ala Val Leu Ala Val Arg
 1               5                  10                  15

Lys Phe Gln Asn Ser
            20

<210> SEQ ID NO 110
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 110

Pro Arg Ser Thr Pro Ser Leu Thr Thr Lys Ala Val Ala Leu Val Arg
 1               5                  10                  15

Lys Phe Gln Asn Ser
            20

<210> SEQ ID NO 111
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 111

Pro Arg Ser Thr Pro Ser Leu Thr Thr Lys Ala Ala Leu Leu Val Arg
 1               5                  10                  15

Lys Phe Gln Asn Ser
            20

<210> SEQ ID NO 112
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 112

Pro Arg Ser Thr Pro Ser Leu Thr Thr Ala Ala Val Leu Leu Val Arg
 1               5                  10                  15
```

-continued

Lys Phe Gln Asn Ser
            20

<210> SEQ ID NO 113
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 113

Pro Arg Ser Thr Pro Ser Leu Thr Ala Lys Ala Val Leu Leu Val Arg
 1               5                  10                  15

Lys Phe Gln Asn Ser
            20

<210> SEQ ID NO 114
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 114

Pro Arg Ser Thr Pro Ser Leu Ala Thr Lys Ala Val Leu Leu Val Arg
 1               5                  10                  15

Lys Phe Gln Asn Ser
            20

<210> SEQ ID NO 115
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 115

Pro Arg Ser Thr Pro Ser Ala Thr Thr Lys Ala Val Leu Leu Val Arg
 1               5                  10                  15

Lys Phe Gln Asn Ser
            20

<210> SEQ ID NO 116
<211> LENGTH: 4
<212> TYPE: PRT
<213> ORGANISM: Artificial Sequence
<220> FEATURE:
<223> OTHER INFORMATION: Description of Artificial Sequence: Binding
      peptide

<400> SEQUENCE: 116

Val Leu Leu Val
 1

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
<221> NAME/KEY: PEPTIDE
<222> LOCATION: (5)
<223> OTHER INFORMATION: "Xaa" is a variable amino acid.

-continued

```
<400> SEQUENCE: 117

Leu Thr Thr Arg Xaa Val Leu Leu Val
 1               5

<210> SEQ ID NO 118
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 118

Ser Ser Phe Tyr Arg Leu Arg Phe Glu Leu Arg Tyr Arg Ala Glu Arg
 1               5                  10                  15

Ser Lys Thr Phe Thr
             20

<210> SEQ ID NO 119
<211> LENGTH: 20
<212> TYPE: PRT
<213> ORGANISM: Artificial Sequence
<220> FEATURE:
<223> OTHER INFORMATION: Description of Artificial Sequence: Binding
      peptide

<400> SEQUENCE: 119

Ser Ser Phe Tyr Arg Leu Arg Phe Glu Leu Arg Tyr Arg Ala Glu Arg
 1               5                  10                  15

Ser Lys Thr Phe
             20

<210> SEQ ID NO 120
<211> LENGTH: 19
<212> TYPE: PRT
<213> ORGANISM: Artificial Sequence
<220> FEATURE:
<223> OTHER INFORMATION: Description of Artificial Sequence: Binding
      peptide

<400> SEQUENCE: 120

Ser Ser Phe Tyr Arg Leu Arg Phe Glu Leu Arg Tyr Arg Ala Glu Arg
 1               5                  10                  15

Ser Lys Thr

<210> SEQ ID NO 121
<211> LENGTH: 18
<212> TYPE: PRT
<213> ORGANISM: Artificial Sequence
<220> FEATURE:
<223> OTHER INFORMATION: Description of Artificial Sequence: Binding
      peptide

<400> SEQUENCE: 121

Ser Ser Phe Tyr Arg Leu Arg Phe Glu Leu Arg Tyr Arg Ala Glu Arg
 1               5                  10                  15

Ser Lys

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Binding
      peptide
```

```
<400> SEQUENCE: 122

Ser Ser Phe Tyr Arg Leu Arg Phe Glu Leu Arg Tyr Arg Ala Glu Arg
  1               5                  10                  15
Ser

<210> SEQ ID NO 123
<211> LENGTH: 16
<212> TYPE: PRT
<213> ORGANISM: Artificial Sequence
<220> FEATURE:
<223> OTHER INFORMATION: Description of Artificial Sequence: Binding
      peptide

<400> SEQUENCE: 123

Ser Ser Phe Tyr Arg Leu Arg Phe Glu Leu Arg Tyr Arg Ala Glu Arg
  1               5                  10                  15

<210> SEQ ID NO 124
<211> LENGTH: 15
<212> TYPE: PRT
<213> ORGANISM: Artificial Sequence
<220> FEATURE:
<223> OTHER INFORMATION: Description of Artificial Sequence: Binding
      peptide

<400> SEQUENCE: 124

Ser Ser Phe Tyr Arg Leu Arg Phe Glu Leu Arg Tyr Arg Ala Glu
  1               5                  10                  15

<210> SEQ ID NO 125
<211> LENGTH: 14
<212> TYPE: PRT
<213> ORGANISM: Artificial Sequence
<220> FEATURE:
<223> OTHER INFORMATION: Description of Artificial Sequence: Binding
      peptide

<400> SEQUENCE: 125

Ser Ser Phe Tyr Arg Leu Arg Phe Glu Leu Arg Tyr Arg Ala
  1               5                  10

<210> SEQ ID NO 126
<211> LENGTH: 13
<212> TYPE: PRT
<213> ORGANISM: Artificial Sequence
<220> FEATURE:
<223> OTHER INFORMATION: Description of Artificial Sequence: Binding
      peptide

<400> SEQUENCE: 126

Ser Ser Phe Tyr Arg Leu Arg Phe Glu Leu Arg Tyr Arg
  1               5                  10

<210> SEQ ID NO 127
<211> LENGTH: 12
<212> TYPE: PRT
<213> ORGANISM: Artificial Sequence
<220> FEATURE:
<223> OTHER INFORMATION: Description of Artificial Sequence: Binding
      peptide

<400> SEQUENCE: 127

Ser Ser Phe Tyr Arg Leu Arg Phe Glu Leu Arg Tyr
  1               5                  10
```

```
<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Binding
      peptide

<400> SEQUENCE: 128

Ser Ser Phe Tyr Arg Leu Arg Phe Glu Leu Arg
 1               5                  10

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Binding
      peptide

<400> SEQUENCE: 129

Ser Ser Phe Tyr Arg Leu Arg Phe Glu Leu
 1               5                  10

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Binding
      peptide

<400> SEQUENCE: 130

Ser Ser Phe Tyr Arg Leu Arg Phe Glu
 1               5

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Binding
      peptide

<400> SEQUENCE: 131

Ser Ser Phe Tyr Arg Leu Arg Phe
 1               5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Binding
      peptide

<400> SEQUENCE: 132

Ser Ser Phe Tyr Arg Leu Arg
 1               5

<210> SEQ ID NO 133
<211> LENGTH: 6
<212> TYPE: PRT
<213> ORGANISM: Artificial Sequence
<220> FEATURE:
<223> OTHER INFORMATION: Description of Artificial Sequence: Binding
      peptide

<400> SEQUENCE: 133
```

Ser Ser Phe Tyr Arg Leu
 1               5

<210> SEQ ID NO 134
<211> LENGTH: 20
<212> TYPE: PRT
<213> ORGANISM: Artificial Sequence
<220> FEATURE:
<223> OTHER INFORMATION: Description of Artificial Sequence: Binding
      peptide

<400> SEQUENCE: 134

Ser Phe Tyr Arg Leu Arg Phe Glu Leu Arg Tyr Arg Ala Glu Arg Ser
 1               5                  10                  15

Lys Thr Phe Thr
             20

<210> SEQ ID NO 135
<211> LENGTH: 19
<212> TYPE: PRT
<213> ORGANISM: Artificial Sequence
<220> FEATURE:
<223> OTHER INFORMATION: Description of Artificial Sequence: Binding
      peptide

<400> SEQUENCE: 135

Phe Tyr Arg Leu Arg Phe Glu Leu Arg Tyr Arg Ala Glu Arg Ser Lys
 1               5                  10                  15

Thr Phe Thr

<210> SEQ ID NO 136
<211> LENGTH: 18
<212> TYPE: PRT
<213> ORGANISM: Artificial Sequence
<220> FEATURE:
<223> OTHER INFORMATION: Description of Artificial Sequence: Binding
      peptide

<400> SEQUENCE: 136

Tyr Arg Leu Arg Phe Glu Leu Arg Tyr Arg Ala Glu Arg Ser Lys Thr
 1               5                  10                  15

Phe Thr

<210> SEQ ID NO 137
<211> LENGTH: 17
<212> TYPE: PRT
<213> ORGANISM: Artificial Sequence
<220> FEATURE:
<223> OTHER INFORMATION: Description of Artificial Sequence: Binding
      peptide

<400> SEQUENCE: 137

Arg Leu Arg Phe Glu Leu Arg Tyr Arg Ala Glu Arg Ser Lys Thr Phe
 1               5                  10                  15

Thr

<210> SEQ ID NO 138
<211> LENGTH: 16
<212> TYPE: PRT
<213> ORGANISM: Artificial Sequence
<220> FEATURE:
<223> OTHER INFORMATION: Description of Artificial Sequence: Binding
      peptide

<400> SEQUENCE: 138

Leu Arg Phe Glu Leu Arg Tyr Arg Ala Glu Arg Ser Lys Thr Phe Thr
 1               5                  10                  15

<210> SEQ ID NO 139
<211> LENGTH: 15
<212> TYPE: PRT
<213> ORGANISM: Artificial Sequence
<220> FEATURE:
<223> OTHER INFORMATION: Description of Artificial Sequence: Binding
      peptide

<400> SEQUENCE: 139

Arg Phe Glu Leu Arg Tyr Arg Ala Glu Arg Ser Lys Thr Phe Thr
 1               5                  10                  15

<210> SEQ ID NO 140
<211> LENGTH: 14
<212> TYPE: PRT
<213> ORGANISM: Artificial Sequence
<220> FEATURE:
<223> OTHER INFORMATION: Description of Artificial Sequence: Binding
      peptide

<400> SEQUENCE: 140

Phe Glu Leu Arg Tyr Arg Ala Glu Arg Ser Lys Thr Phe Thr
 1               5                  10

<210> SEQ ID NO 141
<211> LENGTH: 13
<212> TYPE: PRT
<213> ORGANISM: Artificial Sequence
<220> FEATURE:
<223> OTHER INFORMATION: Description of Artificial Sequence: Binding
      peptide

<400> SEQUENCE: 141

Glu Leu Arg Tyr Arg Ala Glu Arg Ser Lys Thr Phe Thr
 1               5                  10

<210> SEQ ID NO 142
<211> LENGTH: 12
<212> TYPE: PRT
<213> ORGANISM: Artificial Sequence
<220> FEATURE:
<223> OTHER INFORMATION: Description of Artificial Sequence: Binding
      peptide

<400> SEQUENCE: 142

Leu Arg Tyr Arg Ala Glu Arg Ser Lys Thr Phe Thr
 1               5                  10

<210> SEQ ID NO 143
<211> LENGTH: 11
<212> TYPE: PRT
<213> ORGANISM: Artificial Sequence
<220> FEATURE:
<223> OTHER INFORMATION: Description of Artificial Sequence: Binding
      peptide

<400> SEQUENCE: 143

Arg Tyr Arg Ala Glu Arg Ser Lys Thr Phe Thr
 1               5                  10

<210> SEQ ID NO 144
<211> LENGTH: 10
<212> TYPE: PRT
<213> ORGANISM: Artificial Sequence

```
<220> FEATURE:
<223> OTHER INFORMATION: Description of Artificial Sequence: Binding
      peptide

<400> SEQUENCE: 144

Tyr Arg Ala Glu Arg Ser Lys Thr Phe Thr
 1               5                  10

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Binding
      peptide

<400> SEQUENCE: 145

Arg Ala Glu Arg Ser Lys Thr Phe Thr
 1               5

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Binding
      peptide

<400> SEQUENCE: 146

Ala Glu Arg Ser Lys Thr Phe Thr
 1               5

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Binding
      peptide

<400> SEQUENCE: 147

Glu Arg Ser Lys Thr Phe Thr
 1               5

<210> SEQ ID NO 148
<211> LENGTH: 6
<212> TYPE: PRT
<213> ORGANISM: Artificial Sequence
<220> FEATURE:
<223> OTHER INFORMATION: Description of Artificial Sequence: Binding
      peptide

<400> SEQUENCE: 148

Arg Ser Lys Thr Phe Thr
 1               5

<210> SEQ ID NO 149
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 149

Ser Ser Phe Tyr Arg Leu Arg Phe Glu Leu Arg Tyr Arg Ala Glu Arg
 1               5                  10                  15
```

Ser Lys Thr Phe Ala
          20

<210> SEQ ID NO 150
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 150

Ser Ser Phe Tyr Arg Leu Arg Phe Glu Leu Arg Tyr Arg Ala Glu Arg
 1               5                  10                  15

Ser Lys Thr Ala Thr
          20

<210> SEQ ID NO 151
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 151

Ser Ser Phe Tyr Arg Leu Arg Phe Glu Leu Arg Tyr Arg Ala Glu Arg
 1               5                  10                  15

Ser Lys Ala Phe Thr
          20

<210> SEQ ID NO 152
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 152

Ser Ser Phe Tyr Arg Leu Arg Phe Glu Leu Arg Tyr Arg Ala Glu Arg
 1               5                  10                  15

Ser Ala Thr Phe Thr
          20

<210> SEQ ID NO 153
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 153

Ser Ser Phe Tyr Arg Leu Arg Phe Glu Leu Arg Tyr Arg Ala Glu Arg
 1               5                  10                  15

Ala Lys Thr Phe Thr
          20

<210> SEQ ID NO 154
<211> LENGTH: 21
<212> TYPE: PRT
<213> ORGANISM: Artificial Sequence
<220> FEATURE:
<223> OTHER INFORMATION: Description of Artificial Sequence: Binding
      peptide

```
<400> SEQUENCE: 154

Ser Ser Phe Tyr Arg Leu Arg Phe Glu Leu Arg Tyr Arg Ala Glu Ala
  1               5                  10                  15

Ser Lys Thr Phe Thr
            20

<210> SEQ ID NO 155
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 155

Ser Ser Phe Tyr Arg Leu Arg Phe Glu Leu Arg Tyr Arg Ala Ala Arg
  1               5                  10                  15

Ser Lys Thr Phe Thr
            20

<210> SEQ ID NO 156
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 156

Ser Ser Phe Tyr Arg Leu Arg Phe Glu Leu Arg Tyr Ala Ala Glu Arg
  1               5                  10                  15

Ser Lys Thr Phe Thr
            20

<210> SEQ ID NO 157
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 157

Ser Ser Phe Tyr Arg Leu Arg Phe Glu Leu Arg Ala Arg Ala Glu Arg
  1               5                  10                  15

Ser Lys Thr Phe Thr
            20

<210> SEQ ID NO 158
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 158

Ser Ser Phe Tyr Arg Leu Arg Phe Glu Leu Ala Tyr Arg Ala Glu Arg
  1               5                  10                  15

Ser Lys Thr Phe Thr
            20

<210> SEQ ID NO 159
```

```
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 159

Ser Ser Phe Tyr Arg Leu Arg Phe Glu Ala Arg Tyr Arg Ala Glu Arg
 1               5                  10                  15

Ser Lys Thr Phe Thr
            20

<210> SEQ ID NO 160
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 160

Ser Ser Phe Tyr Arg Leu Arg Phe Ala Leu Arg Tyr Arg Ala Glu Arg
 1               5                  10                  15

Ser Lys Thr Phe Thr
            20

<210> SEQ ID NO 161
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 161

Ser Ser Phe Tyr Arg Leu Arg Ala Glu Leu Arg Tyr Arg Ala Glu Arg
 1               5                  10                  15

Ser Lys Thr Phe Thr
            20

<210> SEQ ID NO 162
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 162

Ser Ser Phe Tyr Arg Leu Ala Phe Glu Leu Arg Tyr Arg Ala Glu Arg
 1               5                  10                  15

Ser Lys Thr Phe Thr
            20

<210> SEQ ID NO 163
<211> LENGTH: 8
<212> TYPE: PRT
<213> ORGANISM: Artificial Sequence
<220> FEATURE:
<223> OTHER INFORMATION: Description of Artificial Sequence: Binding
      peptide

<400> SEQUENCE: 163

Leu Arg Tyr Arg Ala Glu Arg Ser
 1               5
```

```
<210> SEQ ID NO 164
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 164

Ala Thr Ser Leu Pro Val Gln Asp Ser Ser Val Pro Leu Pro Thr
 1               5                  10                  15

Phe Leu Val Ala Gly
             20

<210> SEQ ID NO 165
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 165

Val Gln Asp Ser Ser Val Pro Leu Pro Thr Phe Leu Val Ala Gly
 1               5                  10                  15

Gly Ser Leu Ala Phe
             20

<210> SEQ ID NO 166
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 166

Ser Val Pro Leu Pro Thr Phe Leu Val Ala Gly Gly Ser Leu Ala Phe
 1               5                  10                  15

Gly Thr Leu Leu Cys
             20

<210> SEQ ID NO 167
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 167

Thr Phe Leu Val Ala Gly Gly Ser Leu Ala Phe Gly Thr Leu Leu Cys
 1               5                  10                  15

Ile Ala Ile Val Leu
             20

<210> SEQ ID NO 168
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 168
```

Gly Gly Ser Leu Ala Phe Gly Thr Leu Leu Cys Ile Ala Ile Val Leu
 1               5                  10                  15

Arg Phe Lys Lys Thr
            20

<210> SEQ ID NO 169
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 169

Phe Gly Thr Leu Leu Cys Ile Ala Ile Val Leu Arg Phe Lys Lys Thr
 1               5                  10                  15

Trp Lys Leu Arg Ala
            20

<210> SEQ ID NO 170
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 170

Cys Ile Ala Ile Val Leu Arg Phe Lys Lys Thr Trp Lys Leu Arg Ala
 1               5                  10                  15

Leu Lys Glu Gly Lys
            20

<210> SEQ ID NO 171
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 171

Leu Arg Phe Lys Lys Thr Trp Lys Leu Arg Ala Leu Lys Glu Gly Lys
 1               5                  10                  15

Thr Ser Met His Pro
            20

<210> SEQ ID NO 172
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 172

Thr Trp Lys Leu Arg Ala Leu Lys Glu Gly Lys Thr Ser Met His Pro
 1               5                  10                  15

Pro Tyr Ser Leu Gly
            20

<210> SEQ ID NO 173
<211> LENGTH: 21
<212> TYPE: PRT

```
<213> ORGANISM: Artificial Sequence
<220> FEATURE:
<223> OTHER INFORMATION: Description of Artificial Sequence: Binding
      peptide

<400> SEQUENCE: 173

Ala Leu Lys Glu Gly Lys Thr Ser Met His Pro Pro Tyr Ser Leu Gly
 1               5                  10                  15

Gln Leu Val Pro Glu
            20

<210> SEQ ID NO 174
<211> LENGTH: 20
<212> TYPE: PRT
<213> ORGANISM: Artificial Sequence
<220> FEATURE:
<223> OTHER INFORMATION: Description of Artificial Sequence: Binding
      peptide

<400> SEQUENCE: 174

Gly Gly Ser Leu Ala Phe Gly Thr Leu Leu Cys Ile Ala Ile Val Leu
 1               5                  10                  15

Arg Phe Lys Lys
            20

<210> SEQ ID NO 175
<211> LENGTH: 19
<212> TYPE: PRT
<213> ORGANISM: Artificial Sequence
<220> FEATURE:
<223> OTHER INFORMATION: Description of Artificial Sequence: Binding
      peptide

<400> SEQUENCE: 175

Gly Gly Ser Leu Ala Phe Gly Thr Leu Leu Cys Ile Ala Ile Val Leu
 1               5                  10                  15

Arg Phe Lys

<210> SEQ ID NO 176
<211> LENGTH: 18
<212> TYPE: PRT
<213> ORGANISM: Artificial Sequence
<220> FEATURE:
<223> OTHER INFORMATION: Description of Artificial Sequence: Binding
      peptide

<400> SEQUENCE: 176

Gly Gly Ser Leu Ala Phe Gly Thr Leu Leu Cys Ile Ala Ile Val Leu
 1               5                  10                  15

Arg Phe

<210> SEQ ID NO 177
<211> LENGTH: 17
<212> TYPE: PRT
<213> ORGANISM: Artificial Sequence
<220> FEATURE:
<223> OTHER INFORMATION: Description of Artificial Sequence: Binding
      peptide

<400> SEQUENCE: 177

Gly Gly Ser Leu Ala Phe Gly Thr Leu Leu Cys Ile Ala Ile Val Leu
 1               5                  10                  15

Arg
```

```
<210> SEQ ID NO 178
<211> LENGTH: 16
<212> TYPE: PRT
<213> ORGANISM: Artificial Sequence
<220> FEATURE:
<223> OTHER INFORMATION: Description of Artificial Sequence: Binding
      peptide

<400> SEQUENCE: 178

Gly Gly Ser Leu Ala Phe Gly Thr Leu Leu Cys Ile Ala Ile Val Leu
  1               5                  10                  15

<210> SEQ ID NO 179
<211> LENGTH: 15
<212> TYPE: PRT
<213> ORGANISM: Artificial Sequence
<220> FEATURE:
<223> OTHER INFORMATION: Description of Artificial Sequence: Binding
      peptide

<400> SEQUENCE: 179

Gly Gly Ser Leu Ala Phe Gly Thr Leu Leu Cys Ile Ala Ile Val
  1               5                  10                  15

<210> SEQ ID NO 180
<211> LENGTH: 14
<212> TYPE: PRT
<213> ORGANISM: Artificial Sequence
<220> FEATURE:
<223> OTHER INFORMATION: Description of Artificial Sequence: Binding
      peptide

<400> SEQUENCE: 180

Gly Gly Ser Leu Ala Phe Gly Thr Leu Leu Cys Ile Ala Ile
  1               5                  10

<210> SEQ ID NO 181
<211> LENGTH: 13
<212> TYPE: PRT
<213> ORGANISM: Artificial Sequence
<220> FEATURE:
<223> OTHER INFORMATION: Description of Artificial Sequence: Binding
      peptide

<400> SEQUENCE: 181

Gly Gly Ser Leu Ala Phe Gly Thr Leu Leu Cys Ile Ala
  1               5                  10

<210> SEQ ID NO 182
<211> LENGTH: 12
<212> TYPE: PRT
<213> ORGANISM: Artificial Sequence
<220> FEATURE:
<223> OTHER INFORMATION: Description of Artificial Sequence: Binding
      peptide

<400> SEQUENCE: 182

Gly Gly Ser Leu Ala Phe Gly Thr Leu Leu Cys Ile
  1               5                  10

<210> SEQ ID NO 183
<211> LENGTH: 11
<212> TYPE: PRT
<213> ORGANISM: Artificial Sequence
<220> FEATURE:
<223> OTHER INFORMATION: Description of Artificial Sequence: Binding
      peptide

<400> SEQUENCE: 183
```

Gly Gly Ser Leu Ala Phe Gly Thr Leu Leu Cys
 1               5                   10

<210> SEQ ID NO 184
<211> LENGTH: 10
<212> TYPE: PRT
<213> ORGANISM: Artificial Sequence
<220> FEATURE:
<223> OTHER INFORMATION: Description of Artificial Sequence: Binding
      peptide

<400> SEQUENCE: 184

Gly Gly Ser Leu Ala Phe Gly Thr Leu Leu
 1               5                   10

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Binding
      peptide

<400> SEQUENCE: 185

Gly Gly Ser Leu Ala Phe Gly Thr Leu
 1               5

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: Binding
      peptide

<400> SEQUENCE: 186

Gly Gly Ser Leu Ala Phe Gly Thr
 1               5

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Binding
      peptide

<400> SEQUENCE: 187

Gly Gly Ser Leu Ala Phe Gly
 1               5

<210> SEQ ID NO 188
<211> LENGTH: 6
<212> TYPE: PRT
<213> ORGANISM: Artificial Sequence
<220> FEATURE:
<223> OTHER INFORMATION: Description of Artificial Sequence: Binding
      peptide

<400> SEQUENCE: 188

Gly Gly Ser Leu Ala Phe
 1               5

<210> SEQ ID NO 189
<211> LENGTH: 20
<212> TYPE: PRT
<213> ORGANISM: Artificial Sequence

```
<220> FEATURE:
<223> OTHER INFORMATION: Description of Artificial Sequence: Binding
      peptide

<400> SEQUENCE: 189

Gly Ser Leu Ala Phe Gly Thr Leu Leu Cys Ile Ala Ile Val Leu Arg
 1               5                  10                  15

Phe Lys Lys Thr
            20

<210> SEQ ID NO 190
<211> LENGTH: 19
<212> TYPE: PRT
<213> ORGANISM: Artificial Sequence
<220> FEATURE:
<223> OTHER INFORMATION: Description of Artificial Sequence: Binding
      peptide

<400> SEQUENCE: 190

Ser Leu Ala Phe Gly Thr Leu Leu Cys Ile Ala Ile Val Leu Arg Phe
 1               5                  10                  15

Lys Lys Thr

<210> SEQ ID NO 191
<211> LENGTH: 18
<212> TYPE: PRT
<213> ORGANISM: Artificial Sequence
<220> FEATURE:
<223> OTHER INFORMATION: Description of Artificial Sequence: Binding
      peptide

<400> SEQUENCE: 191

Leu Ala Phe Gly Thr Leu Leu Cys Ile Ala Ile Val Leu Arg Phe Lys
 1               5                  10                  15

Lys Thr

<210> SEQ ID NO 192
<211> LENGTH: 17
<212> TYPE: PRT
<213> ORGANISM: Artificial Sequence
<220> FEATURE:
<223> OTHER INFORMATION: Description of Artificial Sequence: Binding
      peptide

<400> SEQUENCE: 192

Ala Phe Gly Thr Leu Leu Cys Ile Ala Ile Val Leu Arg Phe Lys Lys
 1               5                  10                  15

Thr

<210> SEQ ID NO 193
<211> LENGTH: 16
<212> TYPE: PRT
<213> ORGANISM: Artificial Sequence
<220> FEATURE:
<223> OTHER INFORMATION: Description of Artificial Sequence: Binding
      peptide

<400> SEQUENCE: 193

Phe Gly Thr Leu Leu Cys Ile Ala Ile Val Leu Arg Phe Lys Lys Thr
 1               5                  10                  15

<210> SEQ ID NO 194
<211> LENGTH: 15
<212> TYPE: PRT
<213> ORGANISM: Artificial Sequence
```

-continued

```
<220> FEATURE:
<223> OTHER INFORMATION: Description of Artificial Sequence: Binding
      peptide

<400> SEQUENCE: 194

Gly Thr Leu Leu Cys Ile Ala Ile Val Leu Arg Phe Lys Lys Thr
 1               5                  10                  15

<210> SEQ ID NO 195
<211> LENGTH: 14
<212> TYPE: PRT
<213> ORGANISM: Artificial Sequence
<220> FEATURE:
<223> OTHER INFORMATION: Description of Artificial Sequence: Binding
      peptide

<400> SEQUENCE: 195

Thr Leu Leu Cys Ile Ala Ile Val Leu Arg Phe Lys Lys Thr
 1               5                  10

<210> SEQ ID NO 196
<211> LENGTH: 13
<212> TYPE: PRT
<213> ORGANISM: Artificial Sequence
<220> FEATURE:
<223> OTHER INFORMATION: Description of Artificial Sequence: Binding
      peptide

<400> SEQUENCE: 196

Leu Leu Cys Ile Ala Ile Val Leu Arg Phe Lys Lys Thr
 1               5                  10

<210> SEQ ID NO 197
<211> LENGTH: 12
<212> TYPE: PRT
<213> ORGANISM: Artificial Sequence
<220> FEATURE:
<223> OTHER INFORMATION: Description of Artificial Sequence: Binding
      peptide

<400> SEQUENCE: 197

Leu Cys Ile Ala Ile Val Leu Arg Phe Lys Lys Thr
 1               5                  10

<210> SEQ ID NO 198
<211> LENGTH: 11
<212> TYPE: PRT
<213> ORGANISM: Artificial Sequence
<220> FEATURE:
<223> OTHER INFORMATION: Description of Artificial Sequence: Binding
      peptide

<400> SEQUENCE: 198

Cys Ile Ala Ile Val Leu Arg Phe Lys Lys Thr
 1               5                  10

<210> SEQ ID NO 199
<211> LENGTH: 10
<212> TYPE: PRT
<213> ORGANISM: Artificial Sequence
<220> FEATURE:
<223> OTHER INFORMATION: Description of Artificial Sequence: Binding
      peptide

<400> SEQUENCE: 199

Ile Ala Ile Val Leu Arg Phe Lys Lys Thr
 1               5                  10
```

```
<210> SEQ ID NO 200
<211> LENGTH: 9
<212> TYPE: PRT
<213> ORGANISM: Artificial Sequence
<220> FEATURE:
<223> OTHER INFORMATION: Description of Artificial Sequence: Binding
      peptide

<400> SEQUENCE: 200

Ala Ile Val Leu Arg Phe Lys Lys Thr
 1               5

<210> SEQ ID NO 201
<211> LENGTH: 8
<212> TYPE: PRT
<213> ORGANISM: Artificial Sequence
<220> FEATURE:
<223> OTHER INFORMATION: Description of Artificial Sequence: Binding
      peptide

<400> SEQUENCE: 201

Ile Val Leu Arg Phe Lys Lys Thr
                 5

<210> SEQ ID NO 202
<211> LENGTH: 7
<212> TYPE: PRT
<213> ORGANISM: Artificial Sequence
<220> FEATURE:
<223> OTHER INFORMATION: Description of Artificial Sequence: Binding
      peptide

<400> SEQUENCE: 202

Val Leu Arg Phe Lys Lys Thr
                 5

<210> SEQ ID NO 203
<211> LENGTH: 6
<212> TYPE: PRT
<213> ORGANISM: Artificial Sequence
<220> FEATURE:
<223> OTHER INFORMATION: Description of Artificial Sequence: Binding
      peptide

<400> SEQUENCE: 203

Leu Arg Phe Lys Lys Thr
 1               5

<210> SEQ ID NO 204
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 204

Gly Gly Ser Leu Ala Phe Gly Thr Leu Leu Cys Ile Ala Ile Val Leu
 1               5                  10                  15

Arg Phe Lys Lys Ala
                 20

<210> SEQ ID NO 205
<211> LENGTH: 21
<212> TYPE: PRT
<213> ORGANISM: Artificial Sequence
<220> FEATURE:
```

-continued

```
<223> OTHER INFORMATION: Description of Artificial Sequence: Binding
      peptide

<400> SEQUENCE: 205

Gly Gly Ser Leu Ala Phe Gly Thr Leu Leu Cys Ile Ala Ile Val Leu
  1               5                  10                  15

Arg Phe Lys Ala Thr
            20

<210> SEQ ID NO 206
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 206

Gly Gly Ser Leu Ala Phe Gly Thr Leu Leu Cys Ile Ala Ile Val Leu
  1               5                  10                  15

Arg Phe Ala Lys Thr
            20

<210> SEQ ID NO 207
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 207

Gly Gly Ser Leu Ala Phe Gly Thr Leu Leu Cys Ile Ala Ile Val Leu
  1               5                  10                  15

Arg Ala Lys Lys Thr
            20

<210> SEQ ID NO 208
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 208

Gly Gly Ser Leu Ala Phe Gly Thr Leu Leu Cys Ile Ala Ile Val Leu
  1               5                  10                  15

Ala Phe Lys Lys Thr
            20

<210> SEQ ID NO 209
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 209

Gly Gly Ser Leu Ala Phe Gly Thr Leu Leu Cys Ile Ala Ile Val Ala
  1               5                  10                  15

Arg Phe Lys Lys Thr
            20
```

```
<210> SEQ ID NO 210
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 210

Gly Gly Ser Leu Ala Phe Gly Thr Leu Leu Cys Ile Ala Ile Ala Leu
 1               5                  10                  15

Arg Phe Lys Lys Thr
            20

<210> SEQ ID NO 211
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 211

Gly Gly Ser Leu Ala Phe Gly Thr Leu Leu Cys Ile Ala Ala Val Leu
 1               5                  10                  15

Arg Phe Lys Lys Thr
            20

<210> SEQ ID NO 212
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 212

Gly Gly Ser Leu Ala Phe Gly Thr Leu Leu Cys Ala Ala Ile Val Leu
 1               5                  10                  15

Arg Phe Lys Lys Thr
            20

<210> SEQ ID NO 213
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 213

Gly Gly Ser Leu Ala Phe Gly Thr Leu Leu Ala Ile Ala Ile Val Leu
 1               5                  10                  15

Arg Phe Lys Lys Thr
            20

<210> SEQ ID NO 214
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 214
```

```
Gly Gly Ser Leu Ala Phe Gly Thr Leu Ala Cys Ile Ala Ile Val Leu
 1               5                  10                  15

Arg Phe Lys Lys Thr
                20
```

<210> SEQ ID NO 215
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 215

```
Gly Gly Ser Leu Ala Phe Gly Thr Ala Leu Cys Ile Ala Ile Val Leu
 1               5                  10                  15

Arg Phe Lys Lys Thr
                20
```

<210> SEQ ID NO 216
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 216

```
Gly Gly Ser Leu Ala Phe Gly Ala Leu Leu Cys Ile Ala Ile Val Leu
 1               5                  10                  15

Arg Phe Lys Lys Thr
                20
```

<210> SEQ ID NO 217
<211> LENGTH: 21
<212> TYPE: PRT
<213> ORGANISM: Artificial Sequence
<220> FEATURE:
<223> OTHER INFORMATION: Description of Artificial Sequence: Binding
      peptide

<400> SEQUENCE: 217

```
Gly Gly Ser Leu Ala Phe Ala Thr Leu Leu Cys Ile Ala Ile Val Leu
 1               5                  10                  15

Arg Phe Lys Lys Thr
                20
```

<210> SEQ ID NO 218
<211> LENGTH: 7
<212> TYPE: PRT
<213> ORGANISM: Artificial Sequence
<220> FEATURE:
<223> OTHER INFORMATION: Description of Artificial Sequence: Binding
      peptide

<400> SEQUENCE: 218

```
Ile Ala Ile Val Leu Arg Phe
 1               5
```

<210> SEQ ID NO 219
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 219

Met Leu Thr Leu Gln Thr Trp Val Val Gln Ala Leu Phe Ile Phe Leu
 1               5                  10                  15

Thr Thr Glu Ser Thr Gly Glu Leu
            20

<210> SEQ ID NO 221
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 220

Ala Leu Phe Ile Phe Leu Thr Thr Glu Ser Thr Gly Glu Leu Leu Asp
 1               5                  10                  15

Pro Cys Gly Tyr Ile Ser Pro Glu
            20

<210> SEQ ID NO 221
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 221

Thr Gly Glu Leu Leu Asp Pro Cys Gly Tyr Ile Ser Pro Glu Ser Pro
 1               5                  10                  15

Val Val Gln Leu His Ser Asn Phe
            20

<210> SEQ ID NO 222
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 222

Ile Ser Pro Glu Ser Pro Val Val Gln Leu His Ser Asn Phe Thr Ala
 1               5                  10                  15

Val Cys Val Leu Lys Glu Lys Cys
            20

<210> SEQ ID NO 223
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 223

His Ser Asn Phe Thr Ala Val Cys Val Leu Lys Glu Lys Cys Met Asp
 1               5                  10                  15

Tyr Phe His Val Asn Ala Asn Tyr
            20

<210> SEQ ID NO 224

```
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 224

Lys Glu Lys Cys Met Asp Tyr Phe His Val Asn Ala Asn Tyr Ile Val
 1               5                  10                  15

Trp Lys Thr Asn His Phe Thr Ile
            20

<210> SEQ ID NO 225
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 225

Asn Ala Asn Tyr Ile Val Trp Lys Thr Asn His Phe Thr Ile Pro Lys
 1               5                  10                  15

Glu Gln Tyr Thr Ile Ile Asn Arg
            20

<210> SEQ ID NO 226
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 226

His Phe Thr Ile Pro Lys Glu Gln Tyr Thr Ile Ile Asn Arg Thr Ala
 1               5                  10                  15

Ser Ser Val Thr Phe Thr Asp Ile
            20

<210> SEQ ID NO 227
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 227

Ile Ile Asn Arg Thr Ala Ser Ser Val Thr Phe Thr Asp Ile Ala Ser
 1               5                  10                  15

Leu Asn Ile Gln Leu Thr Cys Asn
            20

<210> SEQ ID NO 228
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 228

Phe Thr Asp Ile Ala Ser Leu Asn Ile Gln Leu Thr Cys Asn Ile Leu
 1               5                  10                  15
```

Thr Phe Gly Gln Leu Glu Gln Asn
            20

<210> SEQ ID NO 229
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 229

Leu Thr Cys Asn Ile Leu Thr Phe Gly Gln Leu Glu Gln Asn Val Tyr
 1               5                  10                  15

Gly Ile Thr Ile Ile Ser Gly Leu
            20

<210> SEQ ID NO 230
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 230

Leu Glu Gln Asn Val Tyr Gly Ile Thr Ile Ile Ser Gly Leu Pro Pro
 1               5                  10                  15

Glu Lys Pro Lys Asn Leu Ser Cys
            20

<210> SEQ ID NO 231
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 231

Ile Ser Gly Leu Pro Pro Glu Lys Pro Lys Asn Leu Ser Cys Ile Val
 1               5                  10                  15

Asn Glu Gly Lys Lys Met Arg Cys
            20

<210> SEQ ID NO 232
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 232

Asn Leu Ser Cys Ile Val Asn Glu Gly Lys Lys Met Arg Cys Glu Trp
 1               5                  10                  15

Asp Gly Gly Arg Glu Thr His Leu
            20

<210> SEQ ID NO 233
<211> LENGTH: 24
<212> TYPE: PRT
<213> ORGANISM: Artificial Sequence
<220> FEATURE:
<223> OTHER INFORMATION: Description of Artificial Sequence: Binding peptide

<400> SEQUENCE: 233

Lys Met Arg Cys Glu Trp Asp Gly Gly Arg Glu Thr His Leu Glu Thr
  1               5                  10                  15

Asn Phe Thr Leu Lys Ser Glu Trp
            20

<210> SEQ ID NO 234
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 234

Glu Thr His Leu Glu Thr Asn Phe Thr Leu Lys Ser Glu Trp Ala Thr
  1               5                  10                  15

His Lys Phe Ala Asp Cys Lys Ala
            20

<210> SEQ ID NO 235
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 235

Lys Ser Glu Trp Ala Thr His Lys Phe Ala Asp Cys Lys Ala Lys Arg
  1               5                  10                  15

Asp Thr Pro Thr Ser Cys Thr Val
            20

<210> SEQ ID NO 236
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 236

Asp Cys Lys Ala Lys Arg Asp Thr Pro Thr Ser Cys Thr Val Asp Tyr
  1               5                  10                  15

Ser Thr Val Tyr Phe Val Asn Ile
            20

<210> SEQ ID NO 237
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 237

Ser Cys Thr Val Asp Tyr Ser Thr Val Tyr Phe Val Asn Ile Glu Val
  1               5                  10                  15

Trp Val Glu Ala Glu Asn Ala Leu
            20

-continued

```
<210> SEQ ID NO 238
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 238

Phe Val Asn Ile Glu Val Trp Val Glu Ala Glu Asn Ala Leu Gly Lys
  1               5                  10                  15

Val Thr Ser Asp His Ile Asn Phe
            20

<210> SEQ ID NO 239
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 239

Glu Asn Ala Leu Gly Lys Val Thr Ser Asp His Ile Asn Phe Asp Pro
  1               5                  10                  15

Val Tyr Lys Val Lys Pro Asn Pro
            20

<210> SEQ ID NO 240
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 240

His Ile Asn Phe Asp Pro Val Tyr Lys Val Lys Pro Asn Pro Pro His
  1               5                  10                  15

Asn Leu Ser Val Ile Asn Ser Glu
            20

<210> SEQ ID NO 241
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 241

Lys Pro Asn Pro Pro His Asn Leu Ser Val Ile Asn Ser Glu Glu Leu
  1               5                  10                  15

Ser Ser Ile Leu Lys Leu Thr Trp
            20

<210> SEQ ID NO 242
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 242

Ile Asn Ser Glu Glu Leu Ser Ser Ile Leu Lys Leu Thr Trp Thr Asn
```

```
                1               5                  10                 15
Pro Ser Ile Lys Ser Val Ile Ile
                            20
```

<210> SEQ ID NO 243
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 243

```
Lys Leu Thr Trp Thr Asn Pro Ser Ile Lys Ser Val Ile Ile Leu Lys
 1               5                  10                  15
Tyr Asn Ile Gln Tyr Arg Thr Lys
                  20
```

<210> SEQ ID NO 244
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 244

```
Ser Val Ile Ile Leu Lys Tyr Asn Ile Gln Tyr Arg Thr Lys Asp Ala
 1               5                  10                  15
Ser Thr Trp Ser Gln Ile Pro Pro
                  20
```

<210> SEQ ID NO 245
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 245

```
Tyr Arg Thr Lys Asp Ala Ser Thr Trp Ser Gln Ile Pro Pro Glu Asp
 1               5                  10                  15
Thr Ala Ser Thr Arg Ser Ser Phe
                  20
```

<210> SEQ ID NO 246
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 246

```
Gln Ile Pro Pro Glu Asp Thr Ala Ser Thr Arg Ser Ser Phe Thr Val
 1               5                  10                  15
Gln Asp Leu Lys Pro Phe Thr Glu
                  20
```

<210> SEQ ID NO 247
<211> LENGTH: 24
<212> TYPE: PRT
<213> ORGANISM: Artificial Sequence
<220> FEATURE:

```
<223> OTHER INFORMATION: Description of Artificial Sequence: Binding
      peptide

<400> SEQUENCE: 247

Arg Ser Ser Phe Thr Val Gln Asp Leu Lys Pro Phe Thr Glu Tyr Val
 1               5                  10                  15

Phe Arg Ile Arg Cys Met Lys Glu
             20

<210> SEQ ID NO 248
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 248

Pro Phe Thr Glu Tyr Val Phe Arg Ile Arg Cys Met Lys Glu Asp Gly
 1               5                  10                  15

Lys Gly Tyr Trp Ser Asp Trp Ser
             20

<210> SEQ ID NO 249
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 249

Cys Met Lys Glu Asp Gly Lys Gly Tyr Trp Ser Asp Trp Ser Glu Glu
 1               5                  10                  15

Ala Ser Gly Ile Thr Tyr Glu Asp
             20

<210> SEQ ID NO 250
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 250

Ser Asp Trp Ser Glu Glu Ala Ser Gly Ile Thr Tyr Glu Asp Arg Pro
 1               5                  10                  15

Ser Lys Ala Pro Ser Phe Trp Tyr
             20

<210> SEQ ID NO 251
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 251

Thr Tyr Glu Asp Arg Pro Ser Lys Ala Pro Ser Phe Trp Tyr Lys Ile
 1               5                  10                  15

Asp Pro Ser His Thr Gln Gly Tyr
             20
```

<210> SEQ ID NO 252
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 252

Ser Phe Trp Tyr Lys Ile Asp Pro Ser His Thr Gln Gly Tyr Arg Thr
 1               5                  10                  15

Val Gln Leu Val Trp Lys Thr Leu
            20

<210> SEQ ID NO 253
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 253

Thr Gln Gly Tyr Arg Thr Val Gln Leu Val Trp Lys Thr Leu Pro Pro
 1               5                  10                  15

Phe Glu Ala Asn Gly Lys Ile Leu
            20

<210> SEQ ID NO 254
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 254

Trp Lys Thr Leu Pro Pro Phe Glu Ala Asn Gly Lys Ile Leu Asp Tyr
 1               5                  10                  15

Glu Val Thr Leu Thr Arg Trp Lys
            20

<210> SEQ ID NO 255
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 255

Gly Lys Ile Leu Asp Tyr Glu Val Thr Leu Thr Arg Trp Lys Ser His
 1               5                  10                  15

Leu Gln Asn Tyr Thr Val Asn Ala
            20

<210> SEQ ID NO 256
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 256

```
Thr Arg Trp Lys Ser His Leu Gln Asn Tyr Thr Val Asn Ala Thr Lys
 1               5                  10                  15

Leu Thr Val Asn Leu Thr Asn Asp
             20
```

<210> SEQ ID NO 257
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 257

```
Thr Val Asn Ala Thr Lys Leu Thr Val Asn Leu Thr Asn Asp Arg Tyr
 1               5                  10                  15

Leu Ala Thr Leu Thr Val Arg Asn
             20
```

<210> SEQ ID NO 258
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 258

```
Leu Thr Asn Asp Arg Tyr Leu Ala Thr Leu Thr Val Arg Asn Leu Val
 1               5                  10                  15

Gly Lys Ser Asp Ala Ala Val Leu
             20
```

<210> SEQ ID NO 259
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 259

```
Thr Val Arg Asn Leu Val Gly Lys Ser Asp Ala Ala Val Leu Thr Ile
 1               5                  10                  15

Pro Ala Cys Asp Phe Gln Ala Thr
             20
```

<210> SEQ ID NO 260
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 260

```
Ala Ala Val Leu Thr Ile Pro Ala Cys Asp Phe Gln Ala Thr His Pro
 1               5                  10                  15

Val Met Asp Leu Lys Ala Phe Pro
             20
```

<210> SEQ ID NO 261
<211> LENGTH: 24
<212> TYPE: PRT
<213> ORGANISM: Artificial Sequence

```
<220> FEATURE:
<223> OTHER INFORMATION: Description of Artificial Sequence: Binding
      peptide

<400> SEQUENCE: 261

Phe Gln Ala Thr His Pro Val Met Asp Leu Lys Ala Phe Pro Lys Asp
 1               5                  10                  15

Asn Met Leu Trp Val Glu Trp Thr
            20

<210> SEQ ID NO 262
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 262

Lys Ala Phe Pro Lys Asp Asn Met Leu Trp Val Glu Trp Thr Thr Pro
 1               5                  10                  15

Arg Glu Ser Val Lys Lys Tyr Ile
            20

<210> SEQ ID NO 263
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 263

Val Glu Trp Thr Thr Pro Arg Glu Ser Val Lys Lys Tyr Ile Leu Glu
 1               5                  10                  15

Trp Cys Val Leu Ser Asp Lys Ala
            20

<210> SEQ ID NO 264
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 264

Lys Lys Tyr Ile Leu Glu Trp Cys Val Leu Ser Asp Lys Ala Pro Cys
 1               5                  10                  15

Ile Thr Asp Trp Gln Gln Glu Asp
            20

<210> SEQ ID NO 265
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 265

Ser Asp Lys Ala Pro Cys Ile Thr Asp Trp Gln Gln Glu Asp Gly Thr
 1               5                  10                  15

Val His Arg Thr Tyr Leu Arg Gly
            20
```

```
<210> SEQ ID NO 266
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 266

Gln Gln Glu Asp Gly Thr Val His Arg Thr Tyr Leu Arg Gly Asn Leu
 1               5                  10                  15

Ala Glu Ser Lys Cys Tyr Leu Ile
             20

<210> SEQ ID NO 267
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 267

Tyr Leu Arg Gly Asn Leu Ala Glu Ser Lys Cys Tyr Leu Ile Thr Val
 1               5                  10                  15

Thr Pro Val Tyr Ala Asp Gly Pro
             20

<210> SEQ ID NO 268
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 268

Cys Tyr Leu Ile Thr Val Thr Pro Val Tyr Ala Asp Gly Pro Gly Ser
 1               5                  10                  15

Pro Glu Ser Ile Lys Ala Tyr Leu
             20

<210> SEQ ID NO 269
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 269

Ala Asp Gly Pro Gly Ser Pro Glu Ser Ile Lys Ala Tyr Leu Lys Gln
 1               5                  10                  15

Ala Pro Pro Ser Lys Gly Pro Thr
             20

<210> SEQ ID NO 270
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 270
```

```
Lys Ala Tyr Leu Lys Gln Ala Pro Pro Ser Lys Gly Pro Thr Val Arg
 1               5                  10                  15

Thr Lys Lys Val Gly Lys Asn Glu
            20

<210> SEQ ID NO 271
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 271

Lys Gly Pro Thr Val Arg Thr Lys Lys Val Gly Lys Asn Glu Ala Val
 1               5                  10                  15

Leu Glu Trp Asp Gln Leu Pro Val
            20

<210> SEQ ID NO 272
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 272

Gly Lys Asn Glu Ala Val Leu Glu Trp Asp Gln Leu Pro Val Asp Val
 1               5                  10                  15

Gln Asn Gly Phe Ile Arg Asn Tyr
            20

<210> SEQ ID NO 273
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 273

Gln Leu Pro Val Asp Val Gln Asn Gly Phe Ile Arg Asn Tyr Thr Ile
 1               5                  10                  15

Phe Tyr Arg Thr Ile Ile Gly Asn
            20

<210> SEQ ID NO 274
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 274

Ile Arg Asn Tyr Thr Ile Phe Tyr Arg Thr Ile Ile Gly Asn Glu Thr
 1               5                  10                  15

Ala Val Asn Val Asp Ser Ser His
            20

<210> SEQ ID NO 275
<211> LENGTH: 24
<212> TYPE: PRT
```

```
<213> ORGANISM: Artificial Sequence
<220> FEATURE:
<223> OTHER INFORMATION: Description of Artificial Sequence: Binding
      peptide

<400> SEQUENCE: 275

Ile Ile Gly Asn Glu Thr Ala Val Asn Val Asp Ser Ser His Thr Glu
  1               5                  10                  15

Tyr Thr Leu Ser Ser Leu Thr Ser
             20

<210> SEQ ID NO 276
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 276

Asp Ser Ser His Thr Glu Tyr Thr Leu Ser Ser Leu Thr Ser Asp Thr
  1               5                  10                  15

Leu Tyr Met Val Arg Met Ala Ala
             20

<210> SEQ ID NO 277
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 277

Ser Leu Thr Ser Asp Thr Leu Tyr Met Val Arg Met Ala Ala Tyr Thr
  1               5                  10                  15

Asp Glu Gly Gly Lys Asp Gly Pro
             20

<210> SEQ ID NO 278
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 278

Arg Met Ala Ala Tyr Thr Asp Glu Gly Gly Lys Asp Gly Pro Glu Phe
  1               5                  10                  15

Thr Phe Thr Thr Pro Lys Phe Ala
             20

<210> SEQ ID NO 279
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 279

Lys Asp Gly Pro Glu Phe Thr Phe Thr Thr Pro Lys Phe Ala Gln Gly
  1               5                  10                  15

Glu Ile Glu Ala Ile Val Val Pro
```

```
              20

<210> SEQ ID NO 280
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 280

Pro Lys Phe Ala Gln Gly Glu Ile Glu Ala Ile Val Val Pro Val Cys
  1               5                  10                  15

Leu Ala Phe Leu Leu Thr Thr Leu
              20

<210> SEQ ID NO 281
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 281

Ile Val Val Pro Val Cys Leu Ala Phe Leu Leu Thr Thr Leu Leu Gly
  1               5                  10                  15

Val Leu Phe Cys Phe Asn Lys Arg
              20

<210> SEQ ID NO 282
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 282

Leu Thr Thr Leu Leu Gly Val Leu Phe Cys Phe Asn Lys Arg Asp Leu
  1               5                  10                  15

Ile Lys Lys His Ile Trp Pro Asn
              20

<210> SEQ ID NO 283
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 283

Phe Asn Lys Arg Asp Leu Ile Lys Lys His Ile Trp Pro Asn Val Pro
  1               5                  10                  15

Asp Pro Ser Lys Ser His Ile Ala
              20

<210> SEQ ID NO 284
<211> LENGTH: 24
<212> TYPE: PRT
<213> ORGANISM: Artificial Sequence
<220> FEATURE:
<223> OTHER INFORMATION: Description of Artificial Sequence: Binding
      peptide
```

```
<400> SEQUENCE: 284

Ile Trp Pro Asn Val Pro Asp Pro Ser Lys Ser His Ile Ala Gln Trp
 1               5                  10                  15

Ser Pro His Thr Pro Pro Arg His
            20

<210> SEQ ID NO 285
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 285

Ser His Ile Ala Gln Trp Ser Pro His Thr Pro Pro Arg His Asn Phe
 1               5                  10                  15

Asn Ser Lys Asp Gln Met Tyr Ser
            20

<210> SEQ ID NO 286
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 286

Pro Pro Arg His Asn Phe Asn Ser Lys Asp Gln Met Tyr Ser Asp Gly
 1               5                  10                  15

Asn Phe Thr Asp Val Ser Val Val
            20

<210> SEQ ID NO 287
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 287

Gln Met Tyr Ser Asp Gly Asn Phe Thr Asp Val Ser Val Val Glu Ile
 1               5                  10                  15

Glu Ala Asn Asp Lys Lys Pro Phe
            20

<210> SEQ ID NO 288
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 288

Val Ser Val Val Glu Ile Glu Ala Asn Asp Lys Lys Pro Phe Pro Glu
 1               5                  10                  15

Asp Leu Lys Ser Leu Asp Leu Phe
            20

<210> SEQ ID NO 289
<211> LENGTH: 24
```

```
<212> TYPE: PRT
<213> ORGANISM: Artificial Sequence
<220> FEATURE:
<223> OTHER INFORMATION: Description of Artificial Sequence: Binding
      peptide

<400> SEQUENCE: 289

Lys Lys Pro Phe Pro Glu Asp Leu Lys Ser Leu Asp Leu Phe Lys Lys
 1               5                  10                  15

Glu Lys Ile Asn Thr Glu Gly His
            20

<210> SEQ ID NO 290
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 290

Leu Asp Leu Phe Lys Lys Glu Lys Ile Asn Thr Glu Gly His Ser Ser
 1               5                  10                  15

Gly Ile Gly Gly Ser Ser Cys Met
            20

<210> SEQ ID NO 291
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 291

Thr Glu Gly His Ser Ser Gly Ile Gly Gly Ser Ser Cys Met Ser Ser
 1               5                  10                  15

Ser Arg Pro Ser Ile Ser Ser Ser
            20

<210> SEQ ID NO 292
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 292

Ser Ser Cys Met Ser Ser Ser Arg Pro Ser Ile Ser Ser Ser Asp Glu
 1               5                  10                  15

Asn Glu Ser Ser Gln Asn Thr Ser
            20

<210> SEQ ID NO 293
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 293

Ile Ser Ser Ser Asp Glu Asn Glu Ser Ser Gln Asn Thr Ser Ser Thr
 1               5                  10                  15
```

```
Val Gln Tyr Ser Thr Val Val His
            20

<210> SEQ ID NO 294
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 294

Gln Asn Thr Ser Ser Thr Val Gln Tyr Ser Thr Val Val His Ser Gly
 1               5                  10                  15

Tyr Arg His Gln Val Pro Ser Val
            20

<210> SEQ ID NO 295
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 295

Thr Val Val His Ser Gly Tyr Arg His Gln Val Pro Ser Val Gln Val
 1               5                  10                  15

Phe Ser Arg Ser Glu Ser Thr Gln
            20

<210> SEQ ID NO 296
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 296

Val Pro Ser Val Gln Val Phe Ser Arg Ser Glu Ser Thr Gln Pro Leu
 1               5                  10                  15

Leu Asp Ser Glu Glu Arg Pro Glu
            20

<210> SEQ ID NO 297
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 297

Glu Ser Thr Gln Pro Leu Leu Asp Ser Glu Glu Arg Pro Glu Asp Leu
 1               5                  10                  15

Gln Leu Val Asp His Val Asp Gly
            20

<210> SEQ ID NO 298
<211> LENGTH: 24
<212> TYPE: PRT
<213> ORGANISM: Artificial Sequence
<220> FEATURE:
<223> OTHER INFORMATION: Description of Artificial Sequence: Binding
      peptide
```

```
<400> SEQUENCE: 298

Glu Arg Pro Glu Asp Leu Gln Leu Val Asp His Val Asp Gly Gly Asp
  1               5                  10                  15

Gly Ile Leu Pro Arg Gln Gln Tyr
            20

<210> SEQ ID NO 299
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 299

His Val Asp Gly Gly Asp Gly Ile Leu Pro Arg Gln Gln Tyr Phe Lys
  1               5                  10                  15

Gln Asn Cys Ser Gln His Glu Ser
            20

<210> SEQ ID NO 300
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 300

Arg Gln Gln Tyr Phe Lys Gln Asn Cys Ser Gln His Glu Ser Ser Pro
  1               5                  10                  15

Asp Ile Ser His Phe Glu Arg Ser
            20

<210> SEQ ID NO 301
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 301

Gln His Glu Ser Ser Pro Asp Ile Ser His Phe Glu Arg Ser Lys Gln
  1               5                  10                  15

Val Ser Ser Val Asn Glu Glu Asp
            20

<210> SEQ ID NO 302
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 302

Phe Glu Arg Ser Lys Gln Val Ser Ser Val Asn Glu Glu Asp Phe Val
  1               5                  10                  15

Arg Leu Lys Gln Gln Ile Ser Asp
            20

<210> SEQ ID NO 303
```

```
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 303

Asn Glu Glu Asp Phe Val Arg Leu Lys Gln Gln Ile Ser Asp His Ile
  1               5                  10                  15

Ser Gln Ser Cys Gly Ser Gly Gln
            20

<210> SEQ ID NO 304
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 304

Gln Ile Ser Asp His Ile Ser Gln Ser Cys Gly Ser Gly Gln Met Lys
  1               5                  10                  15

Met Phe Gln Glu Val Ser Ala Ala
            20

<210> SEQ ID NO 305
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 305

Gly Ser Gly Gln Met Lys Met Phe Gln Glu Val Ser Ala Ala Asp Ala
  1               5                  10                  15

Phe Gly Pro Gly Thr Glu Gly Gln
            20

<210> SEQ ID NO 306
<211> LENGTH: 24
<212> TYPE: PRT
<213> ORGANISM: Artificial Sequence
<220> FEATURE:
<223> OTHER INFORMATION: Description of Artificial Sequence: Synthetic

<400> SEQUENCE: 306

Val Ser Ala Ala Asp Ala Phe Gly Pro Gly Thr Glu Gly Gln Val Glu
  1               5                  10                  15

Arg Phe Glu Thr Val Gly Met Glu
            20

<210> SEQ ID NO 307
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 307

Thr Glu Gly Gln Val Glu Arg Phe Glu Thr Val Gly Met Glu Ala Ala
  1               5                  10                  15
```

-continued

```
Thr Asp Glu Gly Met Pro Lys Ser
            20

<210> SEQ ID NO 308
<211> LENGTH: 24
<212> TYPE: PRT
<213> ORGANISM: Artificial Sequence
<220> FEATURE:
<223> OTHER INFORMATION: Description of Artificial Sequence: Binding
      peptide

<400> SEQUENCE: 308

Val Gly Met Glu Ala Ala Thr Asp Glu Gly Met Pro Lys Ser Tyr Leu
 1               5                  10                  15

Pro Gln Thr Val Arg Gln Gly Gly
            20

<210> SEQ ID NO 309
<211> LENGTH: 18
<212> TYPE: PRT
<213> ORGANISM: Artificial Sequence
<220> FEATURE:
<223> OTHER INFORMATION: Description of Artificial Sequence: Binding
      peptide

<400> SEQUENCE: 309

Met Pro Lys Ser Tyr Leu Pro Gln Thr Val Arg Gln Gly Gly Tyr Met
 1               5                  10                  15

Pro Gln
```